(12) United States Patent
Sparr et al.

(10) Patent No.: US 11,214,687 B2
(45) Date of Patent: Jan. 4, 2022

(54) SMALL-MOLECULE ORGANIC DYES

(71) Applicant: UNIVERSITÄT BASEL, Basel (CH)

(72) Inventors: Christof Sparr, Rickenbach (CH); Christian Fischer, Bern (CH)

(73) Assignee: UNIVERSITÄT BASEL, Basel (CH)

( * ) Notice: Subject to any disclaimer, the term of this patent is extended or adjusted under 35 U.S.C. 154(b) by 122 days.

(21) Appl. No.: 16/643,173

(22) PCT Filed: Aug. 28, 2018

(86) PCT No.: PCT/EP2018/073151
§ 371 (c)(1),
(2) Date: Feb. 28, 2020

(87) PCT Pub. No.: WO2019/057451
PCT Pub. Date: Mar. 28, 2019

(65) Prior Publication Data
US 2020/0255667 A1  Aug. 13, 2020

(30) Foreign Application Priority Data

Aug. 29, 2017 (EP) ..................................... 17188288

(51) Int. Cl.
*C07D 219/06* (2006.01)
*C09B 15/00* (2006.01)
*C07D 311/86* (2006.01)
*C09B 11/24* (2006.01)

(52) U.S. Cl.
CPC ............ *C09B 15/00* (2013.01); *C07D 219/06* (2013.01); *C07D 311/86* (2013.01); *C09B 11/24* (2013.01)

(58) Field of Classification Search
CPC ..... C07D 219/06; C07D 311/86; C09B 15/00; C09B 11/24
See application file for complete search history.

(56) References Cited

U.S. PATENT DOCUMENTS

| | | | |
|---|---|---|---|
| 3,021,334 A | 2/1962 | Smart | |
| 3,431,264 A | 3/1969 | Desmond et al. | |
| 4,150,134 A | 4/1979 | Schulenberg | |

FOREIGN PATENT DOCUMENTS

| | | |
|---|---|---|
| CN | 103980882 A | 8/2014 |
| WO | WO2009103798 A1 | 8/2009 |

OTHER PUBLICATIONS

Commandeur, Eur J Org Chern, 2011, 1447-1454. (Year: 2011).*
Amruta Joshi-Pangu et al: "Acridinium-Based Photocatalysts: A Sustainable Option in Photo redo Catalysis", The Journal of Organic Chemi stry, vol. 81, No. 16, Jul. 25, 2016 (Jul. 25, 2016), pp. 7244-7249.
Nagao Yukinori et al.: "Syntheses and properties of N-methylacridines", Senryo to Yakuhin—Dyestuffs and Chemicals, Kaseihin Kogyo Kyokai, Tokyo, JP,vol. 34, No. 1,Jan. 1, 1989 (Jan. 1, 1989), pp. 8-15.
Dale J. Wi lger et al.: The direct anti-Markovnikov addition of mineral acids to styrenes, Nature Chemistry, Jul. 13, 2014 (Jul. 13, 2014), XP055420071, GB ISSN: 1755-4330, DOI: 10.1038/nchem. 2000.
Shunichi Fukuzumi et al: "Photoalkylation of 10-Alkylacridinium Ion via a Charge-Shift Type of Photoinduced Electron Transfer Controlled by Solvent Polarity". Journal of the American Chemical Society. vol. 123. No. 35.Sep. 1, 2001 (Sep. 1, 2001). pp. 8459-8467. XP055420072. US ISSN: 0002-7863. 001: 10.1021/ja0043111.

* cited by examiner

*Primary Examiner* — D Margaret M Seaman
(74) *Attorney, Agent, or Firm* — Nguyen Tarbet LLC

(57) ABSTRACT

The present invention relates to compounds of formula (A), wherein Z is $NR^{10}$ or O. These compounds represent novel acridinium and xanthylium salts having an unprecedented substituted heterocyclic core. They are useful as fluorescent dyes or precursors thereof in different applications including various imaging and sensing techniques, and, in particular, as photosensitizers and hereby preferably as photocatalysts. The present invention further relates to processes for preparing the inventive compounds via 1,5-organodimetallic reagents from double directed ortho-metalation reactions or combined halogen-metal exchange/directed ortho-metalation reactions.

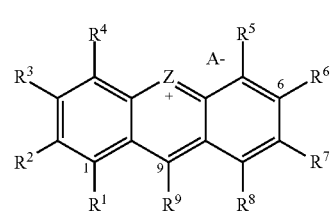

14 Claims, 2 Drawing Sheets

SMALL-MOLECULE ORGANIC DYES

The present invention relates in particular to compounds of the general formula (A).

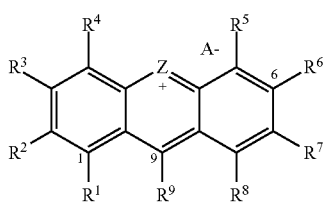

These compounds represent novel acridinium and xanthylium salts having an unprecedented substituted heterocyclic core. They are useful as fluorescent dyes or precursors thereof in different applications including various imaging and sensing techniques, and, in particular, as photosensitizers and hereby preferably as organophotocatalysts. The present invention further relates to processes for preparing the inventive compounds via 1,5-organodimetallic reagents from double directed ortho-metalation reactions or combined halogenmetal exchange/directed ortho-metalation reactions.

RELATED ART

Photocatalysis has become an integral part of organic synthesis. By applying visible light and photosensitizers in catalytic amounts, reactions can be performed often close to room temperature e.g. to overcome activation barriers or create thermodynamically unfavored products, not accessible by thermal processes (B. Konig, et al. *Angew. Chem. Int. Ed.* 2018, 57, 10034). The most frequently used photocatalysts today are transition-metal polypyridyl complexes (J. Weaver, et al., *Org. Process Res. Dev.* 2016, 20, 1156), due to their powerful electrochemical and photophysical properties which can furthermore effectively be tuned by changing the ligand structure. However, both ruthenium or iridium, rare and expensive transition-metals, make these metallophotocatalysts ecologically and economically disadvantageous.

Heterocyclic fluorophores, such as acridinium salts were shown to act as photosensitizers (S. Fukuzumi, et al., *J. Am. Chem. Soc.* 2004, 126, 1600; C.-T. Chen, et al., *Org. Lett.* 2009, 11, 4858; S. Fukuzumi, et al., *J. Am. Chem. Soc.* 2004, 126, 1600; D. J. Wilger et al. *Nature Chemistry.* 2014, 6, 720; D. DiRocco, et al., *J. Org. Chem.* 2016, 81, 7244; D. A. Nicewicz, et al., *Nat. Chem.* 2014, 6, 720; *Chem. Rev.* 2016, 116, 10075). However, it remains difficult to replace transition-metal complexes as e.g. their excited state reduction potential and other electrochemical and photophysical properties cannot be adjusted to different applications, such as photocatalysis; unlike transition-metal based photocatalysts (see FIG. 1). Furthermore, the ability to fine-tune the excited state reduction potential to match the photochemical of acridinium photocatalysts is currently limited as existing synthesis strategies involve Friedel-Crafts acylation, Bernthsen synthesis or nucleophilic aromatic substitution, leading in addition to the 9,10-substitution to either unsubstituted or symmetrically substituted and derivatized 3,6- or 2,7- or 1,8,3,6-substitution (A. Baeyer, *Liebigs Ann. Chem.* 1907, 354, 80; M. Cérésole, 1887, DE44002; M. Wada, et al., *Bull. Chem. Soc. Jpn.* 1995, 68, 243; L. Lavis *Annu. Rev. Biochem* 2017, 86, 825-843; CN103980882; D. DiRocco, et al., *J. Org. Chem.* 2016, 81, 7244; D. Nicewicz, et al., *Chem. Rev.* 2016, 116, 10075; B. W. Laursen, et al., *Chem. Eur. J.* 2001, 7, 1773; J. Lacour, et al., *Chem. Soc. Rev.* 2014, 43, 2824; T. J. Srensen, et al., 2016, WO2015/058777, WO2016/116111). As the substitution pattern of heterocyclic fluorophores is closely related to the photophysical and electrochemical properties (compare Mes-3,6-$(MeO)_2$-PhAcr and Mes-2,7-$(MeO)_2$-PhAcr in FIG. 1), novel substitution patterns are required, using methodologies which allow modulation and fine-tuning of their properties across a broad range in order to ameliorate fluorescent dyes, photosensitizers and, in particular, organophotocatalysts for contemporary photochemical reactions.

SUMMARY OF THE INVENTION

The present invention now provides access to a novel class of acridinium salts, xanthylium salts, as well as the intermediates 9,10-dihydroacridin-9-ols, xanthen-9-ols, respectively, having an unprecedented 1,8- or 1,6 or 1- or 1,7-substitution on the heterocyclic core, which are readily accessible by way of a highly efficient and modular three-step synthesis. Said inventive process, namely the formation of 1,5-organodimetallic reagents from double directed ortho-metalation reactions or combined halogen-metal exchange/ directed ortho-metalation reactions followed by the use of carboxylic acid esters which are easy to handle and ubiquitous in organic chemistry allow access to a broad diversity of acridinium salts, xanthylium salts, and its intermediates having not only an unprecedented non-symmetric substitution pattern, but in addition, an unprecedented symmetric substitution pattern. Thus, the inventive acridinium salts, xanthylium salts, and its intermediates have not only an unprecedented non-symmetric and symmetric substitution pattern at the 1,8 and/or 3,6 and/or 2,7-position and/or has substituents at the 9-position with a barrier to rotation, potentially leading to atropisomers but, furthermore, at the other positions of the heterocyclic core as well, in particular, due to the ease of precedent derivatization and substitution such as nitration, sulfonation, halogenation, alkylation and the like.

The versatility of the unprecedented substitution pattern of the inventive compounds allow tailoring of the photophysical and photochemical properties such as in particular the ground and excited state reduction potentials, thereby nearly doubling the redox window previously accessible by acridinium photocatalysts (FIG. 2). Further, embodiments of the present invention demonstrated efficient photocatalytic properties, outcompeting previous organophotocatalysts and replacing expensive metallophotocatalysts. Further, embodiments of the present invention demonstrated increased Stokes shifts and enhanced excited state lifetimes as compared to commonly known acridinium and xanthylium salts.

Therefore in a first aspect, the present invention provides a compound of formula (A)

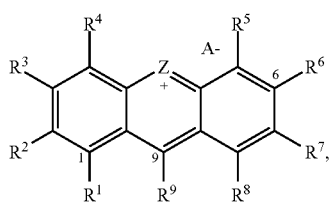

wherein

Z is $NR^{10}$ or O;

$R^1$ is selected from C1-C6-alkoxy, aryloxy, O-alkyl-aryl, C1-C6-hydroxyalkyl, $O(CH_2)O(CH_3)$, $O(CH_2)O(CH_2)_2OCH_3$, $NH_2$, N(H)(C1-C6-alkyl), $N(C1-C6-alkyl)_2$, SH, F, $CF_3$, C1-C6-alkylthio, 4,4-dimethyl-4,5-dihydrooxazole, $NHCOR^{14}$, $NHCO_2R^{14}$, $OCNR_2$, $CONHR^{14}$, $CON(R^{14})_2$, $C=NR^{14}$, $CO_2H$, $[CO_2^-]$, $CO_2R^{14}$, $SO_3R^{14}$, $SO_3H$, $SO_2NC(CH_3)_3$, $[SO_3]$, $SO_2N(R^{14})_2$;

$R^2$ is selected from H, halogen, $NO_2$, CN, $NH_2$, N(H)(C1-C6-alkyl), $N(C1-C6-alkyl)_2$, OH, C1-C6-hydroxyalkyl, SH, C1-C6-alkylthio, C1-C12-alkyl, $SO_3H$, $[SO_3]$, $SO_3R^{14}$, $CO_2H$, $[CO_2]$, $CO_2R^{14}$;

$R^3$ is selected from H, halogen, $NO_2$, $NH_2$, N(H)(C1-C6-alkyl), $N(C1-C6-alkyl)_2$ and CN;

$R^4$ is selected from H, C1-C12-alkyl, halogen, $NO_2$, CN, $NH_2$, N(H)(C1-C6-alkyl), $N(C1-C6-alkyl)_2$, OH, C1-C6-alko xy, aryloxy, O-alkyl-aryl, C1-C6-hydroxyalkyl, SH, C1-C6-alkylthio, $SO_3H$, $[SO_3^-]$, $SO_3R^{14}$;

$R^5$ is selected from H, C1-C12-alkyl, halogen, $NO_2$, CN, $NH_2$, N(H)(C1-C6-alkyl), $N(C1-C6-alkyl)_2$, OH, C1-C6-hydroxyalkyl, SH, C1-C6-alkylthio, $SO_3H$, $[SO_3^{31}]$, $SO_3R^{14}$;

$R^6$ is selected from H, halogen, $NO_2$, CN, $NH_2$, N(H)(C1-C6-alkyl), $N(C1-C6-alkyl)_2$, C1-C6-hydroxyalkyl;

$R^7$ is selected from H, halogen, $NO_2$, CN, $NH_2$, N(H)(C1-C6-alkyl), $N(C1-C6-alkyl)_2$, OH, C1-C6-alkoxy, C1-C6-hydroxyalkyl, SH, C1-C6-alkylthio, C1-C12-alkyl, $SO_3H$, $[SO_3^-]$, $SO_3R^{14}$, $CO_2H$, $[CO_2^-]$, $CO_2R^{14}$;

$R^8$ is selected from H, halogen, C1-C6-alkoxy, OH, C1-C6-hydroxyalkyl, $O(CH_2)O(CH_3)$, $O(CH_2)O(CH_2)_2OCH_3$, $NH_2$, N(H)(C1-C6-alkyl), N(C1-C6-alkyl), SH, F, $CF_3$, C1-C6-alkylthio, 4,4-dimethyl-4,5-dihydrooxazole, $NHCOR^{14}$, $NHCO_2R^{14}$, $OCN(R^{14})_2$, $CONHR^{14}$, $CON(R^{14})_2$, $C=NR^{14}$, $CO_2H$, $[CO_2^-]$, $NO_2$, $SO_3R^{14}$, $SO_3H$, $SO_2NC(CH_3)_3$ and $SO_2N(R^{14})_2$;

$R^9$ is selected from aryl, heteroaryl, C2-C6-alkenyl-aryl, C2-C12-alkenyl, C2-C12-alkynyl, C1-C12-alkyl, $NH_2$, N(H)(C1-C6-alkyl), $N(C1-C6-alkyl)_2$, C1-C12-alkoxy, C1-C12-hydroxyalkyl, C1-C4-alkyl-C1-C4-alkyl-$CO_2H$, C1-C4-alkyl-$CO_2$-C1-C6-alkyl, C(=O)H, C(=O)—C1-C6-alkyl and C1-C12-alkylthio; and wherein said aryl and heteroaryl are optionally substituted by one or more groups independently selected from halogen atoms, CN, $N_3$, C1-C6-alkyl, $[SO_3]$, $SO_3H$, $SO_2Cl$, OH, C1-C6-alkoxy, $CO_2^-$, C(=O)OH and C1-C6-alkoxycarbonyl, C1-C12-hydroxyalkyl, C1-C12-thio alkyl;

$R^{10}$ is selected from aryl, heteroaryl, C1-C4-alkyl-aryl, C2-C6-alkenyl-aryl, C2-C12-alkenyl, C2-C12-alkynyl, C1-C12-alkyl, H, C1-C12-hydroxyalkyl, C(=O)H, C(=O)-C1-C6-alkyl, C1-C12-alkylthio, C1-C12-alkyl-$CO_2H$, C1-C12-alkyl-$CO_2$-C1-C12-alkyl, C1-C12-alkyl-$CO_2$-C1-C4-alkyl-aryl, $O^-$, S(=O)-C1-C6-alkyl, S(=O) aryl, S(=O)-heteroaryl, $S(O_2)$-C1-C6-alkyl, $S(O_2)$-aryl, $S(O_2)$-heteroaryl; wherein said aryl and heteroaryl are optionally substituted by one or more groups independently selected from halogen atoms, CN, $N_3$, C1-C6-alkyl, $[SO_3]^-$, $SO_3H$, $SO_2Cl$, OH, C1-C6-alkoxy, C(=O)OH and C1-C6-alkoxycarbonyl;

$R^{14}$ is selected from C1-C12-alkyl; and

A is a suitable anion preferably selected from halide ions, $[BF_4]^-$, $[PF_6]^-$, $[ClO_4]^-$, $[(C1-C5-alkyl)C(=O)O]^-$, $[aryl-CH_2-C(=O)O]^-$, $[aryl-C(=O)O]^-$, $[H_2PO_4]^-$ $[HSO_4]^-$ $[SO_4]^{2-}$, $[(C1-C6-alkyl)SO_3]^-$, $[CF_3SO_3]^-$, $[aryl-CH_2-SO_3]^-$ and $[aryl-SO_3]^-$ and wherein when $R^3$ and $R^6$ are independently selected from $NH_2$, N(H)(C1-C6-alkyl), $N(C1-C6-alkyl)_2$, then $R^9$ is C2-C6-alkenyl-aryl, C2-C12-alkenyl, C2-C12-alkynyl, $NH_2$, N(H)(C1-C6-alkyl), $N(C1-C6-alkyl)_2$, halogen, CN, $N_3$, C(=O)H, C(=O)—C1-C6-alkyl, C1-C12-alkylthio or aryl, wherein said aryl is substituted by one or more groups independently selected from C1-C6-alkyl, C1-C12-hydroxyalkyl, C1-C12-thio alkyl or $N_3$; and wherein when Z is $NR^{10}$, $R^1$ and $R^8$ is OMe, then $R^9$ is not 2,6-dimethoxyphenyl or 4-$(N(R^{15})_2)$-2,6-dimethoxyphenyl, wherein $R^{15}$ is $CH_3$, $C_2H_5$ or $C_6H_{13}$; and wherein when Z is O, $R^1$ or $R^8$ is OMe, then $R^9$ is not 2,6-dimethoxyphenyl; and wherein when Z is O, $R^1$ or $R^8$ is OMe, then $R^9$ is not phenyl.

The inventive compounds are depicted in formula (A), but the present invention including the inventive compounds and inventive processes encompass all resonance formulas of (A) thereof. Said resonance formulas of (A) are perfectly known to the skilled person in the art.

In a further aspect, the present invention provides for a compound of formula (A')

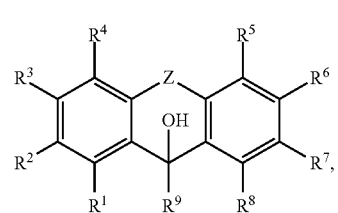

wherein

Z is $NR^{10}$;

$R^1$ is selected from C1-C6-alkoxy, aryloxy, O-alkyl-aryl, C1-C6-hydroxyalkyl, $O(CH_2)O(CH_3)$, $O(CH_2)O(CH_2)_2OCH_3$, $NH_2$, N(H)(C1-C6-alkyl), $N(C1-C6-alkyl)_2$, SH, F, $CF_3$, C1-C6-alkylthio, 4,4-dimethyl-4,5-dihydrooxazole, $NHCOR^{14}$, $NHCO_2R^{14}$, $OCNR_2$, $CONHR^{14}$, $CON(R^{14})_2$, $C=NR^{14}$, $CO_2H$, $[CO_2^-]$, $CO_2R^{14}$, $[SO_3^-]$, $SO_3R^{14}$, $SO_3H$, $SO_2NC(CH_3)_3$, $SO_2N(R^{14})_2$;

$R^2$ is selected from H, halogen, $NO_2$, CN, $NH_2$, N(H)(C1-C6-alkyl), $N(C1-C6-alkyl)_2$, OH, C1-C6-alkoxy, C1-C6-hydroxyalkyl, SH, C1-C6-alkylthio, $[SO_3^-]$, $SO_3H$, $SO_3R^{14}$, $CO_2H$, $[CO_2^-]$, $CO_2R^{14}$, C1-C12-alkyl;

$R^3$ is selected from H, halogen, $NO_2$, and CN;

$R^4$ is selected from H, C1-C12-alkyl, halogen, $NO_2$, CN, $NH_2$, N(H)(C1-C6-alkyl), $N(C1-C6-alkyl)_2$, OH, C1-C6-alkoxy, aryloxy, O-alkyl-aryl, C1-C6-hydroxyalkyl, SH, C1-C6-alkylthio, $SO_3R^{14}$, $[SO_3]$, $SO_3H$;

$R^5$ is selected from H, C1-C12-alkyl, halogen, $NO_2$, CN, $NH_2$, N(H)(C1-C6-alkyl), $N(C1-C6-alkyl)_2$, OH, C1-C6-hydroxyalkyl, SH, C1-C6-alkylthio, $SO_3R^{14}$, $SO_3H$, $[SO_3^-]$;

$R^6$ is selected from H, halogen, $NO_2$, CN, $NH_2$, N(H)(C1-C6-alkyl), $N(C1-C6-alkyl)_2$, C1-C6-hydroxyalkyl;

$R^7$ is selected from H, halogen, $NO_2$, CN, $NH_2$, N(H)(C1-C6-alkyl), $N(C1-C6-alkyl)_2$, OH, C1-C6-alkoxy and C1-C6-hydroxyalkyl, SH, C1-C6-alkylthio, C1-C12-alkyl, $SO_3R^{14}$, $SO_3H$, $[SO_3]$, $CO_2H$, $[CO_2^-]$, $CO_2R^{14}$;

$R^8$ is selected from H, halogen, C1-C6-alkoxy, OH, C1-C6-hydroxyalkyl, $O(CH_2)O(CH_3)$, $O(CH_2)O(CH_2)_2OCH_3$, $NH_2$, N(H)(C1-C6-alkyl), $N(C1-C6-alkyl)_2$, SH, F, $CF_3$, C1-C6-alkylthio, 4,4-dimethyl-4,5-dihydrooxazole, $NHCOR^{14}$, $NHCO_2R^{14}$, $OCNR_2$, $CONHR^{14}$, $CON(R^{14})_2$, $C=NR^{14}$, $CO_2H$, $[CO_2^-]$, $NO_2$, $SO_3R^{14}$, $SO_3H$, $SO_2NC(CH_3)_3$ and $SO_2N(R^{14})_2$;

$R^9$ is selected from aryl, heteroaryl, C2-C6-alkenyl-aryl, C2-C12-alkenyl, C2-C12-alkynyl, C1-C12-alkyl, $NH_2$, N(H)(C1-C6-alkyl), N(C1-C6-alkyl)$_2$, C1-C12-alkoxy, C1-C12-hydroxyalkyl, C1-C4-alkyl-C1-C4-alkyl-CO$_2$H, C1-C4-alkyl-CO$_2$-C1-C6-alkyl, C(=O)H, C(=O)-C1-C6-alkyl and C1-C12-alkylthio; and wherein said aryl and heteroaryl are optionally substituted by one or more groups independently selected from halogen atoms, CN, N$_3$, C1-C6-alkyl, [SO$_3$]$^-$, SO$_3$H, SO$_2$Cl, OH, C1-C6-alkoxy, C(=O)OH and C1-C6-alkoxycarbonyl, C1-C12-hydroxyalkyl, C1-C12-thio alkyl;

R$^{10}$ is selected from aryl, heteroaryl, C1-C4-alkyl-aryl, C2-C6-alkenyl-aryl, C2-C12-alkenyl, C2-C12-alkynyl, C1-C12-alkyl, H, C1-C12-hydroxyalkyl, C(=O)H, C(=O)-C1-C6-alkyl, C1-C12-alkylthio, C1-C12-alkyl-CO$_2$H; C1-C12-alkyl-CO$_2$-C1-C12-alkyl, C1-C12-alkyl-CO$_2$-C1-C4-alkyl-aryl, [O$^-$]; S(=O)-C1-C6-alkyl, S(=O)aryl, S(=O)-heteroaryl, S(O$_2$)—C1-C6-alkyl, S(O$_2$)-aryl, S(O$_2$)-heteroaryl; wherein said aryl and heteroaryl are optionally substituted by one or more groups independently selected from halogen atoms, CN, N$_3$, C1-C6-alkyl, [SO$_3$]$^-$, SO$_3$H, SO$_2$Cl, OH, C1-C6-alkoxy, C(=O)OH and C1-C6-alkoxycarbonyl;

R$^{14}$ is selected from C1-C12-alkyl.

In a further aspect, the present invention provides for a process for the preparation of the inventive compound of formula (A), comprising
(i) reacting a compound of formula (A''') with an organometallic reagent (R$^{12}$M) selected from aryl-MgX, C1-C6-alkyl-MgX, aryl-Li and C1-C6-alkyl-Li;

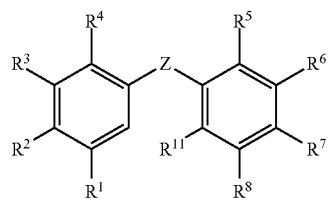

to form a compound of formula (A'')

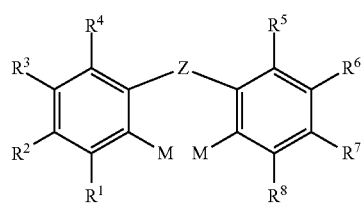

wherein when R'' is H, then R$^8$ is selected from C1-C6-alkoxy, OH, C1-C6-hydroxyalkyl, O(CH$_2$)O(CH$_3$), O(CH$_2$)O(CH$_2$)$_2$OCH$_3$, NH$_2$, N(H)(C1-C6-alkyl), N(C1-C6-alkyl)$_2$, SH, F, CF$_3$, C1-C6-alkylthio, 4,4-dimethyl-4,5-dihydrooxazole, NHCOR$^{14}$, NHCO$_2$R$^{14}$, OCN(R$^{14}$)$_2$, CONFIR$^{14}$, CON(R$^{14}$)$_2$, C=NR$^{14}$, CO$_2$H, [CO$_2$], SO$_3$R$^{14}$, SO$_3$H, [SO$_3^-$], SO$_2$NC(CH$_3$)$_3$, SO$_2$N(R$^{14}$)$_2$; and wherein when R$^{11}$ is halogen, then R$^8$ is selected from C1-C6-alkoxy, OH, C1-C6-hydroxyalkyl, O(CH$_2$)O(CH$_3$), O(CH$_2$)O(CH$_2$)$_2$OCH$_3$, NH$_2$, N(H)(C1-C6-alkyl), N(C1-C6-alkyl)$_2$, SH, F, CF$_3$, C1-C6-alkylthio, 4,4-dimethyl-4,5-dihydrooxazole, NHCOR$^{14}$, NHCO$_2$R$^{14}$, OCN(R$^{14}$)$_2$, CONHR$^{14}$, CON(R$^{14}$)$_2$, C=NR$^{14}$, CO$_2$H, [CO$_2$], SO$_3$R$^{14}$, SO$_3$H, [SO$_3^-$], SO$_2$NC(CH$_3$)$_3$, SO$_2$N(R$^{14}$)$_2$ and H; and wherein M is Li when the organometallic reagent (R$^{12}$M) is aryl-Li or C1-C6-alkyl-Li; and wherein M is MgX when the organometallic reagent (R$^{12}$M) is aryl-MgX or C1-C6-alkyl-MgX or MgX$_2$ or alkyl$_2$Mg or aryl$_2$Mg; and wherein X is a halogen; and wherein R$^1$ to R$^7$ and Z are defined as in any one of the claims 1 to 10;

(ii) followed by reacting said compound of formula (A'') with a compound of formula (B) or (C)

to form a compound of formula (A')

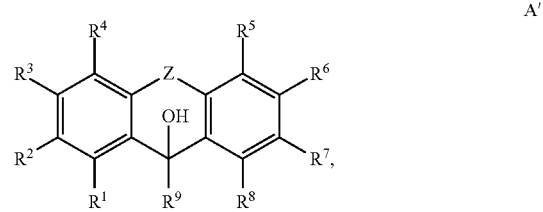

wherein R$^9$ is defined as in any one of the claims 1 to 10; and wherein R$^{13}$ is C1-C6-alkyl, C1-C6-alkanoyl; or wherein R$^9$ and R$^{13}$ together with the atoms to which they are attached form a 4 to 6-membered ring optionally substituted by C2-C6-alkenyl-aryl, C2-C12-alkenyl, C2-C12-alkynyl, C1-C12-alkyl, NH$_2$, N(H)(C1-C6-alkyl), N(C1-C6-alkyl)$_2$, C1-C12-alkoxy, C1-C12-hydroxyalkyl, halogen, CN, N$_3$, C1-C4-alkyl-CO$_2$H, C1-C4-alkyl-CO$_2$-C1-C6-alkyl, C(=O)H, C(=O)—C1-C6-alkyl and C1-C12-alkylthio ; or wherein R$^9$ and R$^{13}$ together with the atoms to which they are attached form a 4 to 6-membered ring fused to an aryl or heteraryl, wherein said aryl or heteraryl is optionally substituted by one or more groups independently selected from halogen atoms, CN, N$_3$, C1-C6-alkyl, [SO$_3$]$^-$, SO$_3$H, SO$_2$Cl, OH, C1-C6-alkoxy, C(=O)OH and C1-C6-alkoxycarbonyl, C1-C12-hydroxyalkyl, C1-C12-thio alkyl;

(iii) addition of a protonic acid HA to form a compound of formula (A), wherein said HA is a suitable acid preferably selected from an inorganic acid or an organic acid, and wherein further preferably said inorganic acid is selected from HBr, HCl, HI, HBF$_4$, HPF$_6$ and HClO$_4$, and said organic acid is selected from (C1-C5-alkyl)C(=O)OH, aryl-CH$_2$—C(=O)OH, [aryl-C(=O)OH, H$_3$PO$_4$, (C1-C6-alkyl)SO$_3$H, aryl-CH$_2$—SO$_3$H and aryl-SO$_3$H, and wherein again further preferably said inorganic acid is selected from HBr, HCl, HBF$_4$, HPF$_6$ and HClO$_4$, and said organic acid is selected from (C1-C6-alkyl)SO$_3$H.

In a further aspect, the present invention provides for a process for the preparation of the compound of formula (A)

7

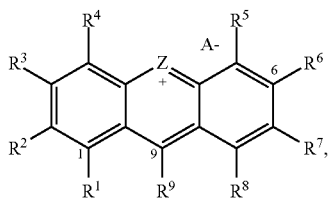

wherein

Z is selected from $NR^{10}$ and O;

$R^1$ is selected from C1-C6-alkoxy, OH, aryloxy, O-alkylaryl, C1-C6-hydroxyalkyl, $O(CH_2)O(CH_3)$, $O(CH_2)O(CH_2)_2OCH_3$, $NH_2$, N(H)(C1-C6-alkyl), N(C1-C6-alkyl)$_2$, SH, F, $CF_3$, C1-C6-alkylthio, 4,4-dimethyl-4,5-dihydrooxazole, $NHCOR^{14}$, $NHCO_2R^{14}$, $OCNR_2$, $CONHR^{14}$, $CON(R^{14})_2$, $C=NR^{14}$, $CO_2H$, $[CO_2]$, $CO_2R^{14}$, $SO_3R^{14}$, $SO_3H$, $[SO_3]$, $SO_2NC(CH_3)_3$, $SO_2N(R^{14})_2$;

$R^2$ is selected from H, halogen, $NO_2$, CN, $NH_2$, N(H)(C1-C6-alkyl), N(C1-C6-alkyl)$_2$, OH, C1-C6-alkoxy, C1-C6-hydroxyalkyl, SH, C1-C6-alkylthio, C1-C12-alkyl, $SO_3H$, $[SO_3]$, $SO_3R^{14}$, $CO_2H$, $[CO_2^-]$, $CO_2R^{14}$;

$R^3$ is selected from H, halogen, $NO_2$, $NH_2$, N(H)(C1-C6-alkyl), N(C1-C6-alkyl)$_2$, $NH_2$, N(H)(C1-C6-alkyl), N(C1-C6-alkyl)$_2$, OH, SH, C1-C6-alkylthio and CN;

$R^4$ is selected from H, C1-C12-alkyl, halogen, $NO_2$, CN, $NH_2$, N(H)(C1-C6-alkyl), N(C1-C6-alkyl)$_2$, OH, C1-C6-alkoxy, aryloxy, O-alkyl-aryl, C1-C6-hydroxyalkyl, SH, C1-C6-alkylthio, $SO_3H$, $[SO_3]$, $SO_3R^{14}$;

$R^5$ is selected from H, C1-C12-alkyl, halogen, $NO_2$, CN, $NH_2$, N(H)(C1-C6-alkyl), N(C1-C6-alkyl)$_2$, OH, C1-C6-alkoxy, aryloxy, O-alkyl-aryl, C1-C6-hydroxyalkyl, SH, C1-C6-alkylthio, $SO_3H$, $[SO_3]$, $SO_3R^{14}$;

$R^6$ is selected from H, halogen, $NO_2$, CN, $NH_2$, N(H)(C1-C6-alkyl), N(C1-C6-alkyl), OH, C1-C6-alkoxy, aryloxy, O-alkyl-aryl, C1-C6-hydroxyalkyl, SH, C1-C6-alkylthio;

$R^7$ is selected from H, halogen, $NO_2$, CN, $NH_2$, N(H)(C1-C6-alkyl), N(C1-C6-alkyl)$_2$, OH, C1-C6-alkoxy, C1-C6-hydroxyalkyl, SH, C1-C6-alkylthio, C1-C12-alkyl, $SO_3H$, $[SO_3]$, $SO_3R^{14}$, $CO_2H$, $[CO_2^-]$, $CO_2R^{14}$;

$R^8$ is selected from H, C1-C6-alkoxy, OH, C1-C6-hydroxyalkyl, $O(CH_2)O(CH_3)$, $O(CH_2)_2OCH_3$, $NH_2$, N(H)(C1-C6-alkyl), N(C1-C6-alkyl)$_2$, SH, F, $CF_3$, C1-C6-alkylthio, 4,4-dimethyl-4,5-dihydrooxazole, $NHCOR^{14}$, $NHCO_2R^{14}$, $OCN(R^{14})_2$, $CONHR^{14}$, $CON(R^{14})_2$, $C=NR^{14}$, $CO_2H$, $[CO_2^-]$, $NO_2$, $SO_3R^{14}$, $SO_3H$, $SO_2NC(CH_3)_3$ and $SO_2N(R^{14})_2$;

$R^9$ is selected from aryl, heteroaryl, C1-C4-alkyl-aryl, C2-C6-alkenyl-aryl, C2-C12-alkenyl, C2-C12-alkynyl, C1-C12-alkyl, H, $NH_2$, N(H)(C1-C6-alkyl), N(C1-C6-alkyl)$_2$, C1-C12-alkoxy, C1-C12-hydroxyalkyl, C(=O)H, C(=O)-C1-C6-alkyl and C1-C12-alkylthio; and wherein said aryl and heteroaryl are optionally substituted by one or more groups independently selected from halogen atoms, CN, $N_3$, C1-C6-alkyl, $[SO_3^-]$, $SO_3H$, $SO_2Cl_5$ OH, C1-C6-alkoxy, C1-C4-alkyl-$CO_2H$, C1-C4-alkyl-$CO_2$—C1-C6-alkyl, C(=O)OH and C1-C6-alkoxycarbonyl, C1-C12-hydroxyalkyl, C1-C12-thio alkyl;

$R^{10}$ is selected from aryl, heteroaryl, C1-C4-alkyl-aryl, C2-C6-alkenyl-aryl, C2-C12-alkenyl, C2-C12-alkynyl, C1-C12-alkyl, H, C1-C12-hydroxyalkyl, C(=O)H, C(=O)-C1-C6-alkyl, C1-C12-alkylthio, C1-C12-alkyl-$CO_2H$; C1-C12-alkyl-$CO_2$-C1-C12-alkyl, C1-C12-alkyl-$CO_2$—C1-C4-alkyl- aryl, O$^-$; S(=O)—C1-C6-alkyl, S(=O)aryl, S(=O)-heteroaryl, $S(O_2)$—C1-C6-alkyl, $S(O_2)$-aryl, $S(O_2)$-heteroaryl; wherein said aryl and heteroaryl are optionally substituted by one or more groups independently selected from halogen atoms, CN, $N_3$, C1-C6-alkyl, $[SO_3^-]$, $SO_3H$, $SO_2Cl$, OH, C1-C6-alkoxy, C(=O)OH and C1-C6-alkoxycarbonyl;

$R^{14}$ is selected from C1-C12-alkyl; and $A^-$ is a suitable anion preferably selected from halide ions, $[BF_4]^-$, $[PF_6]^-$, $[ClO_4]^-$, $[(C1-C5-alkyl)C(=O)O]^-$, $[aryl-CH_2-C(=O)O]^-$, $[aryl-C(=O)O]^-$, $[H_2PO_4]^-$ $[HSO_4]^-$ $[SO_4]^{2-}$, $[(C1-C6-alkyl)SO_3]^-$, $[CF_3SO_3]^-$, aryl-$CH_2$-$SO_3$]$^-$ and [aryl-$SO_3$]$^-$;

comprising (i) reacting a compound of formula (A') with an organometallic reagent ($R^{12}M$) selected from aryl-MgX, C1-C6-alkyl-MgX, aryl-Li and C1-C6-alkyl-Li;

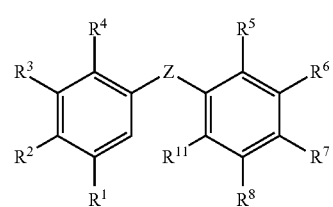

to form a compound of formula (A'')

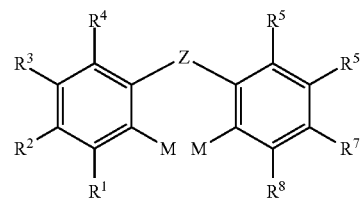

wherein when $R^{11}$ is H, then $R^8$ is selected from C1-C6-alkoxy, OH, C1-C6-hydroxyalkyl, $O(CH_2)O(CH_3)$, $O(CH_2)O(CH_2)_2OCH_3$, $NH_2$, N(H)(C1-C6-alkyl), N(C1-C6-alkyl)$_2$, SH, F, $CF_3$, C1-C6-alkylthio, 4,4-dimethyl-4,5-dihydrooxazole, $NHCOR^{14}$, $NHCO_2R^{14}$, $OCN(R^{14})_2$, $CONHR^{14}$, $CON(R^{14})_2$, $C=NR^{14}$, $CO_2H$, $[CO_2]$, $SO_3R^{14}$, $SO_3H$, $[SO_3^-]$, $SO_2NC(CH_3)_3$, $SO_2N(R^{14})_2$; and wherein when $R^{11}$ is halogen, then $R^8$ is selected from C1-C6-alkoxy, OH, C1-C6-hydroxyalkyl, $O(CH_2)O(CH_3)$, $O(CH_2)O(CH_2)_2OCH_3$, $NH_2$, N(H)(C1-C6-alkyl), N(C1-C6-alkyl)$_2$, SH, F, $CF_3$, C1-C6-alkylthio, 4,4-dimethyl-4,5-dihydrooxazole, $NHCOR^{14}$, $NHCO_2R^{14}$, $OCN(R^{14})_2$, $CONHR^{14}$, $CON(R^{14})_2$, $C=NR^{14}$, $CO_2H$, $[CO_2]$, $SO_3R^{14}$, $SO_3H$, $[SO_3^-]$, $SO_2NC(CH_3)_3$, $SO_2N(R^{14})_2$ and H; and wherein M is Li when the organometallic reagent ($R^{12}M$) is aryl-Li or C1-C6-alkyl-Li; and wherein M is MgX when the organometallic reagent ($R^{12}M$) is aryl-MgX or C1-C6-alkyl-MgX or $MgX_2$ or alkyl$_2$Mg or aryl$_2$Mg; and wherein X is a halogen;

(ii) followed by reacting said compound of formula (A") with a compound of formula (B) or (C)

  (B)

  (C)

to form a compound of formula (A'),
wherein $R^{13}$ is C1-C6-alkyl, C1-C6-alkanoyl; or
wherein $R^9$ and $R^{13}$ together with the atoms to which they are attached form a 4 to 6-membered ring optionally substituted by C2-C6-alkenyl-aryl, C2-C12-alkenyl, C2-C12-alkynyl, C1-C12-alkyl, $NH_2$, N(H)(C1-C6-alkyl), N(C1-C6-alkyl)$_2$, C1-C12-alkoxy, C1-C12-hydroxyalkyl, halogen, CN, $N_3$, C1-C4-alkyl-$CO_2H$, C1-C4-alkyl-$CO_2$-C1-C6-alkyl, C(=O)H, C(=O)-C1-C6-alkyl and C1-C12-alkylthio; or wherein $R^9$ and $R^{13}$ together with the atoms to which they are attached form a 4 to 6-membered ring fused to an aryl or heteraryl, wherein said aryl or heteraryl is optionally substituted by one or more groups independently selected from halogen atoms, CN, $N_3$, C1-C6-alkyl, [$SO_3^-$], $SO_3H$, $SO_2Cl$, OH, C1-C6-alkoxy, C(=O)OH and C1-C6-alkoxycarbonyl, C1-C12-hydroxyalkyl, C1-C12-thio alkyl;
(iii) addition of a protonic acid HA to form a compound of formula (A), wherein said HA is a suitable acid preferably selected from an inorganic acid or an organic acid, and wherein further preferably said inorganic acid is selected from HBr, HCl, HI, $HBF_4$, $HPF_6$ and $HClO_4$, and said organic acid is selected from (C1-C5-alkyl)C(=O)OH, aryl-$CH_2$—C(=O)OH, [aryl-C(=O)OH, $H_3PO_4$, (C1-C6-alkyl)$SO_3H$, aryl-$CH_2$—$SO_3H$ and aryl-$SO_3H$, and wherein again further preferably said inorganic acid is selected from HBr, HCl, $HBF_4$, $HPF_6$ and $HClO_4$, and said organic acid is selected from (C1-C6-alkyl)$SO_3H$.

In a further aspect, the present invention provides a use of a compound of formula (A) described herein as a fluorescent dye and a compound of formula (A') as a precursor thereof.

In a further aspect, the present invention provides a fluorescent dye comprising a compound of formula (A) described herein and a compound of formula (A') as an off-switch.

In a further aspect, the present invention provides a sensor comprising a compound of formula (A) and a compound of formula (A') as a precursor thereof.

In a further aspect, the present invention provides a use of a compound of formula (A) and (A') described herein in imaging, preferably in life cell imaging.

In a further aspect, the present invention provides a use of a compound of formula (A) and (A') described herein as a photosensitizer.

In a further aspect, the present invention provides a use of a compound of formula (A) and (A') described herein as a photocatalyst.

In a further aspect, the present invention provides a compound of formula (A) described herein, wherein said compound of formula (A) or (A') is conjugated to a biomolecule, e.g. an antibody.

Further aspects and embodiments of the present invention will become apparent as this description continues.

DETAILED DESCRIPTION OF THE INVENTION

Definitions

Figure 1:
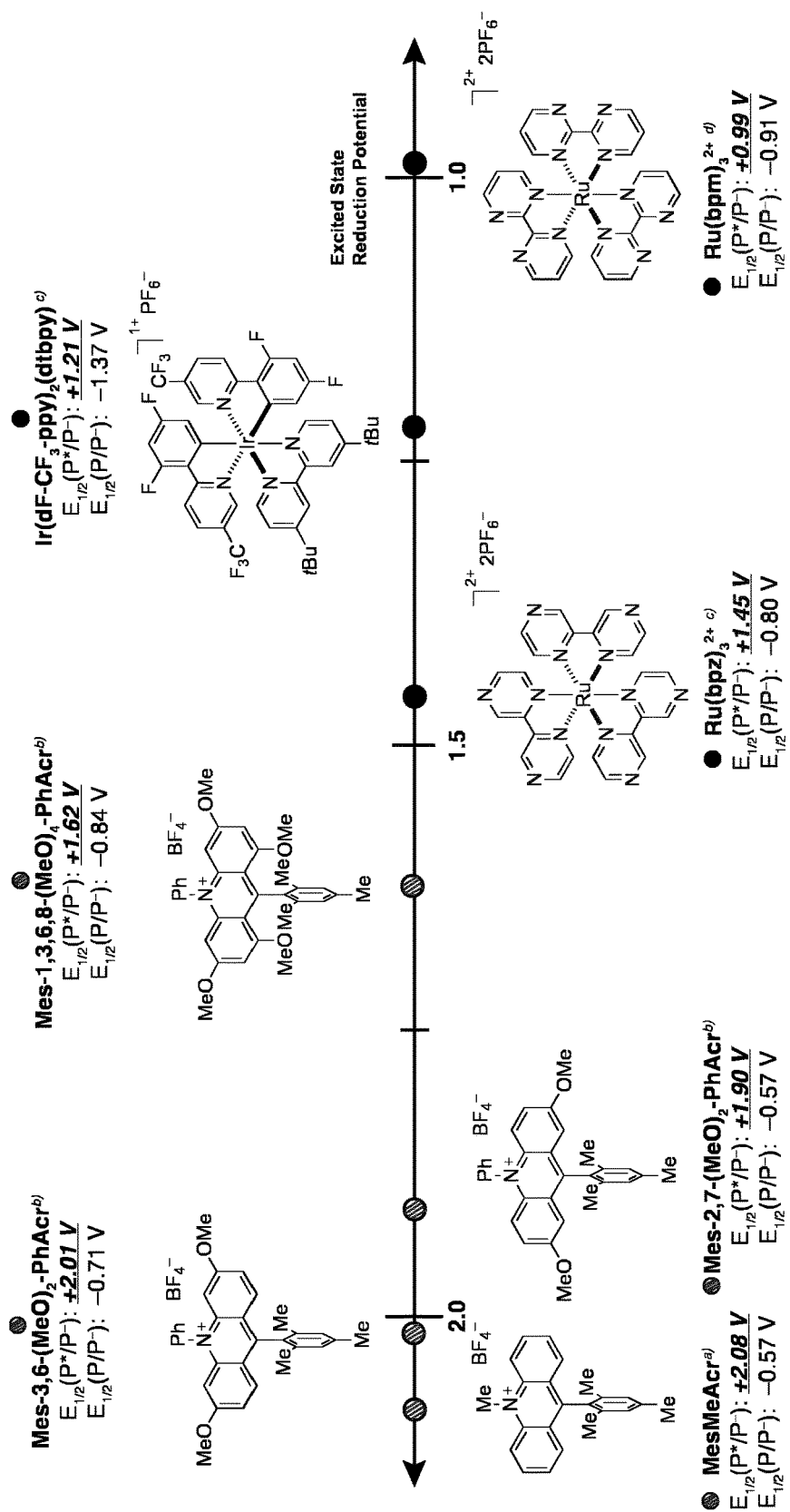
FIG. 1: Comparison of the excited state reduction potential of common organic (lined circle data points) and transition-metal based photocatalysts (full circle data points) visualize that replacement of transition-metal based photocatalysts with organic dyes is currently difficult. a) D. A. Nicewicz, et al., Chem. Rev. 2016, 116, 10075; S. Fukuzumi, et al., J. Am. Chem. Soc. 2004, 126, 1600; J. W. Verhoeven, et al., J. Am. Chem. Soc. 2005, 127, 16054. b) D. DiRocco, et al., J. Org. Chem. 2016, 81, 7244. c) J. Weaver, et al., Org. Process Res. Dev. 2016, 20, 1156. d) D. P. Rillema, et al., Inorg. Chem. 1983, 22, 1617; D. W. C. MacMillan, et al., Chem. Rev. 2013, 113, 5322.
Figure 2:
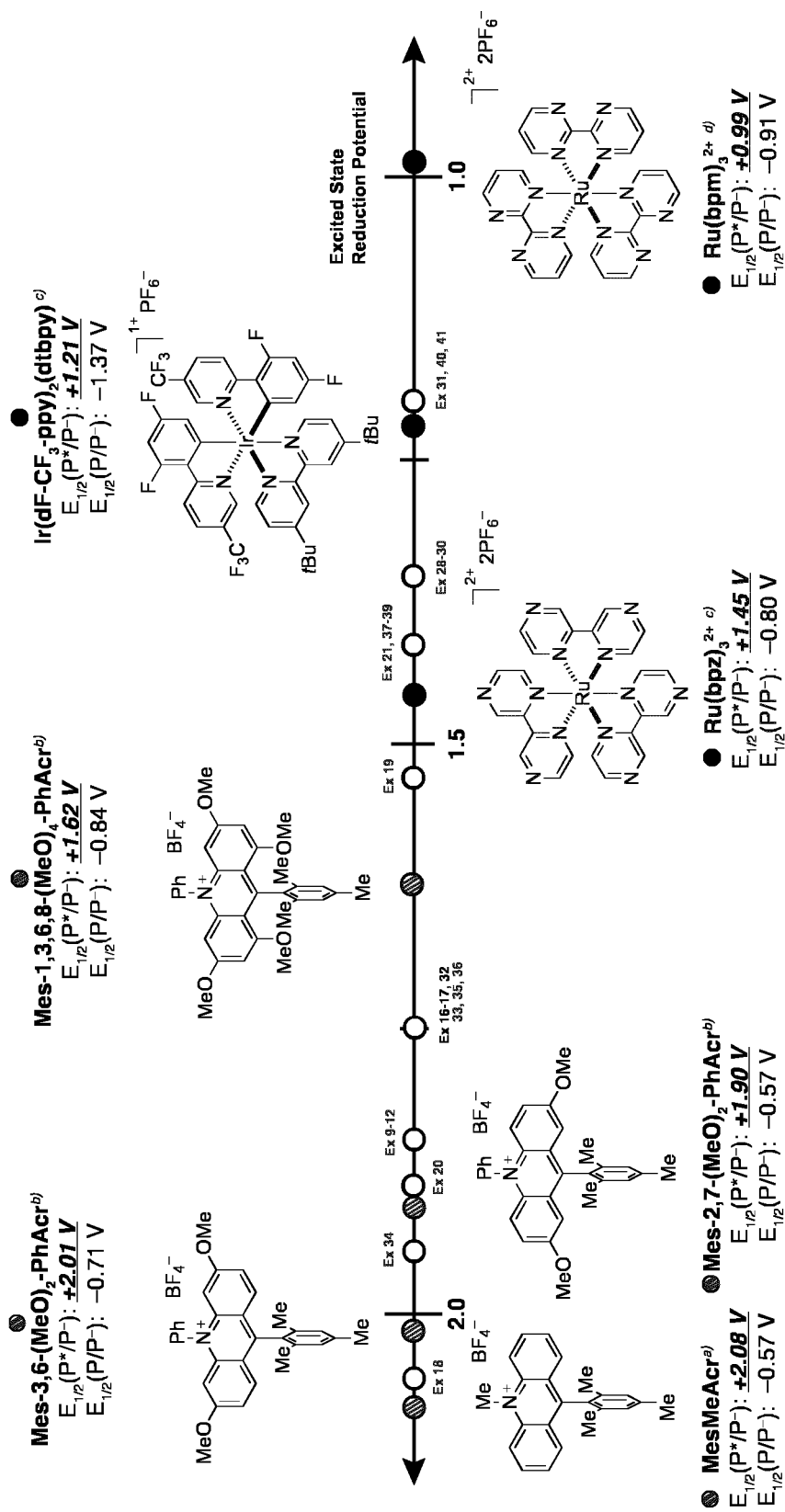
FIG. 2: The excited state reduction potential of herein described small-molecule organic dyes (empty circle data points) allows fine-tuning and extension to currently known organic dyes (lined circle data points), as well as replacement of expensive transition-metal photocatalysts (full circle data points). References a) to d) as described above for FIG. 1.

Unless defined otherwise, all technical and scientific terms used herein have the same meanings as commonly understood by one of ordinary skill in the art to which this invention belongs.

The term "Stokes shift" refers to the difference between the spectral positions of the band maxima of the absorption and luminescence arising from the same electronic transition. Currently commercial available fluoresceins and rhodamines have an average Stokes shift of 24 nm and 27 nm, respectively (Chapter 1, The Molecular Probes® Handbook, 11th Ed, 2010).

The term "excited state lifetime" refers to the time a fluorescent dye spends in the excited state before returning to the ground state by emitting a photon. The lifetime depends on the solvent. Some typical excited state lifetimes of organic fluorescent dyes are in the lower ns-range (typically <20 ns; D. DiRocco, et al., i J. Org. Chem. 2016, 81, 7244; D. A. Nicewicz, et al., Chem. Rev. 2016, 116, 10075).

The term "fluorescent dye" refers to a dye which absorbs light at a first wavelength and either emits light at second wavelength which is longer than the first wavelength or converts the absorbed energy for chemical transformations. In particular, a "fluorescent dye" is a dyestuff which exhibits the phenomenon of fluorescence.

The term "alkyl" refers to unsubstituted or halogen-substituted, linear or branched chain hydrocarbon groups having 1 to 12 carbon atoms, preferably 1 to 8 carbon atoms, more preferably 1 to 6 carbon atoms, further preferably 1 to 4 carbon atoms. Preferred alkyl groups are C1 to C4 alkyl groups, more preferably linear C1 to C4 alkyl groups, and hereby most preferably ethyl or methyl, in particular, methyl. Exemplary unsubstituted alkyl groups include methyl, ethyl, propyl, isopropyl, n-butyl, t-butyl, isobutyl, pentyl, hexyl, isohexyl, heptyl, 4,4-dimethylpentyl, octyl and the like. Halogen-substituted alkyl groups refer to alkyl groups substituted by one or more halogen. Exemplary halogen-substituted alkyl groups include methyl, ethyl, propyl, isopropyl, n-butyl, t-butyl, isobutyl, pentyl, hexyl, isohexyl, heptyl, 4,4-dimethylpentyl, octyl and the like, each independently substituted by one or more halogen preferably each independently substituted by one or more fluorine. Preferred halogen-substituted alkyl groups are substituted by one or more fluorine atomes. More preferred halogen-substituted alkyl groups are fluoromethyl, difluoromethyl, trifluoromethyl, 2-fluoroethyl, 2,2-difluoromethyl, 2,2,2-trifluoroethyl and perfluoroethyl, and in particular preferred trifluoromethyl.

The term "alkoxy" refers to alkyl-O—. The term "alkoxy" refers to the group —O-alkyl, including typically from 1 to 6 carbon atoms of a straight, branched configuration and combinations thereof attached to the parent structure through an oxygen, also referred to as C1-C6-alkoxy or O—C1-C6alkyl. Examples include, but are not limited to, methoxy, ethoxy, propoxy, isopropoxy, cyclopropyloxy and cyclohexyloxy. As described herein, alkoxy may include halogen substituted-alkoxy groups leading to haloalkoxy moieties. Preferred halogen-substituted alkoxy groups are substituted by one or more halogen, more preferably by one or more fluorine. Examples of halogen-substituted alkoxy include, but are not limited to, methoxy, ethoxy, propoxy, isopropoxy, cyclopropyloxy and cyclohexyloxy each independently substituted by one or more halogen preferably each independently substituted by one or more fluorine. More preferred halogen-substituted alkyl groups are fluoromethoxy, difluoromethoxy, trifluoromethoxy, 2-fluoroethoxy, 2,2-difluoromethoxy, 2,2,2-trifluoroethoxy and perfluoroethoxy.

The term "hydroxyalkyl" refers to an alkyl, wherein one or more carbon atoms of said alkyl carries one or two, preferably one, hydroxyl groups. A hydroxyalkyl in accordance with the present invention is not an alkoxy as defined herein, and said hydroxyalkyl is attached to the parent structure through a carbon atom.

The term "alkenyl" refers to any of the above alkyl groups having at least 2 carbon atoms, preferably 2 to 12 carbon atoms and containing one or more, typically and preferably one, carbon to carbon double bond typically and preferably at the point of attachment. Groups having 2 to 8 carbon atoms are preferred.

The term "alkynyl" refers to any of the above alkyl groups having at least two carbon atoms and containing one or more, typically and preferably one, carbon to carbon triple bond typically and preferably at the point of attachment. Groups having 2 to 8 carbon atoms are preferred.

The term "aryl" refers to an aromatic hydrocarbon group, for example, C6-10aryl, optionally substituted by one or more groups independently selected from halogen atoms, CN, $N_3$, C1-C6-alkyl, $[SO_3]^-$, $SO_3H$, $SO_2Cl$, OH, C1-C6-alkoxy, C(=O)OH and C1-C6-alkoxycarbonyl; and is preferably a mono- or polycyclic, especially monocyclic, bicyclic or tricyclic aryl moiety with 6 to 14 carbon atoms, for example 6 to 10 carbon atoms; preferably a monocyclic aryl moiety with 6 to 14 carbon atoms, for example 6 to 10 carbon atoms; more preferably an aryl moiety selected from phenyl, indenyl, indanyl, naphthyl, anthracenyl and tetracenyl; more preferably phenyl; more preferably phenyl substituted by one or more groups independently selected from halogen atoms, CN, $N_3$, C1-C6-alkyl, $[SO_3]^-$, $SO_3H$, $SO_2Cl$, OH, C1-C6-alkoxy, C(=O)OH and C1-C6-alkoxycarbonyl. Thus, the term "aryl", as used herein refers to an unsubstituted or substituted aromatic hydrocarbon group, for example, C6-10aryl, wherein said substitution of said substituted aromatic hydrocarbon group is by one or more groups independently selected from halogen atoms, CN, $N_3$, C1-C6-alkyl, $[SO_3]^-$, $SO_3H$, $SO_2Cl$, OH, C1-C6-alkoxy, C(=O)OH and C1-C6-alkoxycarbonyl. The term "heteroaryl" refers to an aromatic ring system containing at least one heteroatom, and preferably up to three heteroatoms selected from nitrogen, oxygen and sulfur as ring members, optionally substituted by one or more groups independently selected from halogen atoms, CN, $N_3$, C1-C6-alkyl, $[SO_3]^-$, $SO_3H$, $SO_2Cl$, OH, C1-C6-alkoxy, C(=O)OH and C1-C6-alkoxycarbonyl. Heteroaryl rings do not contain adjacent oxygen atoms, adjacent sulfur atoms, or adjacent oxygen and sulfur atoms within the ring. Preferred examples include pyrrolidine, piperidine, piperazine, morpholine, pyridine, pyrimidine, pyrazine, pyridazine, pyrrole, pyrazole, imidazole, triazole, isoxazole, oxazole, isothiazole, thiazole, tetrazole, furane, and thiophenyl, and further preferred are pyrrolidine, piperidine, piperazine, morpholine, pyrrole, and imidazole. Typically and preferably the term "heteroaryl" refers to an aromatic ring system consisting of one cyclic ring system containing at least one heteroatom, and preferably up to three heteroatoms selected from nitrogen, oxygen and sulfur as ring members, optionally substituted by one or more groups independently selected from halogen atoms, CN, $N_3$, C1-C6-alkyl, $[SO_3]^-$, $SO_3H$, $SO_2Cl$, OH, C1-C6-alkoxy, C(=O)OH and C1-C6-alkoxycarbonyl. Heteroaryl rings do not contain adjacent oxygen atoms, adjacent sulfur atoms, or adjacent oxygen and sulfur atoms within the ring. Preferred examples include pyrrolidine, piperidine, piperazine, morpholine, pyridine, pyrimidine, pyrazine, pyridazine, pyrrole, pyrazole, imidazole, triazole, isoxazole, oxazole, isothiazole, thiazole, tetrazole, furane, and thiophenyl, and further preferred are pyrrolidine, piperidine, piperazine, morpholine, pyrrole, and imidazole.

The term "alkoxycarbonyl" refers to alkyl-O—C(=O)—.

The term "alkylthio" refers to alkyl-S—.

The term "alkyl-aryl" refers to an aryl group bonded directly through an alkyl group, such as benzyl.

The term "alkenyl-aryl" refers to an aryl group bonded directly through an alkenyl group, such as styryl.

The term "alkanoyl" refers to alkyl-C(=O)—.

The term "aryloxy" refers to aryl-O—.

The term "O-alkyl-aryl" refers to the substituent aryl-alkyl-O—, wherein the bond to the core structure is effected by the oxygen.

The term "halogen" refers to fluorine, chlorine, bromine, or iodine.

The term "DoM" refers to directed ortho metalation.

In one aspect, the present invention provides a compound of formula (A)

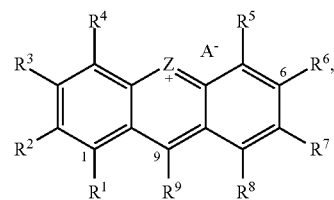

A wherein

Z is $NR^{10}$ or O;

$R^1$ is selected from C1-C6-alkoxy, aryloxy, O-alkyl-aryl, C1-C6-hydroxyalkyl, $O(CH_2)O(CH_3)$, $O(CH_2)O(CH_2)_2OCH_3$, $NH_2$, $N(H)(C1$-$C6$-alkyl), $N(C1$-$C6$-alkyl)$_2$, SH, F, $CF_3$, C1-C6-alkylthio, 4,4-dimethyl-4,5-dihydrooxazole, $NHCOR^{14}$, $NHCO_2R^{14}$, $OCNR_2$, $CONHR^{14}$, $CON(R^{14})_2$, $C=NR^{14}$, $CO_2H$, $[CO_2^-]$, $CO_2R^{14}$, $SO_3R^{14}$, $SO_3H$, $SO_2NC(CH_3)_3$, $[SO_3^-]$, $SO_2N(R^{14})_2$;

$R^2$ is selected from H, halogen, $NO_2$, CN, $NH_2$, N(H)(C1-C6-alkyl), $N(C1$-$C6$-alkyl)$_2$, OH, C1-C6-hydroxyalkyl, SH, C1-C6-alkylthio, C1-C12-alkyl, $SO_3H$, $[SO_3]$, $SO_3R^{14}$, $CO_2H$, $[CO_2]$, $CO_2R^{14}$;

R³ is selected from H, halogen, NO₂, NH₂, N(H)(C1-C6-alkyl), N(C1-C6-alkyl)₂ and CN;

R⁴ is selected from H, C1-C12-alkyl, halogen, NO₂, CN, NH₂, N(H)(C1-C6-alkyl), N(C1-C6-alkyl)₂, OH, C1-C6-alkoxy, aryloxy, O-alkyl-aryl, C1-C6-hydroxyalkyl, SH, C1-C6-alkylthio, SO₃H, [SO₃], SO₃R¹⁴;

R⁵ is selected from H, C1-C12-alkyl, halogen, NO₂, CN, NH₂, N(H)(C1-C6-alkyl), N(C1-C6-alkyl)₂, OH, C1-C6-hydroxyalkyl, SH, C1-C6-alkylthio, SO₃H, [SO₃⁻], SO₃R¹⁴;

R⁶ is selected from H, halogen, NO₂, CN, NH₂, N(H)(C1-C6-alkyl), N(C1-C6-alkyl)₂, C1-C6-hydroxyalkyl;

R⁷ is selected from H, halogen, NO₂, CN, NH₂, N(H)(C1-C6-alkyl), N(C1-C6-alkyl)₂, OH, C1-C6-alkoxy, C1-C6-hydroxyalkyl, SH, C1-C6-alkylthio, C1-C12-alkyl, SO₃H, [SO₃], SO₃R¹⁴, CO₂H, [CO₂⁻], CO₂R¹⁴;

R⁸ is selected from H, halogen, C1-C6-alkoxy, OH, C1-C6-hydroxyalkyl, O(CH₂)O(CH₃), O(CH₂)O(CH₂)₂OCH₃, NH₂, N(H)(C1-C6-alkyl), N(C1-C6-alkyl)₂, SH, F, CF₃, C1-C6-alkylthio, 4,4-dimethyl-4,5-dihydrooxazole, NHCOR¹⁴, NHCO₂R¹⁴, OCN(R¹⁴)₂, CONHR¹⁴, CON(R¹⁴)₂, C=NR¹⁴, CO₂H, [CO₂], NO₂, SO₃R¹⁴, SO₃H, SO₂NC(CH₃)₃ and SO₂N(R¹⁴)₂;

R⁹ is selected from aryl, heteroaryl, C2-C6-alkenyl-aryl, C2-C12-alkenyl, C2-C12-alkynyl, C1-C12-alkyl, NH₂, N(H)(C1-C6-alkyl), N(C1-C6-alkyl)₂, C1-C12-alkoxy, C1-C12-hydroxyalkyl, C1-C4-alkyl-C1-C4-alkyl-CO₂H, C1-C4-alkyl-CO₂-C1-C6-alkyl, C(=O)H, C(=O)-C1-C6-alkyl and C1-C12-alkylthio; and wherein said aryl and heteroaryl are optionally substituted by one or more groups independently selected from halogen atoms, CN, N₃, C1-C6-alkyl, [SO₃⁻], SO₃H, SO₂Cl, OH, C1-C6-alkoxy, CO₂⁻, C(=O)OH and C1-C6-alkoxycarbonyl, C1-C12-hydroxyalkyl, C1-C12-thioalkyl;

R¹⁰ is selected from aryl, heteroaryl, C1-C4-alkyl-aryl, C2-C6-alkenyl-aryl, C2-C12-alkenyl, C2-C12-alkynyl, C1-C12-alkyl, H, C1-C12-hydroxyalkyl, C(=O)H, C(=O)-C1-C6-alkyl, C1-C12-alkylthio, C1-C12-alkyl-CO₂H, C1-C12-alkyl-CO₂-C1-C12-alkyl, C1-C12-alkyl-CO₂-C1-C4-alkyl-aryl, O⁻, S(=O)-C1-C6-alkyl, S(=O)aryl, S(=O)-heteroaryl, S(O₂)-C1-C6-alkyl, S(O₂)-aryl, S(O₂)-heteroaryl; wherein said aryl and heteroaryl are optionally substituted by one or more groups independently selected from halogen atoms, CN, N₃, C1-C6-alkyl, [SO₃⁻], SO₃H, SO₂Cl, OH, C1-C6-alkoxy, C(=O)OH and C1-C6-alkoxycarbonyl;

R¹⁴ is selected from C1-C12-alkyl; and

A⁻ is a suitable anion preferably selected from halide ions, [BF₄]⁻, [PF₆]⁻, [ClO₄]⁻, [(C1-C5-alkyl)C(=O)O]⁻, [aryl-CH₂—C(=O)O⁻], [aryl-C(=O)O⁻], [H₂PO₄]⁻ [HSO₄]⁻ [SO₄]²⁻, [(C1-C6-alkyl)SO₃]⁻, [CF₃SO₃]⁻, aryl-CH₂–SO₃]⁻ and [aryl-SO₃]⁻, and wherein when R³ and R⁶ are independently selected from NH₂, N(H)(C1-C6-alkyl), N(C1-C6-alkyl)₂, then R⁹ is C2-C6-alkenyl-aryl, C2-C12-alkenyl, C2-C12-alkynyl, NH₂, N(H)(C1-C6-alkyl), N(C1-C6-alkyl)₂, C(=O)H, C(=O)-C1-C6-alkyl, C1-C12-alkylthio or aryl, wherein said aryl is substituted by one or more groups independently selected from C1-C6-alkyl, C1-C12-hydroxyalkyl, C1-C12-thioalkyl or N₃; and wherein when Z is NR¹⁰, R¹ and R⁸ is OMe, then R⁹ is not 2,6-dimethoxyphenyl or 4-(N(R¹⁵)₂)-2,6-dimethoxyphenyl, wherein R¹⁵ is CH₃, C₂H₅ or C₆H₁₃; and wherein when Z is O, R¹ or R⁸ is OMe, then R⁹ is not 2,6-dimethoxyphenyl; and wherein when Z is O, R¹ or R⁸ is OMe, then R⁹ is not phenyl.

In a further aspect, the present invention provides a compound of formula (A)

wherein

Z is NR¹⁰;

R¹ is selected from C1-C6-alkoxy, aryloxy, O-alkyl-aryl, C1-C6-hydroxyalkyl, O(CH₂)O(CH₃), O(CH₂)O(CH₂)₂OCH₃, NH₂, N(H)(C1-C6-alkyl), N(C1-C6-alkyl)₂, SH, F, CF₃, C1-C6-alkylthio, 4,4-dimethyl-4,5-dihydrooxazole, NHCOR¹⁴, NHCO₂R¹⁴, OCNR₂, CONHR¹⁴, CON(R¹⁴)₂, C=NR¹⁴, CO₂H, [CO₂], CO₂R¹⁴, SO₃R¹⁴, SO₃H, SO₂NC(CH₃)₃, [SO₃ ], SO₂N(R¹⁴)₂;

R² is selected from H, halogen, NO₂, CN, NH₂, N(H)(C1-C6-alkyl), N(C1-C6-alkyl)₂, OH, C1-C6-hydroxyalkyl, SH, C1-C6-alkylthio, C1-C12-alkyl, SO₃H, [SO₃⁻], SO₃R¹⁴, CO₂H, [CO₂⁻], CO₂R¹⁴;

R³ is selected from H, halogen, NO₂, NH₂, N(H)(C1-C6-alkyl), N(C1-C6-alkyl)₂ and CN;

R⁴ is selected from H, C1-C12-alkyl, halogen, NO₂, CN, NH₂, N(H)(C1-C6-alkyl), N(C1-C6-alkyl)₂, OH, C1-C6-alkoxy, aryloxy, O-alkyl-aryl, C1-C6-hydroxyalkyl, SH, C1-C6-alkylthio, SO₃H, [SO₃⁻], SO₃R¹⁴;

R⁵ is selected from H, C1-C12-alkyl, halogen, NO₂, CN, NH₂, N(H)(C1-C6-alkyl), N(C1-C6-alkyl)₂, OH, C1-C6-hydroxyalkyl, SH, C1-C6-alkylthio, SO₃H, [SO₃⁻], SO₃R¹⁴;

R⁶ is selected from H, halogen, NO₂, CN, NH₂, N(H)(C1-C6-alkyl), N(C1-C6-alkyl), C1-C6-hydroxyalkyl;

R⁷ is selected from H, halogen, NO₂, CN, NH₂, N(H)(C1-C6-alkyl), N(C1-C6-alkyl)₂, OH, C1-C6-alkoxy, C1-C6-hydroxyalkyl, SH, C1-C6-alkylthio, C1-C12-alkyl, SO₃H, [SO₃⁻], SO₃R¹⁴, CO₂H, [CO₂⁻], CO₂R¹⁴;

R⁸ is selected from H, halogen, C1-C6-alkoxy, OH, C1-C6-hydroxyalkyl, O(CH₂)O(CH₃), O(CH₂)O(CH₂)₂OCH₃, NH₂, N(H)(C1-C6-alkyl), N(C1-C6-alkyl)₂, SH, F, CF₃, C1-C6-alkylthio, 4,4-dimethyl-4,5-dihydrooxazole, NHCOR¹⁴, NHCO₂R¹⁴, OCN(R¹⁴)₂, CONHR¹⁴, CON(R¹⁴)₂, C=NR¹⁴, CO₂H, [CO₂⁻], NO₂, SO₃R¹⁴, SO₃H, SO₂NC(CH₃)₃ and SO₂N(R¹⁴)₂;

R⁹ is selected from aryl, heteroaryl, C2-C6-alkenyl-aryl, C2-C12-alkenyl, C2-C12-alkynyl, C1-C12-alkyl, NH₂, N(H)(C1-C6-alkyl), N(C1-C6-alkyl)₂, C1-C12-alkoxy, C1-C12-hydroxyalkyl, halogen, CN, N₃, C1-C4-alkyl-CO₂H, C1-C4-alkyl-CO₂-C1-C6-alkyl, C(=O)H, C(=O)-C1-C6-alkyl and C1-C12-alkylthio; and wherein said aryl and heteroaryl are optionally substituted by one or more groups independently selected from halogen atoms, CN, N₃, C1-C6-alkyl, [SO₃⁻], SO₃H, SO₂Cl, OH, C1-C6-alkoxy, CO₂⁻, C(=O)OH and C1-C6-alkoxycarbonyl, C1-C12-hydroxyalkyl, C1-C12-thioalkyl;

R¹⁰ is selected from aryl, heteroaryl, C1-C4-alkyl-aryl, C2-C6-alkenyl-aryl, C2-C12-alkenyl, C2-C12-alkynyl, C1-C12-alkyl, H, C1-C12-hydroxyalkyl, C(=O)H, C(=O)-C1-C6-alkyl, C1-C12-alkylthio, C1-C12-alkyl-CO₂H, C1-C12-alkyl-CO₂—C1-C12-alkyl, C1-C12-alkyl-CO₂—C1-C4-alkyl-aryl, O⁻, S(=O)—C1-C6-alkyl, S(=O)aryl, S(=O)-heteroaryl, S(O₂)—C1-C6-alkyl, S(O₂)-aryl, S(O₂)-heteroaryl; wherein said aryl and heteroaryl are optionally substituted by one or more groups independently selected from halogen atoms, CN, N₃, C1-C6-alkyl, [SO₃⁻], SO₃H, SO₂Cl₅ OH, C1-C6-alkoxy, C(=O)OH and C1-C6-alkoxycarbonyl;

R¹⁴ is selected from C1-C12-alkyl; and

A⁻ is a suitable anion preferably selected from halide ions, [BE]⁻, [PF₆]⁻, [ClO₄]⁻, [(C1-C5-alkyl)C(=O)O]⁻, [aryl-CH₂—C(=O)O]⁻, [aryl-C(=O)O]⁻, [H₂PO₄]⁻ [HSO₄]⁻ [SO₄]²⁻, [(C1-C6-alkyl)SO₃]⁻, [CF₃SO₃]⁻, aryl-CH₂—SO₃]⁻ and [aryl-SO₃]⁻, and wherein when R³ and R⁶ are independently selected from NH₂, N(H)(C1-C6-alkyl), N(C1-C6-alkyl)₂, then R⁹ is C2-C6-alkenyl-aryl, C2-C12-alkenyl, C2-C12-alkynyl, NH₂, N(H)(C1-C6-alkyl), N(C1-C6-alkyl)₂, C(=O)H, C(=O)-C1-C6-alkyl, C1-C12-alkylthio, heteroaryl or aryl, wherein said heteroaryl or aryl is optionally substituted by one or more groups independently selected from C1-C6-alkyl, C1-C1 2-hydroxyalkyl, C1-C12-thioalkyl or N₃; and wherein when R¹ and R⁸ is OMe, and R², R³, R⁴, R⁵, R⁶, and R⁷ are H, then R⁹ is not 2,6-dimethoxyphenyl or 4-(N(R¹⁵)₂)-2,6-dimethoxyphenyl, wherein R¹⁵ is CH₃, C₂H₅ or C₆H₁₃.

In a further aspect, the present invention provides a compound of formula (A)

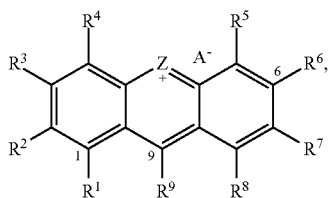

A wherein

Z is NR¹⁹ or O;

R¹ is selected from C1-C6-alkoxy, aryloxy, O-alkyl-aryl, C1-C6-hydroxyalkyl, O(CH₂)O(CH₃), O(CH₂)O(CH₂)₂OCH₃, NH₂, N(H)(C1-C6-alkyl), N(C1-C6-alkyl)₂, SH, F, CF₃, C1-C6-alkylthio, 4,4-dimethyl-4,5-dihydrooxazole, NHCOR¹⁴, NHCO₂R¹⁴, OCNR₂, CONHR¹⁴, CON(R¹⁴)₂, C=NR¹⁴, CO₂H, [CO₂⁻], CO₂R¹⁴, SO₃R¹⁴, SO₃H, SO₂NC(CH₃)₃, [SO₃ ], SO₂N(R¹⁴)₂;

R² is selected from H, halogen, NO₂, CN, NH₂, N(H)(C1-C6-alkyl), N(C1-C6-alkyl)₂, OH, C1-C6-hydroxyalkyl, SH, C1-C6-alkylthio, C1-C12-alkyl, SO₃H, [SO₃⁻], SO₃R¹⁴, CO₂H, [CO₂], CO₂R¹⁴;

R³ is selected from H, halogen, NO₂, NH₂, N(H)(C1-C6-alkyl), N(C1-C6-alkyl)₂ and CN;

R⁴ is selected from H, C1-C12-alkyl, halogen, NO₂, CN, NH₂, N(H)(C1-C6-alkyl), N(C1-C6-alkyl)₂, OH, C1-C6-alkoxy, aryloxy, O-alkyl-aryl, C1-C6-hydroxyalkyl, SH, C1-C6-alkylthio, SO₃H, [SO₃⁻], SO₃R¹⁴;

R⁵ is selected from H, C1-C12-alkyl, halogen, NO₂, CN, NH₂, N(H)(C1-C6-alkyl), N(C1-C6-alkyl)₂, OH, C1-C6-hydroxyalkyl, SH, C1-C6-alkylthio, SO₃H, [SO₃⁻], SO₃R¹⁴;

R⁶ is selected from H, halogen, NO₂, CN, NH₂, N(H)(C1-C6-alkyl), N(C1-C6-alkyl)₂, C1-C6-hydroxyalkyl;

R⁷ is selected from H, halogen, NO₂, CN, NH₂, N(H)(C1-C6-alkyl), N(C1-C6-alkyl)₂, OH, C1-C6-alkoxy, C1-C6-hydroxyalkyl, SH, C1-C6-alkylthio, C1-C12-alkyl, SO₃H, [SO₃], SO₃R¹⁴, CO₂H, [CO₂⁻], CO₂R¹⁴;

R⁸ is selected from H, halogen, C1-C6-alkoxy, OH, C1-C6-hydroxyalkyl, O(CH₂)O(CH₃), O(CH₂)O(CH₂)₂OCH₃, NH₂, N(H)(C1-C6-alkyl), N(C1-C6-alkyl)₂, SH, F, CF₃, C1-C6-alkylthio, 4,4-dimethyl-4,5-dihydrooxazole, NHCOR¹⁴, NHCO₂R¹⁴, OCN(R¹⁴)₂, CONHR¹⁴, CON(R¹⁴)₂, C=NR¹⁴, CO₂H, [CO₂⁻], NO₂, SO₃R¹⁴, SO₃H, SO₂NC(CH₃)₃ and SO₂N(R¹⁴)₂;

R⁹ is selected from aryl, heteroaryl, C2-C6-alkenyl-aryl, C2-C12-alkenyl, C2-C12-alkynyl, C1-C12-alkyl, NH₂, N(H)(C1-C6-alkyl), N(C1-C6-alkyl)₂, C1-C12-alkoxy, C1-C12-hydroxyalkyl, halogen, CN, N₃, C1-C4-alkyl-CO₂H, C1-C4-alkyl-CO₂-C1-C6-alkyl, C(=O)H, C(=O)—C1-C6-alkyl and C1-C12-alkylthio; and wherein said aryl and heteroaryl are optionally substituted by one or more groups independently selected from halogen atoms, CN, N₃, C1-C6-alkyl, [SO₃], SO₃H, SO₂Cl₅ OH, C1-C6-alkoxy, CO₂⁻, C(=O)OH and C1-C6-alkoxycarbonyl, C1-C12-hydroxyalkyl, C1-C12-thioalkyl;

R¹⁰ is selected from aryl, heteroaryl, C1-C4-alkyl-aryl, C2-C6-alkenyl-aryl, C2-C12-alkenyl, C2-C12-alkynyl, C1-C12-alkyl, H, C1-C12-hydroxyalkyl, C(=O)H, C(=O)-C1-C6-alkyl, C1-C12-alkylthio ₅ C1-C12-alkyl-CO₂H, C1-C12-alkyl-CO₂—C1-C12-alkyl, C1-C12-alkyl-CO₂-C1-C4-alkyl-aryl, O⁻, S(=O)—C1-C6-alkyl, S(=O) aryl, S(=O)-heteroaryl, S(O₂)-C1-C6-alkyl, S(O₂)-aryl, S(O₂)-heteroaryl; wherein said aryl and heteroaryl are optionally substituted by one or more groups independently selected from halogen atoms, CN, N₃, C1-C6-alkyl, [SO₃]⁻, SO₃H, SO₂Cl, OH, C1-C6-alkoxy, C(=O)OH and C1-C6-alkoxycarbonyl;

R¹⁴ is selected from C1-C12-alkyl; and

A⁻ is a suitable anion preferably selected from halide ions, [BF₄]⁻, [PF₆]⁻, [ClO₄]⁻, [(C1-C5-alkyl)C(=O)O]⁻, [aryl-CH₂—C(=O)O]⁻, [aryl-C(=O)O]⁻, [H₂PO₄]⁻ [HSO₄]⁻ [SO₄]²⁻, [(C1-C6-alkyl)SO₃]⁻, [CF₃SO₃]⁻, aryl-CH₂—SO₃]⁻ and [aryl-SO₃]⁻, and wherein when R³ and R⁶ are independently selected from NH₂, N(H)(C1-C6-alkyl), N(C1-C6-alkyl)₂, then R⁹ is C2-C6-alkenyl-aryl, C2-C12-alkenyl, C2-C12-alkynyl, NH₂, N(H)(C1-C6-alkyl), N(C1-C6-alkyl)₂, C(=O)H, C(=O)-C1-C6-alkyl, C1-C12-alkylthio or aryl, wherein said aryl is substituted by one or more groups independently selected from C1-C6-alkyl, C1-C12-hydroxyalkyl, C1-C12-thioalkyl or N₃; and wherein when Z is NR¹⁰, R¹ and R⁸ is OMe, then R⁹ is not 2,6-dimethoxyphenyl or 4-(N(R¹⁵)₂)-2,6-dimethoxyphenyl, wherein R¹⁵ is CH₃, C₂H₅ or C₆H₁₃; and wherein when Z is O, R¹ or R⁸ is OMe, then R⁹ is not 2,6-dimethoxyphenyl; and wherein when Z is O, R¹ or R⁸ is OMe, then R⁹ is not phenyl.

In a preferred embodiment, said Z is NR¹⁰.

In a further preferred embodiment, said Z is O.

In a further preferred embodiment, said Z is O leading to xanthylium salts. Preferred embodiments of the xanthylium salts of the present invention, in particular, the inventive 1,6,9-substituted xanthylium salts were found to have a significantly increased Stokes shift compared to previous substitution patterns. Typically, 3,6,9-substituted xanthylium fluorophores have a Stokes shift of about 30 nm (Chapter 1, The Molecular Probes® Handbook, 11th Ed, 2010). Fluorophores with small Stokes shifts suffer from various drawbacks in sensing and imaging techniques such as fluorescence detection errors due to excitation backscattering effects, self-quenching by energy transfer and low signal fidelity (R. T. Raines, et al., *ACS Chem. Biol.* 2008, 3, 142; W. Zhu, et al., *J. Am. Chem. Soc.* 2014, 136, 3579; W. Lin, et al., *Angew. Chem. Int. Ed.* 2010, 49, 375). Whereas larger Stokes shifts proved to be beneficial (Chapter 1, The Molecular Probes® Handbook, 11th Ed, 2010;), the achievement of such larger Stokes shifts typically require dual-fluorescent dye systems based on through-bond energy transfer (TBET) or fluorescence resonance energy transfer (FRET) (K. Burgess, et al., *J. Am. Chem. Soc.* 2003, 125, 14668; W. Lin, et al., *Angew. Chem. Int. Ed.* 2010, 49, 375).

In a further preferred embodiment, said $R^9$ is selected from phenyl, indenyl, indanyl, naphthyl, anthracenyl and tetracenyl, each independently optionally substituted by one, two or three groups independently selected from halogen atoms, CN, $N_3$, C1-C6-alkyl, $[SO_3]$, $SO_3H$, $SO_2Cl$, OH, C1-C6-alkoxy, $CO_2^-$, $C(=O)OH$, C1-C8-hydroxyalkyl, C1-C8-thioalkyl and C1-C6-alkoxycarbonyl.

In a further embodiment, $R^9$ is aryl or heteroaryl, wherein said aryl and heteroaryl are optionally substituted with 1 to 6, 1 to 5, 1 to 4, 1 to 3 or 1 to 2 substituents which are independently at each occurrence halogen, $[SO_3]$, $SO_3H$, $SO_2Cl$, OH, C1-C6-alkoxy, $C(=O)OH$ or C1-C6-alkoxycarbonyl.

In a preferred embodiment, said $R^9$ is selected from phenyl, indenyl, indanyl, naphthyl, anthracenyl and tetracenyl, each independently optionally substituted by one, two or three groups independently selected from halogen atoms, CN, $N_3$, C1-C4-alkyl, $[SO_3]^-$, $SO_3H$, $SO_2Cl$, OH, C1-C4-alkoxy, $CO_2^-$, $C(=O)OH$, C1-C6-hydroxyalkyl, C1-C6-thioalkyl and C1-C4-alkoxycarbonyl.

In a preferred embodiment, said $R^9$ is selected from phenyl, indenyl, indanyl and naphthyl, each independently optionally substituted by one, two or three groups independently selected from halogen atoms, CN, $N_3$, C1-C4-alkyl, $[SO_3]^-$, $SO_3H$, $SO_2Cl$, OH, C1-C4-alkoxy, $CO_2^-$, $C(=O)OH$, C1-C4-hydroxyalkyl, C1-C4-thio alkyl and C1-C4-alkoxycarbonyl.

In a further preferred embodiment, said $R^9$ is selected from phenyl and naphthyl, each independently optionally substituted by one, two or three groups independently selected from halogen atoms, CN, $N_3$, C1-C4-alkyl, $[SO_3]^-$, $SO_3H$, $SO_2Cl$, OH, C1-C4-alkoxy, $CO_2^-$, $C(=O)OH$, C1-C4-hydroxyalkyl, C1-C4-thio alkyl and C1-C4-alkoxycarbonyl.

In a further preferred embodiment, said $R^9$ is selected from phenyl, indenyl, indanyl and naphthyl, each independently optionally substituted by one, two or three groups independently selected from F, Cl, Br, CN, C1-C4-alkyl, $CO_2^-$, $CO_2H$, $[SO_3]^-$, $SO_3H$, OH, C1-C4-alkoxy and C1-C4-thioalkyl.

In a further embodiment, $R^9$ is phenyl, indenyl, indanyl, naphthyl, anthracenyl, tetracenyl, C1-C4-alkyl-aryl, C2-C6-alkenyl-aryl, C2-C12-alkenyl, C2-C12-alkynyl or C1-C12-alkyl; wherein said phenyl, indenyl, indanyl, naphthyl, anthracenyl and said tetracenyl are optionally substituted by one or more groups independently selected from halogen atoms, CN, $N_3$, C1-C6-alkyl, $[SO_3]^-$, $SO_3H$, $SO_2Cl$, OH, C1-C6-alkoxy, $C(=O)OH$ and C1-C6-alkoxycarbonyl.

In a further embodiment, $R^9$ is phenyl, indenyl, indanyl, naphthyl, anthracenyl or tetracenyl, each independently optionally substituted by one, two or three groups independently selected from halogen atoms, CN, $N_3$, C1-C6-alkyl, $[SO_3]^-$, $SO_3H$, $SO_2Cl$, OH, C1-C6-alkoxy, $C(=O)OH$ and C1-C6-alkoxycarbonyl.

In a further embodiment, $R^9$ is phenyl, indenyl, indanyl, naphthyl, anthracenyl or tetracenyl, each independently optionally substituted by one, two or three groups independently selected from halogen atoms, C1-C4-alkyl, $[SO_3]^-$, $SO_3H$, $SO_2Cl$, OH, C1-C4-alkoxy, $C(=O)OH$ and C1-C4-alkoxycarbonyl.

In a further embodiment, $R^9$ is phenyl, naphthyl or anthracenyl, each independently optionally substituted by one, two or three groups independently selected from halogen atoms, CN, $N_3$, C1-C6-alkyl, $[SO_3]^-$, $SO_3H$, $SO_2Cl$, OH, C1-C6-alkoxy, $C(=O)OH$ and C1-C6-alkoxycarbonyl.

In a further embodiment, $R^9$ is phenyl, naphthyl or anthracenyl, each independently optionally substituted by one, two or three groups independently selected from halogen atoms, C1-C4-alkyl, $[SO_3]^-$, $SO_3H$, $SO_2Cl$, OH, C1-C4-alkoxy, $C(=O)OH$ and C1-C4-alkoxycarbonyl.

In a further preferred embodiment, said $R^9$ is selected from phenyl, indenyl, indanyl and naphthyl, each independently optionally substituted by one, two or three groups independently selected from F, Cl, CN, $CO_2$, $S_3$, $CO_2H$, $SO_3H$, C1-C4-alkyl, C1-C4-alkoxy and C1-C4- thioalkyl.

In a further preferred embodiment, said $R^9$ is selected from phenyl and naphthyl, optionally substituted by one, two or three groups independently selected from F, Cl, CN, $CO_2^-$, $S_3^-$, $CO_2H$, $SO_3H$, C1-C4-alkyl, C1-C4-alkoxy and C1-C4-thioalkyl.

In a preferred embodiment, $R^9$ is phenyl or naphthyl, each independently optionally substituted by one, two or three groups independently selected from halogen atoms, C1-C4-alkyl, $[SO_3]^-$, $SO_3H$, $SO_2Cl$, C1-C4-alkoxy, $C(=O)OH$ and C1-C4-alkoxycarbonyl.

In a further preferred embodiment, said $R^9$ is phenyl, optionally substituted by one, two or three groups independently selected from F, Cl, CN, C1-C4-alkyl, $CO_2^-$, $SO_3^-$, $CO_2H$, $SO_3H$, C1-C4-thioalkyl and C1-C4-alkoxy, wherein preferably said optional substitution is at the 2, 4 and/or 6-position of said phenyl.

In a further preferred embodiment, $R^9$ is phenyl, optionally substituted by one, two or three groups independently selected from halogen atoms, C1-C4-alkyl, $[SO_3]^-$, $SO_3H$, $SO_2Cl$, OH, C1-C4-alkoxy, $C(=O)OH$ and C1-C4-alkoxycarbonyl.

In a further preferred embodiment, $R^9$ is phenyl, optionally substituted by one, two or three groups independently selected from halogen atoms, C1-C4-alkyl, $[SO_3]^-$, $SO_3H$, $SO_2Cl$, OH, C1-C4-alkoxy, $C(=O)OH$ and C1-C4-alkoxycarbonyl, wherein said optional substitution is at the para and/or ortho position of said phenyl.

In a further preferred embodiment, $R^9$ is phenyl, optionally substituted by one, two or three groups independently selected from halogen atoms, wherein said optional substitution is at the para and/or ortho position of said phenyl.

In a further preferred embodiment, $R^9$ is phenyl, optionally substituted by one group selected from halogen atoms, C1-C4-alkyl, $[SO_3]^-$, $SO_3H$, $SO_2Cl$, OH, C1-C4-alkoxy, $C(=O)OH$ and C1-C4-alkoxycarbonyl, wherein said optional substitution is at the para or ortho position of said phenyl, preferably at the para position of said phenyl.

In a further preferred embodiment, $R^9$ is phenyl, optionally substituted by one group selected from halogen atoms, preferably by fluorine or chlorine, wherein said optional substitution is at the para or ortho position of said phenyl, preferably at the para position of said phenyl.

In a further preferred embodiment, said $R^9$ is phenyl substituted by one, two or three groups independently selected from C1-C4-alkyl, $CO_2^-$, $S_3$, $CO_2H$, $SO_3H$, C1-C4-thioalkyl and C1-C4-alkoxy, wherein one of said substitution of said $CO_2^-$, $SO_3^-$, $CO_2H$, $SO_3H$, C1-C4-thioalkyl and C1-C4-alkoxy is at the 2-position of said phenyl.

In a further preferred embodiment, said $R^9$ is selected from phenyl, indenyl, indanyl and naphthyl, each independently optionally substituted by one, two or three groups independently selected from F, Cl, CN, methyl, methoxy, $CO_2^-$, $SO_3^-$, $CO_2H$, $SO_3H$, $CH_2OH$, $CH_2SH$.

In a further preferred embodiment, said $R^9$ is selected from phenyl and naphthyl, optionally substituted by one, two or three groups independently selected from F, Cl, CN, methyl, methoxy, $CO_2^-$, $SO_3^-$, $CO_2H$, $SO_3H$, $CH_2OH$ and $CH_2SH$.

In a further preferred embodiment, said $R^9$ is phenyl, optionally substituted by one, two or three groups independently selected from F, Cl, CN, methyl, methoxy, $CO_2^-$, $S_3$, $CO_2H$, $SO_3H$, $CH_2OH$ and $CH_2SH$, wherein preferably said optional substitution is at the 2, 4 and/or 6-position of said phenyl.

In a further preferred embodiment, said $R^9$ is selected from phenyl and naphthyl, optionally substituted by one, two or three F, Cl, methyl, methoxy, $CO_2^-$, $S_3$, $CO_2H$, $SO_3H$, $CH_2OH$ and $CH_2SH$.

In a further preferred embodiment, said $R^9$ is phenyl optionally substituted by one, two or three groups independently selected from C1-C4-alkyl, $CO_2^-$, $S_3$, $CO_2H$, $SO_3H$, C1-C4-hydroxyalkyl, C1-C4-thioalkyl and C1-C4-alkoxy, wherein one of said substitution of said $CO_2^-$, $SO_3^-$, $CO_2H$, $SO_3H$, C1-C12-hydroxyalkyl, C1-C12-thioalkyl and C1-C4-alkoxy is at the 2-position of said phenyl.

In a further preferred embodiment, said $R^9$ is phenyl substituted by one, two or three groups independently selected from C1-C4-alkyl, $CO_2^-$, $SO_3^-$, $CO_2H$, $SO_3H$, C1-C4-hydroxyalkyl, C1-C4-thioalkyl and C1-C4-alkoxy, wherein one of said substitution of said $CO_2^-$, $SO_3^-$, $CO_2H$, $SO_3H$, C1-C4-hydroxyalkyl, C1-C4-thioalkyl and C1-C4-alkoxy is at the 2-position of said phenyl.

In a further very preferred embodiment, $R^9$ is unsubstituted naphthyl. In a further preferred embodiment, $R^9$ is naphthyl optionally substituted with 1 to 7, 1 to 6, 1 to 5, 1 to 4, 1 to 3 or 1 to 2 substituents which are independently at each occurrence halogen, $[SO_3]^-$, $SO_3H$, $SO_2Cl$, OH, C1-C6-alkoxy, C(=O)OH or C1-C6-alkoxycarbonyl.

In a further preferred embodiment, said $R^9$ is selected from phenyl and naphthyl, optionally substituted by one, two or three methyl or methoxy. In a further preferred embodiment, said $R^9$ is selected from phenyl optionally substituted by one, two or three methyl or methoxy. In a further preferred embodiment, said $R^9$ is selected from phenyl and naphthyl, substituted by one, two or three methyl or methoxy. In a further preferred embodiment, said $R^9$ is selected from phenyl substituted by one, two or three methyl or methoxy. In a further preferred embodiment, $R^9$ is 4-(chlorosulfonyl)-2-sulfophenyl. In a further preferred embodiment, $R^9$ is 2-carboxyphenyl. In one embodiment, $R^9$ is 2-(ethoxycarbonyl)phenyl.

In a further very preferred embodiment, said $R^9$ is selected from aryl, heteroaryl, C1-C12-alkyl, C2-C6-alkenyl-aryl; and wherein said aryl and heteroaryl are optionally substituted by one or more groups independently selected from halogen atoms, CN, C1-C6-alkyl, $[SO_3]^-$, $SO_3H$, $SO_2Cl$, OH, C1-C6-alkoxy, $CO_2^-$, C(=O)OH and C1-C6-alkoxycarbonyl, C1-C12-hydroxyalkyl, C1-C12-thio alkyl.

In a further very preferred embodiment, said $R^9$ is aryl; and wherein said aryl and heteroaryl are optionally substituted by one or more groups independently selected from halogen atoms, CN, C1-C6-alkyl, $[SO_3]^-$, $SO_3H$, $SO_2Cl$, OH, C1-C6-alkoxy, $CO_2^-$, C(=O)OH and C1-C6-alkoxycarbonyl, C1-C12-hydroxyalkyl, C1-C12-thio alkyl.

In a further very preferred embodiment, said $R^9$ is naphthyl. In a further very preferred embodiment, said $R^9$ is phenyl. In a further very preferred embodiment, said $R^9$ is selected from phenyl, naphthyl, 4-methylphenyl. 2,6-dimethylphenyl, and 2,4,6-trimethylphenyl. In a further very preferred embodiment, said $R^9$ is selected from phenyl, 4-methylphenyl, 2,6-dimethylphenyl, and 2,4,6-trimethylphenyl. In a further very preferred embodiment, said $R^9$ is 4-methylphenyl. In a further very preferred embodiment, said $R^9$ is 4-flurophenyl. In a further very preferred embodiment, said $R^9$ is 4-methoxyphenyl. In a very further preferred embodiment, said $R^9$ is 2,6-dimethylphenyl. In a further preferred embodiment, said $R^9$ is 2,6-dimethoyphenyl. In a further very preferred embodiment, said $R^9$ is 2,4,6-trimethylphenyl. In a further preferred embodiment, said $R^9$ is 2,4,6-trimethoxyphenyl.

In a further very preferred embodiment, said $R^4$ is selected from H, $NH_2$, N(H)(C1-C6-alkyl), $N(C1-C6-alkyl)_2$, halogen, $NO_2$, $SO_3H$, $[SO_3]$, and $SO_3R^{14}$.

In a further very preferred embodiment, said $R^4$ is H.

In a further very preferred embodiment, said $R^4$ is selected from H, halogen, $NO_2$, $SO_3H$, $[SO_3^-]$, $SO_3R^{14}$.

In a further preferred embodiment, said $R^4$ is selected from H, $NH_2$, N(H)(C1-C6-alkyl), $N(C1-C6-alkyl)_2$. In a further preferred embodiment, said $R^4$ is selected from $NMe_2$ or $NEt_2$.

In a further preferred embodiment, said $R^5$ is selected from H, C1-C12-alkyl, halogen, $NO_2$, CN, $NH_2$, N(H)(C1-C6-alkyl), $N(C1-C6-alkyl)_2$, OH, C1-C6-hydroxyalkyl, SH, C1-C6-alkylthio, $SO_3H$, $[SO_3^-]$, C1-C6-alkylthio, $SO_3R^{14}$.

In a further very preferred embodiment, said $R^5$ is selected from H, $NH_2$, N(H)(C1-C6-alkyl), $N(C1-C6-alkyl)_2$, halogen, $NO_2$, $SO_3H$, $[SO_3]$, and $SO_3R^{14}$.

In a further very preferred embodiment, said $R^5$ is H.

In a further very preferred embodiment, said $R^5$ is selected from H, halogen, $NO_2$, $SO_3H$, $[SO_3^-]$, $SO_3R^{14}$.

In a further preferred embodiment, said $R^5$ is selected from H, $NH_2$, N(H)(C1-C6-alkyl), $N(C1-C6-alkyl)_2$. In a further preferred embodiment, said $R^5$ is selected from H, $NH_2$, N(H)(C1-C6-alkyl), $N(C1-C6-alkyl)_2$. In a further preferred embodiment, said $R^4$ is selected from $NMe_2$ or $NEt_2$.

In a further preferred embodiment, said $R^7$ is selected from H, halogen, $NO_2$, CN, $NH_2$, N(H)(C1-C6-alkyl), $N(C1-C6-alkyl)_2$, OH, C1-C6-hydroxyalkyl, SH, C1-C6-alkylthio, C1-C12-alkyl, $SO_3H$, $[SO_3^-]$, $SO_3R^{14}$, $CO_2H$ and $CO_2R^{14}$.

In a further very preferred embodiment, said $R^7$ is selected from H, $NH_2$, N(H)(C1-C6-alkyl), $N(C1-C6-alkyl)_2$, C1-C6-alkoxy.

In a further very preferred embodiment, said $R^7$ is selected from H, $NMe_2$ or $NEt_2$.

In a further very preferred embodiment, said $R^7$ is H.
In a further very preferred embodiment, said $R^7$ is $NMe_2$.
In a further very preferred embodiment, said $R^7$ is $NEt_2$.

In a further preferred embodiment, each of $R^2$, $R^3$, $R^4$, $R^5$ and $R^7$ is independently selected from H, halogen, $NO_2$, CN, C1-C4-alkyl, OH and C1-C4-alkoxy.

In a further preferred embodiment, each of $R^2$, $R^3$, $R^4$, $R^5$ and $R^7$ is independently selected from H, halogen, C1-C4-alkyl, OH and C1-C4-alkoxy.

In a further preferred embodiment, each of $R^2$, $R^3$, $R^4$, $R^5$ and $R^7$ is independently selected from H and halogen. Preferably, said halogen is selected from fluorine, chlorine, bromine and iodine.

In a further preferred embodiment, each of $R^2$, $R^3$, $R^4$, $R^5$ and $R^7$ is independently selected from H and $NO_2$.

In a further preferred embodiment, each of $R^2$, $R^3$, $R^4$, $R^5$ and $R^7$ is independently selected from H and CN.

In a further preferred embodiment, each of $R^2$, $R^3$, $R^4$, $R^5$ and $R^7$ is independently selected from H and C1-C6-alkyl. Preferably, said C1-C6-alkyl is a C1-C5-alkyl, more preferably a C1-C4-alkyl, more preferably a C1-C3-alkyl, more preferably ethyl or methyl, most preferably methyl.

In a further preferred embodiment, each of $R^2$, $R^3$, $R^4$, $R^5$ and $R^7$ is independently selected from H and C1-C6-alkoxy, preferably C1-05-alkoxy, more preferably C1-C4-alkoxy, more preferably C1-C3-alkoxy, more preferably ethoxy or methoxy, most preferably methoxy.

In a further preferred embodiment, said $R^2$, $R^3$, $R^4$, $R^5$ and $R^7$ are each H.

In a further preferred embodiment, said $R^3$ and $R^6$ are independently selected from H, halogen, $NO_2$, CN, $NH_2$, N(H)(C1-C6-alkyl), $N(C1-C6-alkyl)_2$. In a further preferred embodiment, said $R^3$ and $R^6$ are independently selected from H, halogen, CN, $NH_2$, N(H)(C1-C6-alkyl), and $N(C1-C6-alkyl)_2$. In a further preferred embodiment, said $R^6$ is selected from H, halogen, $NO_2$, CN, $NH_2$, N(H)(C1-C6-alkyl), and $N(C1-C6-alkyl)_2$. In a further preferred embodiment, said $R^3$ and $R^6$ are independently selected from H, halogen, $NH_2$, N(H)(C1-C6-alkyl), and $N(C1-C6-alkyl)_2$.

In a further preferred embodiment, said $R^3$ and $R^6$ are independently selected from H, $NH_2$, N(H)(C1-C6-alkyl) or $N(C1-C6-alkyl)_2$.

In a further preferred embodiment, said $R^3$ and $R^6$ are independently selected from H, $NH_2$, N(H)(C1-C6-alkyl), and $N(C1-C6-alkyl)_2$. In a further preferred embodiment, said $R^3$ and $R^6$ are independently selected from H, $NH_2$, N(H)(C1-C4-alkyl), and $N(C1-C4-alkyl)_2$. In a further preferred embodiment, said $R^3$ and $R^6$ are independently selected from H, $NH_2$, N(H)(C1-C2-alkyl), and $N(C1-C2-alkyl)_2$. In a further preferred embodiment, said $R^3$ and $R^6$ are independently selected from H, $NH_2$, $N(H)(C_2H_5)$, and $N(C_2H_5)_2$. In a further preferred embodiment, said $R^3$ and $R^6$ are independently selected from H, $NH_2$, N(H)(Me), and $N(Me)_2$.

Recently published results by the inventors (C. Span, et al. *Angew. Chem. Int. Ed.* 2018, 57, 2436) on 3,6-bis(dimethylamino)-9-mesityl-10-methylacridinium bromide salt (previously synthesized by J. Yanke et al., CN103980882) showed, that substitution of the heterocyclic core with amino functionalities such as $N(Me)_2$ at both $R^3$ and $R^6$ significantly lowers both ground and excited state reduction potential, compared to the highly oxidative 9-mesityl-10-methylacridinium salts. The preferred inventive compounds having an analogous substitution at R', $R^6$ and $R^9$ and having further substitution at $R^1$ and $R^8$ in accordance with the invention and the preferred embodiments of its $R^1$ and $R^8$ substitution, already provides significantly extended redox windows. The aforementioned recently published results make it plausible that an additional substitution at $R^3$ preferably with amino functionalities such as $N(Me)_2$ leads to even more extensive redox windows and, in particular, to even more lower reductive potentials.

Thus, In a further preferred embodiment, said $R^3$ and $R^6$ are independently selected from $NH_2$, N(H)(C1-C6-alkyl), and $N(C1-C6-alkyl)_2$. In a further preferred embodiment, said $R^3$ and $R^6$ are independently selected from $NH_2$, N(H)(C1-C4-alkyl), and $N(C1-C4-alkyl)_2$. In a further preferred embodiment, said $R^3$ and $R^6$ are independently selected from $NH_2$, N(H)(C1-C2-alkyl), and $N(C1-C2-alkyl)_2$. In a further preferred embodiment, said $R^3$ and $R^6$ are independently selected from $NH_2$, $N(H)(C_2H_5)$, and $N(C_2H_5)_2$. In a further preferred embodiment, said $R^3$ and $R^6$ are independently selected from $NH_2$, N(H)(Me), and $N(Me)_2$.

In a further very preferred embodiment, said $R^3$ is selected from H, $NH_2$, N(H)(C1-C6-alkyl), and $N(C1-C6-alkyl)_2$. In a further very preferred embodiment, said $R^6$ is selected from H, $NH_2$, N(H)(C1-C6-alkyl), and $N(C1-C6-alkyl)_2$. In a further very preferred embodiment, said $R^3$ is selected from H, $NH_2$, N(H)(C1-C4-alkyl), and $N(C1-C4-alkyl)_2$. In a further very preferred embodiment, said $R^6$ is selected from H, $NH_2$, N(H)(C1-C4-alkyl), and $N(C1-C4-alkyl)_2$. In a further very preferred embodiment, said $R^3$ is selected from H, $NH_2$, N(H)(C1-C2-alkyl), and $N(C1-C2-alkyl)_2$. In a further very preferred embodiment, said $R^6$ is selected from H, $NH_2$, N(H)(C1-C2-alkyl), and $N(C1-C2-alkyl)_2$. In a further very preferred embodiment, said $R^3$ is selected from $NH_2$, N(H)(C1-C2-alkyl), and $N(C1-C2-alkyl)_2$. In a further very preferred embodiment, said $R^6$ is selected from $NH_2$, N(H)(C1-C2-alkyl), and $N(C1-C2-alkyl)_2$. In a further very preferred embodiment, said $R^3$ is selected from $NH_2$, $N(H)(C_2H_5)$, and $N(C_2H_5)_2$. In a further very preferred embodiment, said $R^6$ is selected from $NH_2$, $N(H)(C_2H_5)$, and $N(C_2H_5)_2$. In a further very preferred embodiment, said $R^3$ is selected from H, $NH_2$, N(H)(Me), and $N(Me)_2$. In a further very preferred embodiment, said $R^6$ is selected from H, $NH_2$, N(H)(Me), and $N(Me)_2$. In a further very preferred embodiment, said $R^3$ is selected from $NH_2$, N(H)(Me), and $N(Me)_2$. In a further very preferred embodiment, said $R^6$ is selected from $NH_2$, N(H)(Me), and $N(Me)_2$.

In a further very preferred embodiment, said $R^3$ is selected from $NH_2$ and $N(C_2H_5)_2$. In a further very preferred embodiment, said $R^6$ is selected from $NH_2$ and $N(C_2H_5)_2$. In a further very preferred embodiment, said $R^3$ is selected from H, $NH_2$ and $N(Me)_2$. In a further very preferred embodiment, said $R^6$ is selected from H, $NH_2$ and $N(Me)_2$. In a further very preferred embodiment, said $R^3$ is selected from $NH_2$ and $N(Me)_2$. In a further very preferred embodiment, said $R^6$ is selected from $NH_2$ and $N(Me)_2$.

In a further very preferred embodiment, said $R^3$ is H. In a further very preferred embodiment, said $R^3$ is s $NH_2$. In a further very preferred embodiment, said $R^3$ is N(H)(Me). In a further very preferred embodiment, said $R^3$ is $N(Et)_2$. In a further very preferred embodiment, said $R^3$ is $N(Me)_2$. In a further very preferred embodiment, said $R^6$ is H. In a further very preferred embodiment, said $R^6$ is s $NH_2$. In a further very preferred embodiment, said $R^6$ is N(H)(Me). In a further very preferred embodiment, said $R^6$ is $N(Et)_2$. In a further very preferred embodiment, said $R^6$ is $N(Me)_2$.

In a further preferred embodiment, said $R^1$ is selected from C1-C6-alkoxy, aryloxy, O-alkyl-aryl, C1-C6-hydroxyalkyl, $O(CH_2)O(CH_3)$, $O(CH_2)O(CH_2)_2OCH_3$, $NH_2$, N(H)(C1-C6-alkyl), $N(C1-C6-alkyl)_2$, SH, F, $CF_3$, C1-C6-alkyl-thio, 4,4-dimethyl-4,5-dihydrooxazole, $NHCOR^{14}$, $NHCO_2R^{14}$, $OCN(R^{14})_2$, $CONHR^{14}$, $CON(R^{14})_2$, $C=NR^{14}$, $CO_2H$, $[CO_2^-]$, $CO_2R^{14}$, $SO_3R^{14}$, $SO_3H$, $[SO_3^-]$, $SO_2NC(CH_3)_3$, $SO_2N(R^{14})_2$.

In a further preferred embodiment, said $R^1$ is selected from C1-C6-alkoxy, O-alkyl-aryl, $O(CH_2))(CH_3)$, $)(CH_2))(CH_2)_2OCH_3$, $NH_2$, N(H)(C1-C6-alkyl), $N(C1-C6-alkyl)_2$, F, $CF_3$, 4,4-dimethyl-4,5-dihydrooxazole, $NHCOR^{14}$, $NHCO_2R^{14}$, $OCN(R^{14})_2$, $CONHR^{14}$, $CON(R^{14})_2$, $C=NR^{14}$, $CO_2H$, $[CO_2^-]$, $CO_2R^{14}$, $SO_3R^{14}$, $SO_3H$, $[SO_3^-]$, $SO_2NC(CH_3)_3$, $SO_2N(R^{14})_2$.

In a further preferred embodiment, said $R^1$ is selected from C1-C6-alkoxy, O-alkyl-aryl, $O(CH_2)O(CH_3)$, $O(CH_2)O(CH_2)_2OCH_3$, $NH_2$, N(H)(C1-C6-alkyl), $N(C1-C6-alkyl)_2$, F, $CF_3$, 4,4-dimethyl-4,5-dihydrooxazole, $NHCOR^{14}$, $NHCO_2R^{14}$, $OCN(R^{14})_2$, $CONHR^{14}$, $CON(R^{14})_2$, $C=NR^{14}$, $CO_2H$, $[CO_2^-]$, $CO_2R^{14}$, $SO_3R^{14}$.

In a further preferred embodiment, said $R^1$ is selected from C1-C4-alkoxy, $NH_2$, N(H)(C1-C4-alkyl), $N(C1-C4-alkyl)_2$, F, $CF_3$.

In a further preferred embodiment, said $R^1$ is selected from $NH_2$, N(H)(C1-C2-alkyl), $N(C1-C2-alkyl)_2$, C1-C4-alkoxy and F.

In a further preferred embodiment, said $R^1$ is $NH_2$, $N(H)$(C1-C4-alkyl), $N(C1$-C4-alkyl$)_2$, C1-C4-alkoxy or C1-C4-hydroxyalkyl. In a further preferred embodiment, said $R^1$ is $NH_2$, $N(H)(C1$-C2-alkyl), $N(C1$-C2-alkyl$)_2$ or C1-C4-alkoxy. In a preferred embodiment, $R^1$ is $NH_2$, $N(H)(C1$-C2-alkyl), $N(C1$-C2-alkyl$)_2$ or C1-C2-alkoxy. In a preferred embodiment, said $R^1$ is C1-C6-alkoxy, preferably C1-C4-alkoxy, more preferably C1-C3-alkoxy, more preferably ethoxy or methoxy, most preferably methoxy. In a further preferred embodiment, said $R^1$ is selected from $NH_2$, $N(H)$(C1-C6-alkyl) and $N(C1$-C6-alkyl$)_2$. In a further preferred embodiment, $R^1$ is $N(C1$-C6-alkyl$)_2$, wherein said C1-C6-alkyl are independently selected from C1-C6-alkyl, Cl-05-alkyl, C1-C4-alkyl, C1-C3-alkyl, ethyl and methyl. In a preferred embodiment, said $R^1$ is $N(H)Me$, $N(H)Et$, $NMe_2$ or $NEt_2$. In a very preferred embodiment, $R^1$ is OMe, F, $NMe_2$ or $NEt_2$.

In a further very preferred embodiment, said $R^1$ is selected from C1-C2-alkoxy, $NH_2$, $N(H)(C1$-C2-alkyl), $N(C1$-C2-alkyl$)_2$ and F. In a further very preferred embodiment, said $R^1$ is C1-C2-alkoxy, preferably methoxy. In a further very preferred embodiment, said $R^1$ is methoxy. In a further very preferred embodiment, said $R^1$ is selected from $NH_2$, $N(H)$(C1-C2-alkyl), $N(C1$-C2-alkyl$)_2$.

In a further preferred embodiment, said $R^8$ is OH.

In a further preferred embodiment, said $R^8$ is selected from H, halogen, C1-C6-alkoxy, C1-C6-hydroxyalkyl, $O(CH_2)O(CH_3)$, $O(CH_2)O(CH_2)_2OCH_3$, $NH_2$, $N(H)(C1$-C6-alkyl), $N(C1$-C6-alkyl$)_2$, SH, F, $CF_3$, C1-C6-alkylthio, 4,4-dimethyl-4,5-dihydrooxazole, $NHCOR^{14}$, $NHCO_2R^{14}$, $OCNR_2$, $CONHR^{14}$, $CON(R^{14})_2$, $C=NR^{14}$, $CO_2H$, $[CO_2^-]$, $NO_2$, $SO_3R^{14}$, $SO_3H$, $SO_2NC(CH_3)_3$ and $SO_2N(R^{14})_2$.

In a further preferred embodiment, said $R^8$ is selected from H, C1-C4-alkoxy, $NH_2$, $N(H)(C1$-C4-alkyl), $N(C1$-C4-alkyl$)_2$, F, $CF_3$.

In a further preferred embodiment, said $R^8$ is selected from H, C1-C6-alkoxy.

In a further preferred embodiment, said $R^8$ is selected from H, $NH_2$, $N(H)(C1$-C2-alkyl), $N(C1$-C2-alkyl$)_2$, C1-C4-alkoxy and F.

In a further very preferred embodiment, said $R^8$ is selected from H, C1-C2-alkoxy, $NH_2$, $N(H)(C1$-C2-alkyl), $N(C1$-C2-alkyl$)_2$ and F. In a further very preferred embodiment, said $R^8$ is H. In a further very preferred embodiment, said $R^8$ is C1-C2-alkoxy, preferably methoxy. In a further very preferred embodiment, said $R^8$ is methoxy. In a further very preferred embodiment, said $R^8$ is selected from $NH_2$, $N(H)$(C1-C2-alkyl), $N(C1$-C2-alkyl$)_2$.

In a further very preferred embodiment, said $R^8$ is selected from C1-C2-alkoxy, $NH_2$, $N(H)(C1$-C2-alkyl), $N(C1$-C2-alkyl$)_2$ and F. In a further very preferred embodiment, said $R^8$ is H. In a further very preferred embodiment, said $R^8$ is not H.

In a further preferred embodiment, said $R^m$ is selected from aryl, heteroaryl, C1-C4-alkyl-aryl, C2-C6-alkenyl-aryl, C2-C12-alkenyl, C2-C12-alkynyl, C1-C12-alkyl, H, C1-C12-hydroxyalkyl, C1-C12-alkyl-$CO_2H$, C1-C12-alkyl-$CO_2$—C1-C12-alkyl, C1-C12-alkyl-$CO_2$-C1-C4-alkyl-aryl, $O^-$; wherein said aryl and heteroaryl are optionally substituted by one or more groups independently selected from halogen atoms, CN, $N_3$, C1-C6-alkyl, $[SO_3]^-$, $SO_3H$, $SO_2Cl$, OH, C1-C6-alkoxy, $C(=O)OH$ and C1-C6-alkoxycarbonyl.

In a further preferred embodiment, said $R^m$ is selected from aryl, heteroaryl, C1-C4-alkyl-aryl, C1-C12-alkyl, C1-C12-alkyl-$CO_2H$, C1-C12-alkyl-$CO_2$-C1-C12-alkyl, C1-C12-alkyl-$CO_2$—C1-C4-alkyl-aryl, $O^-$; wherein said aryl and heteroaryl are optionally substituted by one or more groups independently selected from C1-C6-alkyl, OH and C1-C6-alkoxy.

In a further preferred embodiment, said $R^m$ is selected from aryl, C1-C4-alkyl-aryl, C1-C6-alkyl, C1-C6-alkyl-$CO_2H$, C1-C6-alkyl-$CO_2$-C1-C6-alkyl, C1-C6-alkyl-$CO_2$-C1-C4-alkyl-aryl, $O^-$; wherein said aryl is optionally substituted by one or more groups independently selected from C1-C6-alkyl, OH and C1-C6-alkoxy.

In a further preferred embodiment, said $R^m$ is selected from aryl, C1-C4-alkyl-aryl, C1-C4-alkyl, C1-C4-alkyl-$CO_2H$, C1-C4-alkyl-$CO_2$—C1-C4-alkyl, C1-C4-alkyl-$CO_2$—C1-C4-alkyl-aryl; wherein said aryl is optionally substituted by one or more groups independently selected from C1-C4-alkyl, OH and C1-C4-alkoxy.

In a further preferred embodiment, said $R^m$ is selected from aryl, heteroaryl, C1-C4-alkyl-aryl, C1-C12-alkyl, H, $C(=O)H$, $C(=O)$—C1-C6-alkyl; wherein said aryl and heteroaryl are optionally substituted by one or more groups independently selected from halogen atoms, C1-C6-alkyl, C1-C6-alkoxy.

In a further preferred embodiment, said $R^m$ is selected from aryl, C1-C4-alkyl-aryl, C1-C12-alkyl, $C(=O)H$; wherein said aryl and heteroaryl are optionally substituted by one or more groups independently selected from halogen atoms, C1-C6-alkyl, C1-C6-alkoxy.

In a further very preferred embodiment, said $R^{10}$ is selected from C1-C4-alkyl and aryl.

In a further very preferred embodiment, said $R^{10}$ is selected from ethyl, methyl and phenyl. In a further very preferred embodiment, said $R^{10}$ is methyl. In a further very preferred embodiment, said $R^m$ is phenyl.

In a further preferred embodiment, said $R^N$ is C1-C6-alkyl. In a very further preferred embodiment, said $R^N$ is C1-C4-alkyl. In a further very preferred embodiment, said $R^{14}$ is Me or Et. In a further very preferred embodiment, said $R^{14}$ is Me. In a further very preferred embodiment, said $R^{14}$ is Et.

In a further preferred embodiment, said A is selected from halide ions, $[BF]^-$, $[PF_6]^-$, $[ClO_4]^-$, $[(C1$-C5-alkyl$)C(=O)O]^-$, [aryl-$CH_2$≥$C(=O)O]^-$, [aryl-$C(=O)O]^-$, $[H_2PO_4]^-$ $[HSO_4]^-$ $[SO_4]^{2-}$, $[(C1$-C6-alkyl$)SO_3]^-$, $[CF_3SO_3]^-$, aryl-$CH_2$—$SO_3]^-$ and [aryl-$SO_3]^-$.

In a further preferred embodiment, said A is selected from halide ions, $[BF_4]^-$, $[PF_6]^-$, $[ClO_4]^-$, $[(C1$-C2-alkyl$)C(=O)O]$, [aryl-$CH_2$—$C(=O)O]$, [aryl-$C(=O)O]$, $[H_2PO_4]$, $[(C1$-C4-alkyl$)SO_3]^-$, $[CF_3SO_3]^-$, [aryl-$CH_2$—$SO_3]^-$ and [aryl-$SO_3]^-$.

In a further preferred embodiment, said $A^-$ is selected from halide ions, $[BF_4]^-$, $[PF_6]^-$, $[ClO_4]^-$, $[(C1$-C2-alkyl$)C(=O)O]^-$, [phenyl-$CH_2$—$C(=O)O]^-$, [phenyl-$C(=O)O]^-$, $[H_2PO_4]^-$, $[(C1$-C4-alkyl$)SO_3]^-$, $[CF_3SO_3]^-$, [phenyl-$CH_2$—$SO_3]^-$ and [phenyl-$SO_3]^-$.

In a further preferred embodiment, said $A^-$ is selected from halide ions, $[BF_4]^-$, $[PF_6]^-$, $[ClO_4]^-$, $[(C1$-C2-alkyl$)C(=O)O]^-$, [phenyl-$CH_2$—$C(=O)O]^-$, [phenyl-$C(=O)O]^-$, $[H_2PO_4]^-$, $[(C1$-C4-alkyl$)SO_3]^-$, $[CF_3SO_3]^-$, [phenyl-$CH_2$—$SO_3]^-$ and [phenyl-$SO_3]^-$.

In a further very preferred embodiment, said $A^-$ is selected from $[Cl]^-$, $[Br]^-$, $[I]^-$, $[BF_4]^-$, $[PF_6]^-$, $[ClO_4]^-$,

[CH$_2$C(═O)O]$^-$, [phenyl-CH$_2$—C(═O)O]$^-$, [phenyl-C(═O)O]$^-$, [CH$_3$SO$_3$]$^-$, [CF$_3$SO$_3$]$^-$, [phenyl-CH$_2$—SO$_3$]$^-$ and [phenyl-SO$_3$]$^-$.

In a further very preferred embodiment, said A is selected from [Cl]$^-$, [Br]$^-$, [BF$_4$]$^-$, [PF$_6$]$^-$, [ClO$_4$]$^-$, [CF$_3$SO$_3$] and [(C1-C4-alkyl)SO$_3$].

In a further very preferred embodiment, said A$^-$ is selected from [Cl]$^-$, [Br]$^-$, [BF$_4$]$^-$, [PF$_6$]$^-$, [ClO$_4$]$^-$, [CF$_3$SO$_3$]$^-$ and [CH$_3$SO$_3$]$^-$.

In a further very preferred embodiment, said A$^-$ is [F]. In a further very preferred embodiment, said A$^-$ is [Cl]$^-$. In a further very preferred embodiment, said A$^-$ is [Br]$^-$. In a further very preferred embodiment, said A$^-$ is [I]$^-$. In a further very preferred embodiment, said A$^-$ is [BF$_4$]$^-$. In a further very preferred embodiment, said A$^-$ is [PF$_6$]$^-$. In a further very preferred embodiment, said A$^-$ is [ClO$_4$]$^-$. In a further very preferred embodiment, said A$^-$ is [CH$_2$C(═O)O]$^-$. In a further very preferred embodiment, said A$^-$ is [phenyl-CH$_2$—C(═O)O]$^-$. In a further very preferred embodiment, said A$^-$ is [phenyl-C(═O)O]$^-$. In a further very preferred embodiment, said A$^-$ is [CH$_3$SO$_3$]$^-$. In a further very preferred embodiment, said A$^-$ is [CF$_3$SO$_3$]. In a further very preferred embodiment, said A is [phenyl-CH$_2$—SO$_3$]$^-$. In a further very preferred embodiment, said A$^-$ is [phenyl-SO$_3$]$^-$.

The cation of the substituents [CO$_2$$^-$], [SO$_3$$^-$], and [O]$^-$ suitable for the present inventive compounds are known to the person skilled in the art. In a preferred embodiment, the cation of the substituents [CO$_2$$^-$], [SO$_3$$^-$], or [O]$^-$ are selected from [Li]+, [Na]+, [K]+ and [(C1-C12-alkyl)3NH]+ or the inventive compounds comprising said substituents [CO$_2$$^-$], [SO$_3$$^-$], or [O]$^-$ forming an internal salt and zwitterion, respectively.

In a further preferred embodiment, the compound of the invention is a compound of formula (A), wherein R$^1$ is N(C1-C6-alkyl)$_2$; and wherein R$^6$ is N(C1-C6-alkyl)$_2$; and wherein A$^-$ is selected from halide ions; wherein R$^9$ is aryl optionally substituted by one or more groups independently selected from halogen atoms, CN, N$_3$, C1-C6-alkyl, [SO$_3$]$^-$, SO$_3$H, SO$_2$Cl, OH, C1-C6-alkoxy, C(═O)OH and C1-C6-alkoxycarbonyl; and wherein R$^8$, R$^7$, R$^5$, R$^4$, R$^3$ and R$^2$ are each H.

In a further preferred embodiment, the compound of the invention is a compound of formula (A), wherein R$^1$ is N(C1-C6-alkyl)$_2$; and wherein R$^6$ is N(C1-C6-alkyl)$_2$; and wherein A$^-$ is selected from halide ions; wherein R$^9$ is aryl optionally substituted by one or more groups independently selected from halogen atoms, C1-C6-alkyl, and C1-C6-alkoxy; and wherein R$^8$, R$^7$, R$^5$, R$^4$, R$^3$ and R$^2$ are each H.

In a further preferred embodiment, the compound of the invention is a compound of formula (A), wherein R$^1$ is C1-C6-alkoxy and wherein R$^6$ is N(C1-C6-alkyl)$_2$; and wherein A$^-$ is selected from halide ions; and wherein R$^9$ is aryl optionally substituted by one or more groups independently selected from halogen atoms, CN, N$_3$, C1-C6-alkyl, [SO$_3$]$^-$, SO$_3$H, SO$_2$Cl, OH, C1-C6-alkoxy, C(═O)OH and C1-C6-alkoxycarbonyl; and wherein R$^8$, R$^7$, R$^5$, R$^4$, R$^3$ and R$^2$ are each H.

In a further preferred embodiment, the compound of the invention is a compound of formula (A), wherein R$^1$ is C1-C6-alkoxy; and wherein R$^6$ is N(C1-C6-alkyl)$_2$ and wherein A$^-$ is selected from halide ions; and wherein R$^9$ is aryl optionally substituted by one or more groups independently selected from halogen atoms, C1-C6-alkyl and C1-C6-alkoxy; and wherein R$^8$, R$^7$, R$^5$, R$^4$, R$^3$ and R$^2$ are each H.

In a further very preferred embodiment, said compound is an acridinium cation selected from:
1,8-Dimethoxy-10-methyl-9-phenylacridinium;
9-(4-Fluorophenyl)-1,8-dimethoxy-10-methylacridinium;
1,8-Dimethoxy-9-(4-methoxyphenyl)-10-methylacridinium;
1,8-Dimethoxy-10-methyl-9-(naphthalen-1-yl)acridinium;
1,8-Dimethoxy-9,10-diphenylacridinium;
1,8-Dimethoxy-9,10-diphenylacridinium;
1-Methoxy-10-methyl-9-phenylacridinium;
6-(Dimethylamino)-1-methoxy-10-methyl-9-phenylacridinium;
6-(Dimethylamino)-1-methoxy-9,10-diphenylacridinium;
9-Mesityl-1,8-dimethoxy-10-methylacridinium;
9-Mesityl-1-methoxy-10-methylacridinium;
6-(Dimethylamino)-9-mesityl-1-methoxy-10-methylacridinium;
3,6-Bis(dimethylamino)-9-mesityl-1-methoxy-10-methylacridinium;
3,6-Bis(dimethylamino)-9-mesityl-1,8-dimethoxy-10-methylacridinium;
3-(Dimethylamino)-9-mesityl-1-methoxy-10-methylacridinium:
3-(Dimethylamino)-1,8-dimethoxy-9,10-diphenylacridinium;
(±)-3-(Dimethylamino)-1,8-dimethoxy-9-(naphthalen-1-yl)-10-phenylacridinium;
(±)-3-(Dimethylamino)-9-(4-fluoronaphthalen-1-yl)-1,8-dimethoxy-10-phenylacridinium;
3,6-Bis(dimethylamino)-1,8-dimethoxy-9,10-diphenylacridinium;
1-Methoxy-9,10-diphenylacridinium;
9-Mesityl-1-methoxy-10-phenylacridinium;
9-(2,6-Dimethylphenyl)-1-methoxy-10-phenylacridinium;
(±)-1-Methoxy-9-(naphthalen-1-yl)-10-phenylacridinium;
(±)-1-Methoxy-10-methyl-9-(naphthalen-1-yl)acridinium;
6-(Dimethylamino)-9-mesityl-1-methoxy-10-phenylacridinium;
6-(Dimethylamino)-9-(2,6-dimethylphenyl)-1-methoxy-10-phenylacridinium;
(±)-6-(Dimethylamino)-1-methoxy-9-(naphthalen-1-yl)-10-phenylacridinium;
7-(Dimethylamino)-9-mesityl-1-methoxy-10-phenylacridinium;
(±)-7-(Dimethylamino)-1-methoxy-9-(naphthalen-1-yl)-10-phenylacridinium;
3,7-Bis(dimethylamino)-9-mesityl-1-methoxy-10-phenylacridinium;
3,6-Bis(dimethylamino)-9-mesityl-1-methoxy-10-phenylacridinium;
and wherein said anion A$^-$is selected from halide ions, [BF]$^-$, [PF$_6$]$^-$, [ClO$_4$]$^-$, [(C1-C5-alkyl)C(═O)O]$^-$, [aryl-CH$_2$—C(═O)O]$^-$, [aryl-C(═O)O]$^-$, [H$_2$PO$_4$]$^-$ [HSO$_4$]$^-$, [SO$_4$]$^{2-}$, [(C1-C6-alkyl)SO$_3$]$^-$, [CF$_3$SO$_3$]$^-$, aryl-CH$_2$—SO$_3$]$^-$ and [aryl-SO$_3$]$^-$, and wherein preferably said anion A$^-$ is selected from selected from [I]$^-$, [Cl]$^-$, [Br]$^-$, [BF]$^-$, [PF$_6$]$^-$, [ClO$_4$]$^-$, [CH$_2$C(═O)O]$^-$, [phenyl-CH$_2$—C(═O)O]$^-$, [phenyl-C(═O)O]$^-$, [CH$_3$ SO$_3$]$^-$, [phenyl-CH$_2$—SO$_3$]$^-$ and [phenyl-SO$_3$]$^-$.

In a further preferred embodiment, said compound is 6-(Dimethylamino)-9-(4-fluorophenyl)-1-methoxyxanthylium.

In a further very preferred embodiment, said compound of the invention is a compound of formula (A) selected from:
1,8-Dimethoxy-10-methyl-9-phenylacridinium bromide;
9-(4-Fluorophenyl)-1,8-dimethoxy-10-methylacridinium bromide;
1,8-Dimethoxy-9-(4-methoxyphenyl)-10-methylacridinium bromide;
1,8-Dimethoxy-10-methyl-9-(naphthalen-1-yl)acridinium bromide;
1,8-Dimethoxy-9,10-diphenylacridinium bromide;
1,8-Dimethoxy-9,10-diphenylacridinium tetrafluoroborate;
1-Methoxy-10-methyl-9-phenylacridinium bromide;
6-(Dimethylamino)-1-methoxy-10-methyl-9-phenylacridinium bromide;
6-(Dimethylamino)-9-(4-fluorophenyl)-1-methoxyxanthylium bromide;
6-(Dimethylamino)-9-(4-fluorophenyl)-1-methoxyxanthylium chloride;
6-(Dimethylamino)-1-methoxy-9,10-diphenylacridinium bromide;
9-Mesityl-1,8-dimethoxy-10-methylacridinium bromide;
9-Mesityl-1-methoxy-10-methylacridinium bromide;
6-(Dimethylamino)-9-mesityl-1-methoxy-10-methylacridinium bromide;
3,6-Bis(dimethylamino)-9-mesityl-1-methoxy-10-methylacridinium bromide;
3,6-Bis(dimethylamino)-9-mesityl-1,8-dimethoxy-10-methylacridinium bromide;
3-(Dimethylamino)-9-mesityl-1-methoxy-10-methylacridinium bromide;
3-(Dimethylamino)-1,8-dimethoxy-9,10-diphenylacridinium bromide;
(±)-3-(Dimethylamino)-1,8-dimethoxy-9-(naphthalen-1-yl)-10-phenylacridinium bromide;
(±)-3-(Dimethylamino)-9-(4-fluoronaphthalen-1-yl)-1,8-dimethoxy-10-phenylacridinium bromide;
3,6-Bis(dimethylamino)-1,8-dimethoxy-9,10-diphenylacridinium bromide
1-Methoxy-9,10-diphenylacridinium bromide;
9-Mesityl-1-methoxy-10-phenylacridinium bromide;
9-(2,6-Dimethylphenyl)-1-methoxy-10-phenylacridinium bromide;
(±)-1-Methoxy-9-(naphthalen-1-yl)-10-phenylacridinium bromide;
(±)-1-Methoxy-10-methyl-9-(naphthalen-1-yl)acridinium bromide;
6-(Dimethylamino)-9-mesityl-1-methoxy-10-phenylacridinium bromide;
6-(Dimethylamino)-9-(2,6-dimethylphenyl)-1-methoxy-10-phenylacridinium bromide;
(±)-6-(Dimethylamino)-1-methoxy-9-(naphthalen-1-yl)-10-phenylacridinium bromide;
7-(Dimethylamino)-9-mesityl-1-methoxy-10-phenylacridinium bromide;
(±)-7-(Dimethylamino)-1-methoxy-9-(naphthalen-1-yl)-10-phenylacridinium bromide;
3,7-Bis(dimethylamino)-9-mesityl-1-methoxy-10-phenylacridinium bromide; and
3,6-Bis(dimethylamino)-9-mesityl-1-methoxy-10-phenylacridinium bromide.

In a further very preferred embodiment, said compound is 1,8-dimethoxy-10-methyl-9-phenylacridinium bromide.

In a further very preferred embodiment, said compound is 9-(4-fluorophenyl)-1,8-dimethoxy-10-methylacridinium bromide.

In a further very preferred embodiment, said compound is 1,8-dimethoxy-9-(4-methoxyphenyl)-10-methylacridinium bromide.

In a further very preferred embodiment, said compound is 1,8-dimethoxy-10-methyl-9-(naphthalen-1-yl)acridinium bromide.

In a further very preferred embodiment, said compound is 1,8-dimethoxy-9,10-diphenylacridinium bromide.

In a further very preferred embodiment, said compound is 1,8-dimethoxy-9,10-diphenylacridinium tetrafluoroborate.

In a further very preferred embodiment, said compound is 1-methoxy-10-methyl-9-phenylacridinium bromide.

In a further very preferred embodiment, said compound is 6-(dimethylamino)-1-methoxy-10-methyl-9-phenylacridinium bromide.

In a further very preferred embodiment, said compound is 6-(dimethylamino)-9-(4-fluorophenyl)-1-methoxyxanthylium bromide.

In a further very preferred embodiment, said compound is 6-(dimethylamino)-9-(4-fluorophenyl)-1-methoxyxanthylium chloride.

In a further very preferred embodiment, said compound is 6-(dimethylamino)-1-methoxy-9,10-diphenylacridinium bromide.

In a further very preferred embodiment, said compound is 9-mesityl-1,8-dimethoxy-10-methylacridinium bromide.

In a further very preferred embodiment, said compound is 9-mesityl-1-methoxy-10-methylacridinium bromide.

In a further very preferred embodiment, said compound is 6-(dimethylamino)-9-mesityl-1-methoxy-10-methylacridinium bromide.

In a further very preferred embodiment, said compound is 3,6-bis(dimethylamino)-9-mesityl-1-methoxy-10-methylacridinium bromide.

In a further very preferred embodiment, said compound is 3,6-bis(dimethylamino)-9-mesityl-1,8-dimethoxy-10-methylacridinium bromide.

In a further very preferred embodiment, said compound is 3-(dimethylamino)-9-mesityl-1-methoxy-10-methylacridinium bromide.

In a further very preferred embodiment, said compound is 3-(Dimethylamino)-1,8-dimethoxy-9,10-diphenylacridinium bromide.

In a further very preferred embodiment, said compound is (±)-3-(Dimethylamino)-1,8-dimethoxy-9-(naphthalen-1-yl)-10-phenylacridinium bromide.

In a further very preferred embodiment, said compound is (±)-3-(Dimethylamino)-9-(4-fluoronaphthalen-1-yl)-1,8-dimethoxy-10-phenylacridinium bromide.

In a further very preferred embodiment, said compound is 3,6-Bis(dimethylamino)-1,8-dimethoxy-9,10-diphenylacridinium bromide.

In a further very preferred embodiment, said compound is 1-Methoxy-9,10-diphenylacridinium bromide.

In a further very preferred embodiment, said compound is 9-Mesityl-1-methoxy-10-phenylacridinium bromide.

In a further very preferred embodiment, said compound is 9-(2,6-Dimethylphenyl)-1-methoxy-10-phenylacridinium bromide.

In a further very preferred embodiment, said compound is (±)-1-Methoxy-9-(naphthalen-1-yl)-10-phenylacridinium bromide.

In a further very preferred embodiment, said compound is (±)-1-Methoxy-10-methyl-9-(naphthalen-1-yl)acridinium bromide.

In a further very preferred embodiment, said compound is 6-(Dimethylamino)-9-mesityl-1-methoxy-10-phenylacridinium bromide.

In a further very preferred embodiment, said compound is 6-(Dimethylamino)-9-(2,6-dimethylphenyl)-1-methoxy-10-phenylacridinium bromide.

In a further very preferred embodiment, said compound is (±)-6-(Dimethylamino)-1-methoxy-9-(naphthalen-1-yl)-10-phenylacridinium bromide.

In a further very preferred embodiment, said compound is 7-(Dimethylamino)-9-mesityl-1-methoxy-10-phenylacridinium bromide.

In a further very preferred embodiment, said compound is (±)-7-(Dimethylamino)-1-methoxy-9-(naphthalen-1-yl)-10-phenylacridinium bromide.

In a further very preferred embodiment, said compound is 3,7-Bis(dimethylamino)-9-mesityl-1-methoxy-10-phenylacridinium bromide.

In a further very preferred embodiment, said compound is 3,6-Bis(dimethylamino)-9-mesityl-1-methoxy-10-phenylacridinium bromide.

In a further aspect, the present invention provides for a compound of formula (A')

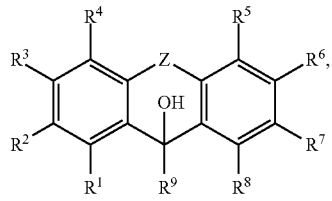

wherein
$Z$ is $NR^{10}$;
$R^1$ is selected from C1-C6-alkoxy, aryloxy, O-alkyl-aryl, C1-C6-hydroxyalkyl, $O(CH_2)O(CH_3)$, $O(CH_2)O(CH_2)_2OCH_3$, $NH_2$, $N(H)(C1-C6-alkyl)$, $N(C1-C6-alkyl)_2$, SH, F, $CF_3$, C1-C6-alkylthio, 4,4-dimethyl-4,5-dihydrooxazole, $NHCOR^{14}$, $NHCO_2R^{14}$, $OCNR_2$, $CONHR^{14}$, $CON(R^{14})_2$, $C=NR^{14}$, $CO_2H$, $[CO_2^-]$, $CO_2R^{14}$, $[SO_3^-]$, $SO_3R^{14}$, $SO_3H$, $SO_2NC(CH_3)_3$, $SO_2N(R^{14})_2$;
$R^2$ is selected from H, halogen, $NO_2$, CN, $NH_2$, $N(H)(C1-C6-alkyl)$, $N(C1-C6-alkyl)_2$, OH, C1-C6-alkoxy, C1-C6-hydroxyalkyl, SH, C1-C6-alkylthio, $[SO_3]$, $SO_3H$, $SO_3R^{14}$, $CO_2H$, $[CO2]$, $CO_2R^{14}$, C1-C12-alkyl;
$R^3$ is selected from H, halogen, $NO_2$, and CN;
$R^4$ is selected from H, C1-C12-alkyl, halogen, $NO_2$, CN, $NH_2$, $N(H)(C1-C6-alkyl)$, $N(C1-C6-alkyl)_2$, OH, C1-C6-alkoxy, aryloxy, O-alkyl-aryl, C1-C6-hydroxyalkyl, SH, C1-C6-alkylthio, $SO_3R^{14}$, $[SO_3]$, $SO_3H$;
$R^5$ is selected from H, C1-C12-alkyl, halogen, $NO_2$, CN, $NH_2$, $N(H)(C1-C6-alkyl)$, $N(C1-C6-alkyl)_2$, OH, C1-C6-hydroxyalkyl, SH, C1-C6-alkylthio, $SO_3R^{14}$, $SO_3H$, $[SO_3^-]$;
$R^6$ is selected from H, halogen, $NO_2$, CN, $NH_2$, $N(H)(C1-C6-alkyl)$, $N(C1-C6-alkyl)_2$, C1-C6-hydroxyalkyl;
$R^7$ is selected from H, halogen, $NO_2$, CN, $NH_2$, $N(H)(C1-C6-alkyl)$, $N(C1-C6-alkyl)_2$, OH, C1-C6-alkoxy and C1-C6-hydroxyalkyl, SH, C1-C6-alkylthio, C1-C12-alkyl, $SO_3R^{14}$, $SO_3H$, $[SO_3]$, $CO_2H$, $[CO2]$, $CO_2R^{14}$;
$R^8$ is selected from H, halogen, C1-C6-alkoxy, OH, C1-C6-hydroxyalkyl, $O(CH_2)O(CH_3)$, $O(CH_2)O(CH_2)_2OCH_3$, $NH_2$, $N(H)(C1-C6-alkyl)$, $N(C1-C6-alkyl)_2$, SH, F, $CF_3$, C1-C6-alkylthio, 4,4-dimethyl-4,5-dihydrooxazole, $NHCOR^{14}$, $NHCO_2R^{14}$, $OCNR_2$, $CONHR^{14}$, $CON(R^{14})_2$, $C=NR^{14}$, $CO_2H$, $[CO2]$, $NO_2$, $SO_3R^{14}$, $SO_3H$, $SO_2NC(CH_3)_3$ and $SO_2N(R^{14})_2$;

$R^9$ is selected from aryl, heteroaryl, C2-C6-alkenyl-aryl, C2-C12-alkenyl, C2-C12-alkynyl, C1-C12-alkyl, $NH_2$, $N(H)(C1-C6-alkyl)$, $N(C1-C6-alkyl)_2$, C1-C12-alkoxy, C1-C12-hydroxyalkyl, halogen, CN, $N_3$, C1-C4-alkyl-$CO_2H$, C1-C4-alkyl-$CO_2$-C1-C6-alkyl, C(=O)H, C(=O)-C1-C6-alkyl and C1-C12-alkylthio; and wherein said aryl and heteroaryl are optionally substituted by one or more groups independently selected from halogen atoms, CN, $N_3$, C1-C6-alkyl, $[SO_3]$, $SO_3H$, $SO_2Cl$, OH, C1-C6-alkoxy, C(=O)OH and C1-C6-alkoxycarbonyl, C1-C12-hydroxyalkyl, C1-C12-thio alkyl;

$R^{10}$ is selected from aryl, heteroaryl, C1-C4-alkyl-aryl, C2-C6-alkenyl-aryl, C2-C12-alkenyl, C2-C12-alkynyl, C1-C12-alkyl, H, C1-C12-hydroxyalkyl, C(=O)H, C(=O)—C1-C6-alkyl, C1-C12-alkylthio, C1-C12-alkyl-$CO_2H$; C1-C12-alkyl-$CO_2$-C1-C12-alkyl, C1-C12-alkyl-$CO_2$-C1-C4-alkyl-aryl, [0]; S(=O)—C1-C6-alkyl, S(=O) aryl, S(=O)-heteroaryl, $S(O_2)$-C1-C6-alkyl, $S(O_2)$-aryl, $S(O_2)$-heteroaryl; wherein said aryl and heteroaryl are optionally substituted by one or more groups independently selected from halogen atoms, CN, $N_3$, C1-C6-alkyl, $[SO_3]$, $SO_3H$, $SO_2Cl$, OH, C1-C6-alkoxy, C(=O)OH and C1-C6-alkoxycarbonyl;

$R^{14}$ is selected from C1-C12-alkyl.

In preferred embodiments, any one of said $R^1$, $R^2$, $R^3$, $R^4$, $R^5$, $R^6$, $R^7$, $R^8$, $R^9$, $R^{10}$ and $R^{14}$, are independently defined as in any one of described embodiments for the inventive compound of formula (A).

In a very preferred embodiment, said compound of formula (A') is 1,8-Dimethoxy-10-methyl-9-phenyl-9,10-dihydroacridin-9-ol.

In a further aspect, the present invention provides for a process for the preparation of the inventive compound of formula (A), comprising
(i) reacting a compound of formula (A') with an organometallic reagent ($R^{12}M$) selected from aryl-MgX, C1-C6-alkyl-MgX, aryl-Li and C1-C6-alkyl-Li;

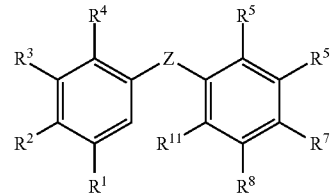

to form a compound of formula (A")

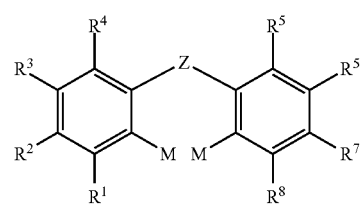

wherein when $R^{11}$ is H, then $R^8$ is selected from C1-C6-alkoxy, OH, C1-C6-hydroxyalkyl, $O(CH_2)O(CH_3)$, $O(CH_2)$ O(CH$_2$)$_2$OCH$_3$, NH$_2$, N(H)(C1-C6-alkyl), N(C1-C6-alkyl)$_2$, SH, F, CF$_3$, C1-C6-alkylthio, 4,4-dimethyl-4,5-dihydrooxazole, NHCOR$^{14}$, NHCO$_2$R$^{14}$, OCN(R$^{14}$)$_2$, CONHR$^{14}$, CON(R$^{14}$)$_2$, C=NR$^{14}$, CO$_2$H, [CO$_2$], SO$_3$R$^{14}$, SO$_3$H, [SO$_3$], SO$_2$NC(CH$_3$)$_3$, SO$_2$N(R$^{14}$)$_2$; and wherein when R$^{11}$ is halogen, then R$^8$ is selected from C1-C6-alkoxy, OH, C1-C6-hydroxyalkyl, O(CH$_2$)O(CH$_3$), O(CH$_2$)O(CH$_2$)$_2$OCH$_3$, NH$_2$, N(H)(C1-C6-alkyl), N(C1-C6-alkyl)$_2$, SH, F, CF$_3$, C1-C6-alkylthio, 4,4-dimethyl-4,5-dihydrooxazole, NHCOR$^{14}$, NHCO$_2$R$^{14}$, OCN(R$^{14}$)$_2$, CONHR$^{14}$, CON(R$^{14}$)$_2$, C=NR$^{14}$, CO$_2$H, [CO$_2$], SO$_3$R$^{14}$, SO$_3$H, [SO$_3$], SO$_2$NC(CH$_3$)$_3$, SO$_2$N(R$^{14}$)$_2$ and H; and wherein M is Li when the organometallic reagent (R$^{12}$M) is aryl-Li or C1-C6-alkyl-Li; and wherein M is MgX when the organometallic reagent (R$^{12}$M) is aryl-MgX or C1-C6-alkyl-MgX or MgX$_2$ or alkyl$_2$Mg or aryl$_2$Mg; and wherein X is a halogen; and wherein R$^1$ to R$^7$ and Z are defined as in any one of the claims 1 to 10;

(ii) followed by reacting said compound of formula (A") with a compound of formula (B) or (C)

R$^9$CO$_2$R$^{13}$ (B)

R$^9$COCl (C)

to form a compound of formula (A')

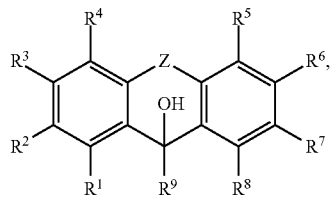

A' wherein R$^9$ is defined as in any one of the claims 1 to 10; and wherein R$^{13}$ is C1-C6-alkyl, C1-C6-alkanoyl; or wherein R$^9$ and R$^{13}$ together with the atoms to which they are attached form a 4 to 6-membered ring optionally substituted by C2-C6-alkenyl-aryl, C2-C12-alkenyl, C2-C12-alkynyl, C1-C12-alkyl, NH$_2$, N(H)(C1-C6-alkyl), N(C1-C6-alkyl), C1-C12-alkoxy, C1-C12-hydroxyalkyl, halogen, CN, N$_3$, C1-C4-alkyl-CO$_2$H, C1-C4-alkyl-CO$_2$-C1-C6-alkyl, C(=O)H, C(=O)-C1-C6-alkyl and C1-C12-alkylthio; or wherein R$^9$ and R$^{13}$ together with the atoms to which they are attached form a 4 to 6-membered ring fused to an aryl or heteroaryl, wherein said aryl or heteroaryl is optionally substituted by one or more groups independently selected from halogen atoms, CN, N$_3$, C1-C6-alkyl, [SO$_3$], SO$_3$H, SO$_2$Cl, OH, C1-C6-alkoxy, C(=O)OH and C1-C6-alkoxycarbonyl, C1-C12-hydroxyalkyl, C1-C12-thio alkyl;

(iii) addition of a protonic acid HA to form a compound of formula (A), wherein said HA is a suitable acid preferably selected from an inorganic acid or an organic acid, and wherein further preferably said inorganic acid is selected from HBr, HCl, HI, HBF$_4$, HPF$_6$ and HClO$_4$, and said organic acid is selected from (C1-C5-alkyl)C(=O)OH, aryl-CH$_2$—C(=O)OH, [aryl-C(=O)OH, H$_3$PO$_4$, (C1-C6-alkyl)SO$_3$H, aryl-CH$_2$—SO$_3$H and aryl-SO$_3$H, and wherein again further preferably said inorganic acid is selected from HBr, HCl, HBF$_4$, HPF$_6$ and HClO$_4$, and said organic acid is selected from (C1-C6-alkyl)SO$_3$H.

In a further aspect, the present invention provides for a process for the preparation of the compound of formula (A)

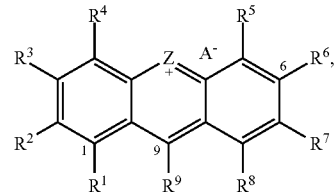

A wherein

Z is selected from NR$^{10}$ and O;

R$^1$ is selected from C1-C6-alkoxy, OH, aryloxy, O-alkyl-aryl, C1-C6-hydroxyalkyl, O(CH$_2$)O(CH$_3$), O(CH$_2$)O(CH$_2$)$_2$OCH$_3$, NH$_2$, N(H)(C1-C6-alkyl), N(C1-C6-alkyl)$_2$, SH, F, CF$_3$, C1-C6-alkylthio, 4,4-dimethyl-4,5-dihydrooxazole, NHCOR$^{14}$, NHCO$_2$R$^{14}$, OCNR$_2$, CONHR$^{14}$, CON(R$^{14}$)$_2$, C=NR$^{14}$, CO$_2$H, [CO$_2$], CO$_2$R$^{14}$, SO$_3$R$^{14}$, SO$_3$H, [SO$_3$], SO$_2$NC(CH$_3$)$_3$, SO$_2$N(R$^{14}$)$_2$;

R$^2$ is selected from H, halogen, NO$_2$, CN, NH$_2$, N(H)(C1-C6-alkyl), N(C1-C6-alkyl)$_2$, OH, C1-C6-alkoxy, C1-C6-hydroxyalkyl, SH, C1-C6-alkylthio, C1-C12-alkyl, SO$_3$H, [SO$_3$], SO$_3$R$^{14}$·CO$_2$H, [CO$_2^-$], CO$_2$R$^{14}$;

R$^3$ is selected from H, halogen, NO$_2$, NH$_2$, N(H)(C1-C6-alkyl), N(C1-C6-alkyl)$_2$, NH$_2$, N(H)(C1-C6-alkyl), N(C1-C6-alkyl)$_2$, OH, SH, C1-C6-alkylthio and CN;

R$^4$ is selected from H, C1-C12-alkyl, halogen, NO$_2$, CN, NH$_2$, N(H)(C1-C6-alkyl), N(C1-C6-alkyl)$_2$, OH, C1-C6-alkoxy, aryloxy, O-alkyl-aryl, C1-C6-hydroxyalkyl, SH, C1-C6-alkylthio, SO$_3$H, [SO$_3$], SO$_3$R$^{14}$;

R$^5$ is selected from H, C1-C12-alkyl, halogen, NO$_2$, CN, NH$_2$, N(H)(C1-C6-alkyl), N(C1-C6-alkyl)$_2$, OH, C1-C6-alkoxy, aryloxy, O-alkyl-aryl, C1-C6-hydroxyalkyl, SH, C1-C6-alkylthio, SO$_3$H, [SO$_3$], SO$_3$R$^{14}$;

R$^6$ is selected from H, halogen, NO$_2$, CN, NH$_2$, N(H)(C1-C6-alkyl), N(C1-C6-alkyl)$_2$, OH, C1-C6-alkoxy, aryloxy, O-alkyl-aryl, C1-C6-hydroxyalkyl, SH, C1-C6-alkylthio;

R$^7$ is selected from H, halogen, NO$_2$, CN, NH$_2$, N(H)(C1-C6-alkyl), N(C1-C6-alkyl)$_2$, OH, C1-C6-alkoxy, C1-C6-hydroxyalkyl, SH, C1-C6-alkylthio, C1-C12-alkyl, SO$_3$H, [SO$_3$], SO$_3$R$^{14}$, CO$_2$H, [CO$_2^-$], CO$_2$R$^{14}$;

R$^8$ is selected from H, halogen, C1-C6-alkoxy, OH, C1-C6-hydroxyalkyl, O(CH$_2$)O(CH$_3$), O(CH$_2$)O(CH$_2$)$_2$OCH$_3$, NH$_2$, N(H)(C1-C6-alkyl), N(C1-C6-alkyl)$_2$, SH, F, CF$_3$, C1-C6-alkylthio, 4,4-dimethyl-4,5-dihydrooxazole, NHCOR$^{14}$, NHCO$_2$R$^{14}$, OCN(R$^{14}$)$_2$, CONHR$^{14}$, CON(R$^{14}$)$_2$, C=NR$^{14}$, CO$_2$H, [CO$_2$], NO$_2$, SO$_3$R$^{14}$, SO$_3$H, SO$_2$NC(CH$_3$)$_3$ and SO$_2$N(R$^{14}$)$_2$;

R$^9$ is selected from aryl, heteroaryl, C1-C4-alkyl-aryl, C2-C6-alkenyl-aryl, C2-C12-alkenyl, C2-C12-alkynyl, C1-C12-alkyl, H, NH$_2$, N(H)(C1-C6-alkyl), N(C1-C6-alkyl)$_2$, C1-C12-alkoxy, C1-C12-hydroxyalkyl, halogen, CN, N$_3$, C(=O)H, C(=O)—C1-C6-alkyl and C1-C12-alkylthio; and wherein said aryl and heteroaryl are optionally substituted by one or more groups independently selected from halogen atoms, CN, N$_3$, C1-C6-alkyl, [SO$_3$]$^-$, SO$_3$H, SO$_2$Cl, OH, C1-C6-alkoxy, C1-C4-alkyl-CO$_2$H, C1-C4-alkyl-CO$_2$—C1-C6-alkyl, C(=O)OH and C1-C6-alkoxycarbonyl, C1-C12-hydroxyalkyl, C1-C12-thio alkyl;

R$^{10}$ is selected from aryl, heteroaryl, C1-C4-alkyl-aryl, C2-C6-alkenyl-aryl, C2-C12-alkenyl, C2-C12-alkynyl, C1-C12-alkyl, H, C1-C12-hydroxyalkyl, C(=O)H, C(=O)—C1-C6-alkyl, C1-C12-alkylthio, C1-C12-alkyl-CO$_2$H; C1-C12-alkyl-CO$_2$—C1-C12-alkyl, C1-C12-alkyl-CO$_2$—C1-C4-alkyl-aryl, O$^-$; S(=O)—C1-C6-alkyl, S(=O)aryl, S(=O)-heteroaryl, S(O$_2$)-C1-C6-alkyl, S(O$_2$)-aryl, S(O$_2$)-heteroaryl; wherein said aryl and heteroaryl are optionally substituted by one or more groups independently selected from halogen atoms, CN, N$_3$, C1-C6-alkyl, [SO$_3$]$^-$, SO$_3$H, SO$_2$Cl, OH, C1-C6-alkoxy, C(=O)OH and C1-C6-alkoxycarbonyl;

R$^{14}$ is selected from C1-C12-alkyl; and

A$^-$ is a suitable anion preferably selected from halide ions, [BF$_4$]$^-$, [PF$_6$]$^-$, [ClO$_4$]$^-$, [(C1-C5-alkyl)C(=O)O]$^-$, [aryl-CH$_2$—C(=O)O]$^-$, [aryl-C(=O)O]$^-$, [H$_2$PO$_4$]$^-$ [HSO$_4$]$^-$ [SO$_4$]$^{2-}$, [(C1-C6-alkyl)SO$_3$]$^-$, [CF$_3$SO$_3$]$^-$, aryl-CH$_2$—SO$_3$]$^-$ and [aryl-SO$_3$]$^-$; comprising (i) reacting a compound of formula (A''') with an organometallic reagent (R$^{12}$M) selected from aryl-MgX, C1-C6-alkyl-MgX, aryl-Li and C1-C6-alkyl-Li;

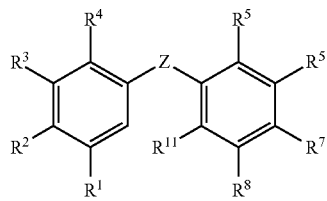

to form a compound of formula (A'')

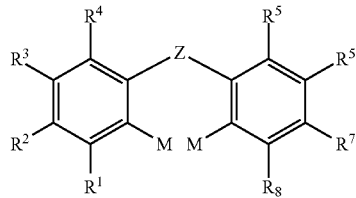

wherein when R$^{11}$ is H, then R$^8$ is selected from C1-C6-alkoxy, OH, C1-C6-hydroxyalkyl, O(CH$_2$)O(CH$_3$), O(CH$_2$)O(CH$_2$)$_2$OCH$_3$, NH$_2$, N(H)(C1-C6-alkyl), N(C1-C6-alkyl)$_2$, SH, F, CF$_3$, C1-C6-alkylthio, 4,4-dimethyl-4,5-dihydrooxazole, NHCOR$^{14}$, NHCO$_2$R$^{14}$, OCN(R$^{14}$)$_2$, CONHR$^{14}$, CON(R$^{14}$)$_2$, C=NR$^{14}$, CO$_2$H, [CO$_2^-$], SO$_3$R$^{14}$, SO$_3$H, [SO$_3$], SO$_2$NC(CH$_3$)$_3$, SO$_2$N(R$^{14}$)$_2$; and wherein when R$^{11}$ is halogen, then R$^8$ is selected from C1-C6-alkoxy, OH, C1-C6-hydroxyalkyl, O(CH$_2$)O(CH$_3$), O(CH$_2$)O(CH$_2$)$_2$OCH$_3$, NH$_2$, N(H)(C1-C6-alkyl), N(C1-C6-alkyl)$_2$, SH, F, CF$_3$, C1-C6-alkylthio, 4,4-dimethyl-4,5-dihydrooxazole, NHCOR$^{14}$, NHCO$_2$R$^{14}$, OCN(R$^{14}$)$_2$, CONHR$^{14}$, CON(R$^{14}$)$_2$, C=NR$^{14}$, CO$_2$H, [CO$_2^-$], SO$_3$R$^{14}$, SO$_3$H, [SO$_3$], SO$_2$NC(CH$_3$)$_3$, SO$_2$N(R$^{14}$)$_2$ and H; and wherein M is Li when the organometallic reagent (R$^{12}$M) is aryl-Li or C1-C6-alkyl-Li; and wherein M is MgX when the organometallic reagent (R$^{12}$M) is aryl-MgX or C1-C6-alkyl-MgX or MgX$_2$ or alkyl$_2$Mg or aryl$_2$Mg; and wherein X is a halogen;

(ii) followed by reacting said compound of formula (A'') with a compound of formula (B) or (C)

R$^9$CO$_2$R$^{13}$      (B)

R$^9$COCl      (C)

to form a compound of formula (A'),
wherein R$^{13}$ is C1-C6-alkyl, C1-C6-alkanoyl; or
wherein R$^9$ and R$^{13}$ together with the atoms to which they are attached form a 4 to 6-membered ring optionally substituted by C2-C6-alkenyl-aryl, C2-C12-alkenyl, C2-C12-alkynyl, C1-C12-alkyl, NH$_2$, N(H)(C1-C6-alkyl), N(C1-C6-alkyl)$_2$, C1-C12-alkoxy, C1-C12-hydroxyalkyl, halogen, CN, N$_3$, C1-C4-alkyl-CO$_2$H, C1-C4-alkyl-CO$_2$—C1-C6-alkyl, C(=O)H, C(=O)—C1-C6-alkyl and C1-C12-alkylthio ; or wherein R$^9$ and R$^{13}$ together with the atoms to which they are attached form a 4 to 6-membered ring fused to an aryl or heteraryl, wherein said aryl or heteraryl is optionally substituted by one or more groups independently selected from halogen atoms, CN, N$_3$, C1-C6-alkyl, [SO$_3$]$^-$, SO$_3$H, SO$_2$Cl, OH, C1-C6-alkoxy, C(=O)OH and C1-C6-alkoxycarbonyl, C1-C12-hydroxyalkyl, C1-C12-thio alkyl; (iii) addition of a protonic acid HA to form a compound of formula (A), wherein said HA is a suitable acid preferably selected from an inorganic acid or an organic acid, and wherein further preferably said inorganic acid is selected from HBr, HCl, HI, HBF$_4$, HPF$_6$ and HC1O$_4$, and said organic acid is selected from (C1-C5-alkyl)C(=O)OH, aryl-CH$_2$-C(=O)OH, [aryl-C(=O)OH, H$_3$PO$_4$, (C1-C6-alkyl)SO$_3$H, aryl-CH$_2$—SO$_3$H and aryl-SO$_3$H, and wherein again further preferably said inorganic acid is selected from HBr, HCl, HBF$_4$, HPF$_6$ and HClO$_4$, and said organic acid is selected from (C1-C6-alkyl)SO$_3$H.

In a preferred embodiment of the present inventive processes, the organometallic reagent (R$^{12}$M) is an organomagnesium reagent selected from aryl-MgX and C1-C6-alkyl-MgX, wherein X is a halogen. In another preferred embodiment, the organometallic reagent (R$^{12}$M) is an organomagnesium reagent selected from methylmagnesium chloride, methylmagnesium bromide, methylmagnesium iodide, ethylmagnesium chloride, ethylmagnesium bromide, ethylmagnesium iodide, iso-propylmagnesium chloride, iso-propylmagnesium bromide, iso-propylmagnesium iodide, phenylmagnesium chloride, phenylmagnesium bromide and phenylmagnesium iodide.

In a further preferred embodiment, the organometallic reagent (R$^{12}$M) is an organolithium reagent selected from aryl-Li and C1-C6-Li. In a preferred embodiment, the organometallic reagent (R$^{12}$M) is an organolithium reagent selected from n-butyllithium, sec-butyllithium, tert-butyllithium or phenyllithium. In a very preferred embodiment, the organometallic reagent (R$^{12}$M) is n-butyllithium.

In a further preferred embodiment, R$^{13}$ is C1-C6-alkyl, preferably C1-C5-alkyl, more preferably C1-C4-alkyl, more preferably C1-C3-alkyl most preferably ethyl or methyl. In a further preferred embodiment, R$^{13}$ is C1-C6-alkanoyl, preferably C1-C5-alkanoyl, more preferably C1-C4-alkanoyl, more preferably C1-C3-alkanoyl, most preferably C1-C2-alkanoyl.

In a further preferred embodiment, R$^9$ and R$^{13}$ together with the atoms to which they are attached form a 4 to 6-membered ring (i.e. α, β-, β- or δ-lactone).

In a further preferred embodiment, the compound of formula (A'') is reacted with a compound of formula (B) or (C), wherein said compound of formula (B) or (C) is selected from methyl benzoate, methyl-4-fluorobenzoate and methyl-4-methoxybenzoate, methyl naphthoate, methyl 2,4,6-trimethylbenzoate, (methoxycarbonyl)benzoic acid, methyl aminobenzoate, methyl hydroxylbenzoate, methyl mercaptobenzoate, phthalic anhydride, methyl 2,4,6-trimethylbenzoyl chloride, anthracene-9-carbonyl chloride.

In a preferred embodiment, R$^{11}$ is a hydrogen or a halogen selected from fluorine, chlorine, bromine and iodine, preferably chlorine, bromine and iodine, more preferably bromine and iodine, most preferably bromine.

In a preferred embodiment, said $R^{11}$ is hydrogen and said $R^8$ is selected from C1-C6-alkoxy, C1-C6-hydroxyalkyl, $O(CH_2)O(CH_3)$, $O(CH_2)O(CH_2)_2OCH_3$, $NH_2$, $N(H)(C1$-C6-alkyl), $N(C1$-C6-alkyl)$_2$, SH, F, $CF_3$, C1-C6-alkylthio, 4,4-dimethyl-4,5-dihydrooxazole, $NHCOR^9$, $NHCO_2R^9$, $OCNR_2$, $CONHR^9$, $CON(R^9)_2$, $C=NR^9$, $CO_2H$, $SO_3R^9$, $SO_3H$, $SO_2NC(CH_3)_3$, $SO_2N(R^9)_2$.

In a preferred embodiment, said $R^{11}$ is hydrogen and $R^8$ is selected from $O(C1$-C6-alkyl). In one embodiment said $R^{11}$ is hydrogen and said $R^8$ is selected $NH_2$, $N(H)(C1$-C6-alkyl) and $N(C1$-C6-alkyl)$_2$. In a preferred embodiment, said R" is hydrogen and said $R^8$ is $N(C1$-C6-alkyl)$_2$. In a further preferred embodiment, said R" is hydrogen and said $R^8$ is $N(C1$-C6-alkyl)$_2$, wherein said C1-C6-alkyl are independently selected from C1-C6-alkyl, C1-C5-alkyl, C1-C4-alkyl, C1-C3-alkyl, ethyl and methyl.

In a very preferred embodiment, said $R^{11}$ is hydrogen and said $R^8$ is OMe or F. In a further very preferred embodiment said $R^{11}$ is hydrogen and said $R^8$ is $NH_2$. In a further very preferred embodiment, said $R^{11}$ is hydrogen and said $R^8$ is $N(H)(C1$-C6-alkyl). In a preferred embodiment, said $R^{11}$ is hydrogen and said $R^8$ is $N(H)(C1$-C6-alkyl), wherein said C1-C6-alkyl is independently selected from C1-C6-alkyl, C1-C5-alkyl, C1-C4-alkyl, C1-C3-alkyl, ethyl and methyl.

In a very preferred embodiment, said $R^8$ is NHMe or NHEt.

In another preferred embodiment, said $R^{11}$ is halogen and said $R^8$ is selected from C1-C6-alkoxy, C1-C6-hydroxyalkyl, $O(CH_2)O(CH_3)$, $O(CH_2)O(CH_2)_2OCH_3$, $NH_2$, $N(H)(C1$-C6-alkyl), $N(C1$-C6-alkyl)$_2$, SH, F, $CF_3$, C1-C6-alkylthio, 4,4-dimethyl-4,5-dihydrooxazole, $NHCOR^9$, $NHCO_2R^9$, $OCNR_2$, $CONHR^9$, $CON(R^9)_2$, $C=NR^9$, $CO_2H$, $SO_3R^9$, $SO_3H$, $SO_2NC(CH_3)_3$, $SO_2N(R^9)_2$ and H.

In another preferred embodiment, said $R^{11}$ is halogen and said $R^8$ is selected from H and $N(C1$-C6-alkyl)$_2$.

In another preferred embodiment, said $R^{11}$ is halogen and said $R^8$ is selected $NH_2$, $N(H)(C1$-C6-alkyl) and $N(C1$-C6-alkyl)$_2$. In a preferred embodiment where $R^{11}$ is halogen, $R^8$ is $N(C1$-C6-alkyl)$_2$. In a further preferred embodiment, said $R^{11}$ is halogen and said $R^8$ is $N(C1$-C6-alkyl)$_2$, wherein said C1-C6-alkyl are independently selected from C1-C6-alkyl, C1-C5-alkyl, C1-C4-alkyl, C1-C3-alkyl, ethyl and methyl.

In a very preferred embodiment, said $R^{11}$ is halogen and said $R^8$ is H and $N(C1$-C6-alkyl)$_2$. In a preferred embodiment, said $R^{11}$ is halogen and said $R^8$ is $NH_2$. In another preferred embodiment, said $R^{11}$ is halogen and $R^8$ is $N(H)(C1$-C6-alkyl). In a preferred embodiment, said $R^{11}$ is halogen and said $R^8$ is $N(H)(C1$-C6-alkyl), wherein said C1-C6-alkyl is independently selected from C1-C6-alkyl, C1-C5-alkyl, C1-C4-alkyl, C1-C3-alkyl, ethyl and methyl. In a very preferred embodiment, said $R^8$ is NHMe or NHEt.

For the inventive processes, said addition of said protonic acid HA to form a compound of formula (A) can either be effected in situ or after isolation of said compound of formula (A').

Thus, in a preferred embodiment of the inventive processes of the present invention, said addition of said protonic acid HA to form a compound of formula (A) is effected in situ without isolation of said compound of formula (A'). In a preferred embodiment of the present invention, said process comprises the further step of isolating said compound of formula (A'), and preferably further comprising the step of purifying said compound of formula (A'). Thus, in a preferred embodiment of the present invention, said addition of said protonic acid HA to form a compound of formula (A) is effected after isolation of said compound of formula (A'). Further preferred embodiments correspond to the preferred embodiments of the inventive compound of formula (A).

In a further preferred embodiment, said $R^9$ and $R^{13}$ together with the atoms to which they are attached form a phthalide or phthalic anhydride optionally substituted by one or more groups independently selected from halogen atoms, CN, $N_3$, C1-C6-alkyl, $[SO_3]^-$, $SO_3H$, $SO_2Cl$, OH, C1-C6-alkoxy, $C(=O)OH$ and C1-C6-alkoxycarbonyl, C1-C12-hydroxyalkyl, C1-C12-thio alkyl.

In another aspect, the present invention provides a compound of formula (A''')

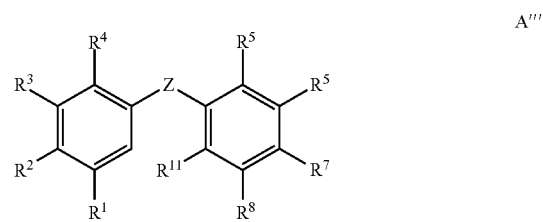

wherein $R^{11}$ and $R^1$ to $R^8$ and Z are as described herein.

In a very preferred embodiment, the compound of formula (A''') is 4-bromo-3-(3-methoxyphenoxy)-N,N-dimethylaniline or 3-(3-methoxyphenoxy)-N,N-dimethylaniline.

In a preferred embodiment (A1) $R^1$ is selected from C1-C6-alkoxy, aryloxy, O-alkyl-aryl, C1-C6-hydroxyalkyl, $O(CH_2)O(CH_3)$, $O(CH_2)O(CH_2)_2OCH_3$, $NH_2$, $N(H)(C1$-C6-alkyl), $N(C1$-C6-alkyl)$_2$, SH, F, $CF_3$, C1-C6-alkylthio, 4,4-dimethyl-4,5-dihydrooxazole, $NHCOR^{14}$, $NHCO_2R^{14}$, $OCNR^2$, $CONHR^{14}$, $CON(R^{14})_2$, $C=NR^{14}$, $CO_2H$, $[CO_2]^-$, $CO_2R^{14}$, $SO_3R^{14}$, $SO_3H$, $SO_2NC(CH_3)_3$, $[SO_3^-]$ and $SO_2N(R^{14})_2$; each of $R^2$, $R^3$, $R^4$ and $R^5$ is H; $R^6$ is selected from $NH_2$, $N(H)(C1$-C6-alkyl) and $N(C1$-C6-alkyl)$_2$; and $R^7$ and $R^8$ are both H.

In a preferred embodiment (A2) $R^1$ is selected from C1-C6-alkoxy, aryloxy, O-alkyl-aryl, C1-C6-hydroxyalkyl, $O(CH_2)O(CH_3)$, $O(CH_2)O(CH_2)_2OCH_3$, $NH_2$, $N(H)(C1$-C6-alkyl), $N(C1$-C6-alkyl)$_2$, SH, F, $CF_3$, C1-C6-alkylthio, 4,4-dimethyl-4,5-dihydrooxazole, $NHCOR^{14}$, $NHCO_2R^{14}$, $OCNR^2$, $CONHR^{14}$, $CON(R^{14})_2$, $C=NR^{14}$, $CO_2H$, $[CO_2^-]$, $CO_2R^{14}$, $SO_3R^{14}$, $SO_3H$, $SO_2NC(CH_3)_3$, $[SO_3]$, $SO_2N(R^{14})_2$; $R^5$ is H; $R^6$ is selected from $NH_2$, $N(H)(C1$-C6-alkyl) and $N(C1$-C6-alkyl)$_2$; $R^7$ is H; and $R^8$ is selected from C1-C6-alkoxy, aryloxy, O-alkyl-aryl, C1-C6-hydroxyalkyl, $O(CH_2)O(CH_3)$, $O(CH_2)O(CH_2)_2OCH_3$, $NH_2$, $N(H)(C1$-C6-alkyl), $N(C1$-C6-alkyl)$_2$, SH, F, $CF_3$, C1-C6-alkylthio, 4,4-dimethyl-4,5-dihydrooxazole, $NHCOR^{14}$, $NHCO_2R^{14}$, $OCNR^2$, $CONHR^{14}$, $CON(R^{14})_2$, $C=NR^{14}$, $CO_2H$, $[CO_2^-]$, $CO_2R^{14}$, $SO_3R^{14}$, $SO_3H$, $SO_2NC(CH_3)_3$ and $[SO_3]$, $SO_2N(R^{14})_2$.

In a preferred embodiment (A3) $R^1$ is selected from C1-C6-alkoxy, aryloxy, O-alkyl-aryl, C1-C6-hydroxyalkyl, $O(CH_2)O(CH_3)$, $O(CH_2)O(CH_2)_2OCH_3$, $NH_2$, $N(H)(C1$-C6-alkyl), $N(C1$-C6-alkyl)$_2$, SH, F, $CF_3$, C1-C6-alkylthio, 4,4-dimethyl-4,5-dihydrooxazole, $NHCOR^{14}$, $NHCO_2R^{14}$, $OCNR^2$, $CONHR^{14}$, $CON(R^{14})_2$, $C=NR^{14}$, $CO_2H$, $[CO_2^-]$, $CO_2R^{14}$, $SO_3R^{14}$, $SO_3H$, $SO_2NC(CH_3)_3$, $[SO_3^-]$ and $SO_2N(R^{14})_2$; $R^2$ is H; $R^3$ is selected from $NH_2$, $N(H)(C1$-C6-alkyl) and $N(C1$-C6-alkyl)$_2$; $R^4$ and $R^5$ are both H; $R^6$ is selected from $NH_2$, $N(H)(C1$-C6-alkyl) and $N(C1$-C6-alkyl)$_2$; $R^7$ is H; and $R^8$ is selected from C1-C6-alkoxy, aryloxy, O-alkyl-aryl, C1-C6-hydroxyalkyl, $O(CH_2)O(CH_3)$, $O(CH_2)O(CH_2)_2OCH_3$, $NH_2$, $N(H)(C1$-C6-alkyl), $N(C1$-C6-alkyl)

$_2$, SH, F, CF$_3$, C1-C6-alkylthio, 4,4-dimethyl-4,5-dihydrooxazole, NHCOR$^{14}$, NHCO$_2$R$^{14}$, OCNR$^2$, CONHR$^{14}$, CON(R$^{14}$)$_2$, C=NR$^{14}$, CO$_2$H, [CO$_2$$^-$], CO$_2$R$^{14}$, SO$_3$R$^{14}$, SO$_3$H, SO$_2$NC(CH$_3$)$_3$, [SO$_3$$^-$] and SO$_2$N(R$^{14}$)$_2$.

In a preferred embodiment (A4) R$^1$ is selected from C1-C6-alkoxy, aryloxy, O-alkyl-aryl, C1-C6-hydroxyalkyl, O(CH$_2$)O(CH$_3$), O(CH$_2$)O(CH$_2$)$_2$OCH$_3$, NH$_2$, N(H)(C1-C6-alkyl), N(C1-C6-alkyl)$_2$, SH, F, CF$_3$, C1-C6-alkylthio, 4,4-dimethyl-4,5-dihydrooxazole, NHCOR$^{14}$, NHCO$_2$R$^{14}$, OCNR$^2$, CONHR$^{14}$, CON(R$^{14}$)$_2$, C=NR$^{14}$, CO$_2$H, [CO$_2$$^-$], CO$_2$R$^{14}$, SO$_3$R$^{14}$, SO$_3$H, SO$_2$NC(CH$_3$)$_3$, [SO$_3$] and SO$_2$N(R$^{14}$)$_2$; each of R$^2$, R$^3$, R$^4$, R$^5$, R$^6$ and R$^7$ is H; and R$^8$ is selected from C1-C6-alkoxy, aryloxy, O-alkyl-aryl, C1-C6-hydroxyalkyl, O(CH$_2$)O(CH$_3$), O(CH$_2$)O(CH$_2$)$_2$OCH$_3$, NH$_2$, N(H)(C1-C6-alkyl), N(C1-C6-alkyl)$_2$, SH, F, CF$_3$, C1-C6-alkylthio, 4,4-dimethyl-4,5-dihydrooxazole, NHCOR$^{14}$, NHCO$_2$R$^{14}$, OCNR$^2$, CONHR$^{14}$, CON(R$^{14}$)$_2$, C=NR$^{14}$, CO$_2$H, [CO$_2$$^-$], CO$_2$R$^{14}$, SO$_3$R$^{14}$, SO$_3$H, SO$_2$NC(CH$_3$)$_3$, [SO$_3$$^-$] and SO$_2$N(R$^{14}$)$_2$;

In a very preferred embodiment (A5) R$^1$ is selected from C1-C6-alkoxy, O(CH$_2$)O(CH$_3$) and O(CH$_2$)O(CH$_2$)$_2$OCH$_3$; R$^2$, R$^3$, R$^4$ and R$^5$ is H; R$^6$ is selected from NH$_2$, N(H)(C1-C6-alkyl) and N(C1-C6-alkyl)$_2$; and R$^7$ and R$^8$ are both H.

In a very preferred embodiment (A6) R$^1$ is selected from C1-C6-alkoxy, O(CH$_2$)O(CH$_3$) and O(CH$_2$)O(CH$_2$)$_2$OCH$_3$; each of R$^2$, R$^3$, R$^4$ and R$^5$ is H; R$^6$ is selected from NH$_2$, N(H)(C1-C6-alkyl) and N(C1-C6-alkyl)$_2$; and R$^7$ is selected from H; R$^8$ is selected from C1-C6-alkoxy, O(CH$_2$)O(CH$_3$), O(CH$_2$)O(CH$_2$)$_2$OCH$_3$.

In a very preferred embodiment (A7) R$^1$ is selected from C1-C6-alkoxy, O(CH$_2$)O(CH$_3$) and O(CH$_2$)O(CH$_2$)$_2$OCH$_3$; R$^2$ is H; R$^3$ is selected from NH$_2$, N(H)(C1-C6-alkyl) and N(C1-C6-alkyl)$_2$; R$^4$ and R$^5$ are both H; R$^6$ is selected from NH$_2$, N(H)(C1-C6-alkyl) and N(C1-C6-alkyl)$_2$; R$^7$ is H; and R$^8$ is selected from C1-C6-alkoxy, O(CH$_2$)O(CH$_3$) and O(CH$_2$)O(CH$_2$)$_2$OCH$_3$;

In a very preferred embodiment (A8) R$^1$ is selected from C1-C6-alkoxy, O(CH$_2$)O(CH$_3$) and O(CH$_2$)O(CH$_2$)$_2$OCH$_3$; R$^2$, R$^3$, R$^4$, R$^5$, R$^6$ and R$^7$ is selected from H; and R$^8$ is selected from C1-C6-alkoxy, O(CH$_2$)O(CH$_3$) and O(CH$_2$)O(CH$_2$)$_2$OCH$_3$.

In a very preferred embodiment (A9) R$^1$ is OCH$_3$; each of R$^2$, R$^3$, R$^4$ and R$^5$ is H; R$^6$ is selected from N(CH$_3$)$_2$; and R$^7$ and R$^8$ are both H In a very preferred embodiment (A10) R$^1$ is OCH$_3$; each of R$^2$, R$^3$, R$^4$ and R$^5$ is H; R$^6$ is N(CH$_3$)$_2$; and R$^7$ is H; and R$^8$ is OCH$_3$.

In a very preferred embodiment (A11) R$^1$ is OCH$_3$; R$^2$ is H; R$^3$ is N(CH$_3$)$_2$; R$^4$ and R$^5$ are both H; R$^6$ is N(CH$_3$)$_2$; R$^7$ is H; and R$^8$ is OCH$_3$;

In a very preferred embodiment (A12) R$^1$ is selected from OCH$_3$; and each of R$^2$, R$^3$, R$^4$, R$^5$, R$^6$ and R$^7$ is H; R$^8$ is OCH$_3$.

In a further very preferred embodiment, in the embodiments (A1) to (A12) Z is Ne; and R$^9$, R$^{10}$, R$^{14}$ and A$^-$ are selected as defined above.

In a further very preferred embodiment, in the embodiments (A1) to (A12) Z is NR$^{10}$; and R$^9$ is selected from 2,4,6-trimethylbenezene, 2,6-dimethylbenzene and naphtyl; R$^{10}$ is phenyl or methyl; and R$^{14}$ and A are selected as defined above.

In a further very preferred embodiment, in the embodiments (A1) to (A12) Z is NR$^{10}$; R$^9$ is selected from 2,4,6-trimethylbenezene and 2,6-dimethylbenzene; R$^{10}$ is phenyl; and R$^{14}$ and A$^-$ are selected as defined above.

In a further very preferred embodiment, in the embodiments (A1) to (A12) Z is NR$^{10}$; R$^9$ is selected from trimethylbenzene and 2,6-dimethylbenzene; R$^{10}$ is methyl; and R$^{14}$ and A$^-$ are selected as defined above.

In a further very preferred embodiment, in the embodiments (A1) to (A12) Z is NR$^{10}$; R$^9$ is naphtyl; R$^{10}$ is phenyl; and R$^{14}$ and A are selected as defined above.

In a further very preferred embodiment, in the embodiments (A1) to (A12) Z is NR'$^{\circ}$ ;

R$^9$ is naphtyl; R$^{10}$ is methyl; and R$^{14}$ and A are selected as defined above.

In a further very preferred embodiment, in the embodiments (A1) to (A12) Z is Ne; R$^9$ is phenyl; R$^{10}$ is phenyl; and R$^{14}$ and A are selected as defined above.

In a further very preferred embodiment, in the embodiments (A1) to (A12) Z is Ne; R$^9$ is phenyl; R$^{10}$ is methyl; and R$^{14}$ and A are selected as defined above.

In a preferred embodiment (Bl) R$^1$ is selected from C1-C6-alkoxy, aryloxy, O-alkyl-aryl, C1-C6-hydroxyalkyl, O(CH$_2$)O(CH$_3$), O(CH$_2$)O(CH$_2$)$_2$OCH$_3$, NH$_2$, N(H)(C1-C6-alkyl), N(C1-C6-alkyl)$_2$, SH, F, CF$_3$, C1-C6-alkylthio, 4,4-dimethyl-4,5-dihydrooxazole, NHCOR$^{14}$, NHCO$_2$R$^{14}$, OCNR$^2$, CONHR$^{14}$, CON(R$^{14}$)$_2$, C=NR$^{14}$, CO$_2$H, [CO$_2$$^-$], CO$_2$R$^{14}$, SO$_3$R$^{14}$, SO$_3$H, SO$_2$NC(CH$_3$)$_3$ and [SO$_3$], SO$_2$N(R$^{14}$)$_2$; each of R$^2$, R$^3$, R$^4$ and R$^5$ is selected from H; R$^6$ is selected from NH$_2$, N(H)(C1-C6-alkyl) and N(C1-C6-alkyl)$_2$; and R$^7$ and R$^8$ are both H.

In a preferred embodiment (B2) R$^1$ is selected from C1-C6-alkoxy, aryloxy, O-alkyl-aryl, C1-C6-hydroxyalkyl, O(CH$_2$)O(CH$_3$), O(CH$_2$)O(CH$_2$)$_2$OCH$_3$, NH$_2$, N(H)(C1-C6-alkyl), N(C1-C6-alkyl)$_2$, SH, F, CF$_3$, C1-C6-alkylthio, 4,4-dimethyl-4,5-dihydrooxazole, NHCOR$^{14}$, NHCO$_2$R$^{14}$, OCNR$^2$, CONHR$^{14}$, CON(R$^{14}$)$_2$, C=NR$^{14}$, CO$_2$H, [CO$_2$$^-$], CO$_2$R$^{14}$, SO$_3$R$^{14}$, SO$_3$H, SO$_2$NC(CH$_3$)$_3$ and [SO$_3$], SO$_2$N(R$^{14}$)$_2$; each of R$^2$, R$^3$, R$^4$, R$^5$ and R$^6$ is H; R$^7$ is selected from NH$_2$, N(H)(C1-C6-alkyl) and N(C1-C6-alkyl)$_2$; and R$^8$ is selected from H.

In a preferred embodiment (B3) R$^1$ is selected from C1-C6-alkoxy, aryloxy, O-alkyl-aryl, C1-C6-hydroxyalkyl, O(CH$_2$)O(CH$_3$), O(CH$_2$)O(CH$_2$)$_2$OCH$_3$, NH$_2$, N(H)(C1-C6-alkyl), N(C1-C6-alkyl)$_2$, SH, F, CF$_3$, C1-C6-alkylthio, 4,4-dimethyl-4,5-dihydrooxazole, NHCOR$^{14}$, NHCO$_2$R$^{14}$, OCNR$^2$, CONHR$^{14}$, CON(R$^{14}$)$_2$, C=NR$^{14}$, CO$_2$H, [CO$_2$$^-$], CO$_2$R$^{14}$, SO$_3$R$^{14}$, SO$_3$H, SO$_2$NC(CH$_3$)$_3$, [SO$_3$$^-$] and SO$_2$N(R$^{14}$)$_2$; R$^2$ is selected from H; R$^3$ is selected from NH$_2$, N(H)(C1-C6-alkyl) and N(C1-C6-alkyl)$_2$; R$^4$ and R$^5$ are both H; R$^6$ is selected from NH$_2$, N(H)(C1-C6-alkyl) and N(C1-C6-alkyl)$_2$; R$^7$ is H; and R$^8$ is selected from C1-C6-alkoxy, aryloxy, O-alkyl-aryl, C1-C6-hydroxyalkyl, O(CH$_2$)O(CH$_3$), O(CH$_2$)O(CH$_2$)$_2$OCH$_3$, NH$_2$, N(H)(C1-C6-alkyl), N(C1-C6-alkyl)$_2$, SH, F, CF$_3$, C1-C6-alkylthio, 4,4-dimethyl-4,5-dihydrooxazole, NHCOR$^{14}$, NHCO$_2$R$^{14}$, OCNR$^2$, CONHR$^{14}$, CON(R$^{14}$)$_2$, C=NR$^{14}$$_5$ CO$_2$H, [CO$_2$ ], CO$_2$R$^{14}$, SO$_3$R$^{14}$, SO$_3$H, SO$_2$NC(CH$_3$)$_3$, [SO$_3$$^-$] and SO$_2$N(R$^{14}$)$_2$;

In a very preferred embodiment (B4) R$^1$ is selected from C1-C6-alkoxy, O(CH$_2$)O(CH$_3$) and O(CH$_2$)O(CH$_2$)$_2$OCH$_3$; each of R$^2$, R$^3$, R$^4$ and R$^5$ is H; R$^6$ is selected from NH$_2$, N(H)(C1-C6-alkyl) and N(C1-C6-alkyl)$_2$; and R$^7$ and R$^8$ are both H.

In a very preferred embodiment (B5) R$^1$ is selected from C1-C6-alkoxy, O(CH$_2$)O(CH$_3$) and O(CH$_2$)O(CH$_2$)$_2$OCH$_3$; each of R$^2$, R$^3$, R$^4$, R$^5$ and R$^6$ is H; R$^7$ is selected from NH$_2$, N(H)(C1-C6-alkyl) and N(C1-C6-alkyl)$_2$; and R$^8$ is H.

In a very preferred embodiment (B6) R$^1$ is selected from C1-C6-alkoxy, O(CH$_2$)O(CH$_3$) and O(CH$_2$)O(CH$_2$)$_2$OCH$_3$; R$^2$ is H; R$^3$ is selected from NH$_2$, N(H)(C1-C6-alkyl) and N(C1-C6-alkyl)$_2$; R$^4$ and R$^5$ are both H; R$^6$ is selected from $NH_2$, $N(H)(C1-C6\text{-alkyl})$ and $N(C1-C6\text{-alkyl})_2$; and $R^7$ is H; $R^8$ is selected from C1-C6-alkoxy, $O(CH_2)O(CH_3)$ and $O(CH_2)O(CH_2)_2OCH_3$;

In a very preferred embodiment (B7) $R^1$ is $OCH_3$; each of $R^2$, $R^3$, $R^4$, $R^5$ is H; $R^6$ is $N(CH_3)_2$; and $R^7$, $R^8$ are both H.

In a very preferred embodiment (B8) $R^1$ is $OCH_3$; each of $R^2$, $R^3$, $R^4$, $R^5$ and $R^6$ is H; and $R^7$ is $N(CH_3)_2$; and $R^8$ is selected from H.

In a very preferred embodiment (B9) $R^1$ is $OCH_3$; $R^2$ is H; $R^3$ is $N(CH_3)_2$; $R^4$ and $R^5$ are both H; $R^6$ is $N(CH_3)_2$; and $R^7$ is H; and $R^8$ is selected from $OCH_3$.

In a further very preferred embodiment, in the embodiments (B1) to (B9) Z is $NR^{10}$; and $R^9$, $R^{10}$, $R^{14}$ and $A^-$ are selected as defined above.

In a further very preferred embodiment, in the embodiments (B1) to (B9) Z is $NR^{10}$; and $R^9$ is selected from 2,4,6-trimethylbenezene, 2,6-dimethylbenzene and naphtyl; $R^{10}$ is phenyl or methyl; and $R^{14}$ and $A^-$ are selected as defined above.

In a further very preferred embodiment, in the embodiments (B1) to (B9) Z is $NR^{10}$; $R^9$ is selected from 2,4,6-trimethylbenezene and 2,6-dimethylbenzene; $R^{10}$ is phenyl; and $R^{14}$ and $A^-$ are selected as defined above.

In a further very preferred embodiment, in the embodiments (B1) to (B9) Z is $NR^{10}$; $R^9$ is selected from trimethylbenzene and 2,6-dimethylbenzene; $R^{10}$ is methyl; and $R^{14}$ and A are selected as defined above.

In a further very preferred embodiment, in the embodiments (B1) to (B9) Z is $NR^{10}$; $R^9$ is naphtyl; $R^{10}$ is phenyl; and $R^{14}$ and A are selected as defined above.

In a further very preferred embodiment, in the embodiments (B1) to (B9) Z is $NR^{10}$; $R^9$ is naphtyl; $R^{10}$ is methyl; and $R^{14}$ and $A^-$ are selected as defined above.

In a further very preferred embodiment, in the embodiments (B1) to (B9) Z is $NR^{10}$; $R^9$ is phenyl; $R^{10}$ is phenyl; and $R^{14}$ and A are selected as defined above.

In a further very preferred embodiment, in the embodiments (B1) to (B9) Z is $NR^{10}$; $R^9$ is phenyl; $R^{10}$ is methyl; and $R^{14}$ and A are selected as defined above.

In a preferred embodiment (C1) $R^1$ is selected from C1-C6-alkoxy, aryloxy, O-alkyl-aryl, C1-C6-hydroxyalkyl, $O(CH_2)O(CH_3)$, $O(CH_2)O(CH_2)_2OCH_3$, $NH_2$, $N(H)(C1\text{-}C6\text{-alkyl})$, $N(C1\text{-}C6\text{-alkyl})_2$, SH, F, $CF_3$, C1-C6-alkylthio, 4,4-dimethyl-4,5-dihydrooxazole, $NHCOR^{14}$, $NHCO_2R^{14}$, $OCNR^2$, $CONHR^{14}$, $CON(R^{14})_2$, $C=NR^{14}$, $CO_2H$, $[CO_2^-]$, $CO_2R^{14}$, $SO_3R^{14}$, $SO_3H$, $SO_2NC(CH_3)_3$, $[SO_3^-]$ and $SO_2N(R^{14})_2$; each of $R^2$, $R^3$, $R^4$ and $R^5$ is H; $R^6$ is selected from $NH_2$, $N(H)(C1\text{-}C6\text{-alkyl})$ and $N(C1\text{-}C6\text{-alkyl})_2$; and $R^7$ and $R^8$ are both H.

In a preferred embodiment (C2) $R^1$ is selected from C1-C6-alkoxy, aryloxy, O-alkyl-aryl, C1-C6-hydroxyalkyl, $O(CH_2)O(CH_3)$, $O(CH_2)O(CH_2)_2OCH_3$, $NH_2$, $N(H)(C1\text{-}C6\text{-alkyl})$, $N(C1\text{-}C6\text{-alkyl})_2$, SH, F, $CF_3$, C1-C6-alkylthio, 4,4-dimethyl-4,5-dihydrooxazole, $NHCOR^{14}$, $NHCO_2R^{14}$, $OCNR^2$, $CONHR^{14}$, $CON(R^{14})_2$, $C=NR^{14}$, $CO_2H$, $[CO_2^-]$, $CO_2R^{14}$, $SO_3R^{14}$, $SO_3H$, $SO_2NC(CH_3)_3$, $[SO_3]$ and $SO_2N(R^{14})_2$; and each of $R^2$, $R^3$, $R^4$, $R^5$, $R^6$, $R^7$, $R^8$ is H.

In a preferred embodiment (C3) $R^1$ is selected from C1-C6-alkoxy, aryloxy, O-alkyl-aryl, C1-C6-hydroxyalkyl, $O(CH_2)O(CH_3)$, $O(CH_2)O(CH_2)_2OCH_3$, $NH_2$, $N(H)(C1\text{-}C6\text{-alkyl})$, $N(C1\text{-}C6\text{-alkyl})_2$, SH, F, $CF_3$, C1-C6-alkylthio, 4,4-dimethyl-4,5-dihydrooxazole, $NHCOR^{14}$, $NHCO_2R^{14}$, $OCNR^2$, $CONHR^{14}$, $CON(R^{14})_2$, $C=NR^{14}$, $CO_2H$, $[CO_2^-]$, $CO_2R^{14}$, $SO_3R^{14}$, $SO_3H$, $SO_2NC(CH_3)_3$, $[SO_3^-]$ and $SO_2N(R^{14})_2$; each of $R^2$, $R^3$, $R^4$ and $R^5$ is H; $R^6$ is selected from $NH_2$, $N(H)(C1\text{-}C6\text{-alkyl})$ and $N(C1\text{-}C6\text{-alkyl})_2$; $R^7$ is H; and $R^8$ is selected from C1-C6-alkoxy, aryloxy, O-alkyl-aryl, C1-C6-hydroxyalkyl, $O(CH_2)O(CH_3)$, $O(CH_2)O(CH_2)_2OCH_3$, $NH_2$, $N(H)(C1\text{-}C6\text{-alkyl})$, $N(C1\text{-}C6\text{-alkyl})_2$, SH, F, $CF_3$, C1-C6-alkylthio, 4,4-dimethyl-4,5-dihydrooxazole, $NHCOR^{14}$, $NHCO_2R^{14}$, $OCNR^2$, $CONFIR^{14}$, $CON(R^{14})_{25}$ $C=NR^{14}$, $CO_2H$, $[CO_2]$, $CO_2R^{14}$, $SO_3R^{14}$, $SO_3H$, $SO_2NC(CH_3)_3$, $[SO_3]$ and $SO_2N(R^{14})_2$;

In a preferred embodiment (C4) $R^1$ is selected from C1-C6-alkoxy, aryloxy, O-alkyl-aryl, C1-C6-hydroxyalkyl, $O(CH_2)O(CH_3)$, $O(CH_2)O(CH_2)_2OCH_3$, $NH_2$, $N(H)(C1\text{-}C6\text{-alkyl})$, $N(C1\text{-}C6\text{-alkyl})_2$, SH, F, $CF_3$, C1-C6-alkylthio, 4,4-dimethyl-4,5-dihydrooxazole, $NHCOR^{14}$, $NHCO_2R^{14}$, $OCNR^2$, $CONHR^{14}$, $CON(R^{14})_2$, $C=NR^{14}$, $CO_2H$, $[CO_2^-]$, $CO_2R^{14}$, $SO_3R^{14}$, $SO_3H$, $SO_2NC(CH_3)_3$, $[SO_3^-]$ and $SO_2N(R^{14})_2$; $R^2$ is H; $R^3$ is selected from $NH_2$, $N(H)(C1\text{-}C6\text{-alkyl})$ and $N(C1\text{-}C6\text{-alkyl})_2$; $R^4$ and $R^5$ are both H; $R^6$ is selected from $NH_2$, $N(H)(C1\text{-}C6\text{-alkyl})$ and $N(C1\text{-}C6\text{-alkyl})_2$; $R^7$ is H; and $R^8$ is selected from C1-C6-alkoxy, aryloxy, O-alkyl-aryl, C1-C6-hydroxyalkyl, $O(CH_2)O(CH_3)$, $O(CH_2)O(CH_2)_2OCH_3$, $NH_2$, $N(H)(C1\text{-}C6\text{-alkyl})$, $N(C1\text{-}C6\text{-alkyl})_2$, SH, F, $CF_3$, C1-C6-alkylthio, 4,4-dimethyl-4,5-dihydrooxazole, $NHCOR^{14}$, $NHCO_2R^{14}$, $OCNR^2$, $CONHR^{14}$, $CON(R^{14})_2$, $C=NR^{14}$, $CO_2H$, $[CO_2^-]$, $CO_2R^{14}$, $SO_3R^{14}$, $SO_3H$, $SO_2NC(CH_3)_3$, $[SO_3^-]$ and $SO_2N(R^{14})_2$.

In a very preferred embodiment (C5) $R^1$ is selected from C1-C6-alkoxy, $O(CH_2)O(CH_3)$ and $O(CH_2)O(CH_2)_2OCH_3$; each of $R^2$, $R^3$, $R^4$ and $R^5$ is H; $R^6$ is selected from $NH_2$, $N(H)(C1\text{-}C6\text{-alkyl})$ and $N(C1\text{-}C6\text{-alkyl})_2$; and $R^7$ and $R^8$ are both H.

In a very preferred embodiment (C6) $R^1$ is selected from C1-C6-alkoxy, $O(CH_2)O(CH_3)$ and $O(CH_2)O(CH_2)_2OCH_3$; and each of $R^2$, $R^3$, $R^4$, $R^5$, $R^6$, $R^7$ and $R^8$ is H.

In a very preferred embodiment (C7) $R^1$ is selected from C1-C6-alkoxy, $O(CH_2)O(CH_3)$ and $O(CH_2)O(CH_2)_2OCH_3$; each of $R^2$, $R^3$, $R^4$ and $R^5$ is H; $R^6$ is selected from $NH_2$, $N(H)(C1\text{-}C6\text{-alkyl})$ and $N(C1\text{-}C6\text{-alkyl})_2$; and $R^7$ is H; and $R^8$ is selected from C1-C6-alkoxy, $O(CH_2)O(CH_3)$ and $O(CH_2)O(CH_2)_2OCH_3$.

In a very preferred embodiment (C8) $R^1$ is selected from C1-C6-alkoxy, $O(CH_2)O(CH_3)$ and $O(CH_2)O(CH_2)_2OCH_3$; $R^2$ is H; $R^3$ is selected from $NH_2$, $N(H)(C1\text{-}C6\text{-alkyl})$ and $N(C1\text{-}C6\text{-alkyl})_2$; $R^4$ and $R^5$ are both H; $R^6$ is selected from $NH_2$, $N(H)(C1\text{-}C6\text{-alkyl})$ and $N(C1\text{-}C6\text{-alkyl})_2$; $R^7$ is H; and $R^8$ is selected from C1-C6-alkoxy, $O(CH_2)O(CH_3)$ and $O(CH_2)O(CH_2)_2OCH_3$.

In a very preferred embodiment (C9) $R^1$ is $OCH_3$; each of $R^2$, $R^3$, $R^4$ and $R^5$ is H; $R^6$ is $N(CH_3)_2$; and $R^7$ and $R^8$ are both H.

In a very preferred embodiment (C10) $R^1$ is $OCH_3$; and each of $R^2$, $R^3$, $R^4$, $R^5$, $R^6$, $R^7$, and $R^8$ is H.

In a very preferred embodiment (C11) $R^1$ is $OCH_3$; each of $R^2$, $R^3$, $R^4$ and $R^5$ is H; $R^6$ is $N(CH_3)_2$; $R^7$ is H; and $R^8$ is $OCH_3$.

In a very preferred embodiment (C12) $R^1$ is $OCH_3$; $R^2$ is H; $R^3$ is $N(CH_3)_2$; $R^4$ and $R^5$ are both H; $R^6$ is $N(CH_3)_2$; $R^7$ is H; and $R^8$ is $OCH_3$.

In a further very preferred embodiment, in the embodiments (C1) to (C12) Z is Ne; and $R^9$, $R^{10}$, $R^{14}$ and $A^-$ are selected as defined above.

In a further very preferred embodiment, in the embodiments (C1) to (C12) Z is $NR^{10}$; and $R^9$ is selected from 2,6-dimethylbenzene, naphtyl, 2,4,6-trimethylbenezene and phenyl; $R^{10}$ is phenyl or methyl; and $R^{14}$ and $A^-$ are selected as defined above.

In a further very preferred embodiment, in the embodiments (C1) to (C12) Z is $NR^{10}$; $R^9$ is 2,6-dimethylbenzene; $R^{10}$ is phenyl; and $R^{14}$ and $A^-$ are selected as defined above.

In a further very preferred embodiment, in the embodiments (C1) to (C12) Z is $NR^{10}$; $R^9$ is 2,6-dimethylbenzene; $R^{10}$ is methyl; and $R^{14}$ and $A^-$ are selected as defined above.

In a further very preferred embodiment, in the embodiments (C1) to (C12) Z is $NR^{10}$; $R^9$ is naphtyl; $R^{10}$ is phenyl; and $R^{14}$ and $A^-$ are selected as defined above.

In a further very preferred embodiment, in the embodiments (C1) to (C12) Z is $NR^{10}$; $R^9$ is naphtyl; $R^{10}$ is methyl; and $R^{14}$ and $A^-$ are selected as defined above.

In a further very preferred embodiment, in the embodiments (C1) to (C12) Z is $NR'^{o}$; $R^9$ is 2,4,6-trimethylbenezene and; $R^{10}$ is phenyl; and $R^{14}$ and $A^-$ are selected as defined above.

In a further very preferred embodiment, in the embodiments (C1) to (C12) Z is $NR^{10}$; $R^9$ is 2,4,6-trimethylbenezene; $R^{10}$ is methyl; and $R^{14}$ and $A^-$ are selected as defined above.

In a further very preferred embodiment, in the embodiments (C1) to (C12) Z is $NR^{10}$; $R^9$ is phenyl; $R^{10}$ is phenyl; and $R^{14}$ and A are selected as defined above.

In a further very preferred embodiment, in the embodiments (C1) to (C12) Z is $NR^{10}$; $R^9$ is phenyl; $R'''$ is methyl; and $R^{14}$ and $A^-$ are selected as defined above.

In a preferred embodiment (D1) $R^1$ is selected from C1-C6-alkoxy, aryloxy, O-alkyl-aryl, C1-C6-hydroxyalkyl, $O(CH_2)O(CH_3)$, $O(CH_2)O(CH_2)_2OCH_3$, $NH_2$, $N(H)(C1-C6-alkyl)$, $N(C1-C6-alkyl)_2$, SH, F, $CF_3$, C1-C6-alkylthio, 4,4-dimethyl-4,5-dihydrooxazole, $NHCOR^{14}$, $NHCO_2R^{14}$, $OCNR^2$, $CONHR^{14}$, $CON(R^{14})_2$, $C=NR^{14}$, $CO_2H$, $[CO_2^-]$, $CO_2R^{14}$, $SO_3R^{14}$, $SO_3H$, $SO_2NC(CH_3)_3$, $[SO_3^-]$ and $SO_2N(R^{14})_2$; each of $R^2$, $R^3$, $R^4$ and $R^5$ is H; $R^6$ is selected from $NH_2$, $N(H)(C1-C6-alkyl)$ and $N(C1-C6-alkyl)_2$; and $R^7$ and $R^8$ are both H.

In a preferred embodiment (D2) $R^1$ is selected from C1-C6-alkoxy, aryloxy, O-alkyl-aryl, C1-C6-hydroxyalkyl, $O(CH_2)O(CH_3)$, $O(CH_2)O(CH_2)_2OCH_3$, $NH_2$, $N(H)(C1-C6-alkyl)$, $N(C1-C6-alkyl)_2$, SH, F, $CF_3$, C1-C6-alkylthio, 4,4-dimethyl-4,5-dihydrooxazole, $NHCOR^{14}$, $NHCO_2R^{14}$, $OCNR^2$, $CONHR^{14}$, $CON(R^{14})_2$, $C=NR^{14}$, $CO_2H$, $[CO_2^-]$, $CO_2R^{14}$, $SO_3R^{14}$, $SO_3H$, $SO_2NC(CH_3)_3$, $[SO_3^-]$ and $SO_2N(R^{14})_2$; and each of $R^2$, $R^3$, $R^4$, $R^5$, $R^6$, $R^7$ and $R^8$ is H.

In a preferred embodiment (D3) $R^1$ is selected from C1-C6-alkoxy, aryloxy, O-alkyl-aryl, C1-C6-hydroxyalkyl, $O(CH_2)O(CH_3)$, $O(CH_2)O(CH_2)_2OCH_3$, $NH_2$, $N(H)(C1-C6-alkyl)$, $N(C1-C6-alkyl)_2$, SH, F, $CF_3$, C1-C6-alkylthio, 4,4-dimethyl-4,5-dihydrooxazole, $NHCOR^{14}$, $NHCO_2R^{14}$, $OCNR^2$, $CONHR^{14}$, $CON(R^{14})_2$, $C=NR^{14}$, $CO_2H$, $[CO_2^-]$, $CO_2R^{14}$, $SO_3R^{14}$, $SO_3H$, $SO_2NC(CH_3)_3$, $[SO_3^-]$ and $SO_2N(R^{14})_2$; $R^2$ is H; $R^3$ is selected from $NH_2$, $N(H)(C1-C6-alkyl)$ and $N(C1-C6-alkyl)_2$; $R^4$ and $R^5$ are both H; $R^6$ is selected from $NH_2$, $N(H)(C1-C6-alkyl)$ and $N(C1-C6-alkyl)_2$; $R^7$ is H; and $R^8$ is selected from C1-C6-alkoxy, aryloxy, O-alkyl-aryl, C1-C6-hydroxyalkyl, $O(CH_2)O(CH_3)$, $O(CH_2)O(CH_2)_2OCH_3$, $NH_2$, $N(H)(C1-C6-alkyl)$, $N(C1-C6-alkyl)_2$, SH, F, $CF_3$, C1-C6-alkylthio, 4,4-dimethyl-4,5-dihydrooxazole, $NHCOR^{14}$, $NHCO_2R^{14}$, $OCNR^2$, $CONHR^{14}$, $CON(R^{14})_2$, $C=NR^{14}$, $CO_2H$, $[CO_2^-]$, $CO_2R^{14}$, $SO_3R^{14}$, $SO_3H$, $SO_2NC(CH_3)_3$, $[SO_3]$ and $SO_2N(R^{14})_2$.

In a preferred embodiment (D4) $R^1$ is selected from C1-C6-alkoxy, aryloxy, O-alkyl-aryl, C1-C6-hydroxyalkyl, $O(CH_2)O(CH_3)$, $O(CH_2)O(CH_2)_2OCH_3$, $NH_2$, $N(H)(C1-C6-alkyl)$, $N(C1-C6-alkyl)_2$, SH, F, $CF_3$, C1-C6-alkylthio, 4,4-dimethyl-4,5-dihydrooxazole, $NHCOR^{14}$, $NHCO_2R^{14}$, $OCNR^2$, $CONHR^{14}$, $CON(R^{14})_2$, $C=NR^{14}$, $CO_2H$, $[CO_2^-]$, $CO_2R^{14}$, $SO_3R^{14}$, $SO_3H$, $SO_2NC(CH_3)_3$, $[SO_3^-]$ and $SO_2N(R^{14})_2$; each of $R^2$, $R^3$, $R^4$ and $R^5$ is H; $R^6$ is selected from $NH_2$, $N(H)(C1-C6-alkyl)$ and $N(C1-C6-alkyl)_2$; $R^7$ is H; $R^8$ is selected from C1-C6-alkoxy, aryloxy, O-alkyl-aryl, C1-C6-hydroxyalkyl, $O(CH_2)O(CH_3)$, $O(CH_2)O(CH_2)_2OCH_3$, $NH_2$, $N(H)(C1-C6-alkyl)$, $N(C1-C6-alkyl)_2$, SH, F, $CF_3$, C1-C6-alkylthio, 4,4-dimethyl-4,5-dihydrooxazole, $NHCOR^{14}$, $NHCO_2R^{14}$, $OCNR^2$, $CONHR^{14}$, $CON(R^{14})_2$, $C=NR^{14}$, $CO_2H$, $[CO_2^-]$, $CO_2R^{14}$, $SO_3R^{14}$, $SO_3H$, $SO_2NC(CH_3)_3$, $[SO_3^-]$ and $SO_2N(R^{14})_2$.

In a very preferred embodiment (D5) $R^1$ is selected from C1-C6-alkoxy, $O(CH_2)O(CH_3)$ and $O(CH_2)O(CH_2)_2OCH_3$; each of $R^2$, $R^3$, $R^4$ and $R^5$ is H; $R^6$ is selected from $NH_2$, $N(H)(C1-C6-alkyl)$ and $N(C1-C6-alkyl)_2$; and $R^7$ and $R^8$ are both H.

In a very preferred embodiment (D6) $R^1$ is selected from C1-C6-alkoxy, $O(CH_2)O(CH_3)$, $O(CH_2)O(CH_2)_2OCH_3$; and each of $R^2$, $R^3$, $R^4$, $R^5$, $R^6$, $R^7$ and $R^8$ is H.

In a very preferred embodiment (D7) $R^1$ is selected from C1-C6-alkoxy, $O(CH_2)O(CH_3)$ and $O(CH_2)O(CH_2)_2OCH_3$; $R^2$ is H; $R^3$ is selected from $NH_2$, $N(H)(C1-C6-alkyl)$ and $N(C1-C6-alkyl)_2$; $R^4$ and $R^5$ are both H; $R^6$ is selected from $NH_2$, $N(H)(C1-C6-alkyl)$ and $N(C1-C6-alkyl)_2$; $R^7$ is H; and $R^8$ is selected from C1-C6-alkoxy, $O(CH_2)O(CH_3)$ and $O(CH_2)O(CH_2)_2OCH_3$.

In a very preferred embodiment (D8) $R^1$ is selected from C1-C6-alkoxy, $O(CH_2)O(CH_3)$ and $O(CH_2)O(CH_2)_2OCH_3$; each of $R^2$, $R^3$, $R^4$ and $R^5$ is H; $R^6$ is selected from $NH_2$, $N(H)(C1-C6-alkyl)$ and $N(C1-C6-alkyl)_2$; $R^7$ is H; and $R^8$ is selected from C1-C6-alkoxy, $O(CH_2)O(CH_3)$ and $O(CH_2)O(CH_2)_2OCH_3$.

In a very preferred embodiment (D9) $R^1$ is $OCH_3$; each of $R^2$, $R^3$, $R^4$ and $R^5$ is H; $R^6$ is $N(CH_3)_2$; and $R^7$ and $R^8$ are both H.

In a very preferred embodiment (D10) $R^1$ is $OCH_3$; and each of $R^2$, $R^3$, $R^4$, $R^5$, $R^6$, $R^7$ and $R^8$ is H.

In a very preferred embodiment (D11) $R^1$ is $OCH_3$; $R^2$ is H; $R^3$ is $N(CH_3)_2$; $R^4$ and $R^5$ are both H; $R^6$ is $N(CH_3)_2$; $R^7$ is H; and $R^8$ is $OCH_3$;

In a very preferred embodiment (D12) $R^1$ is $OCH_3$; each of $R^2$, $R^3$, $R^4$ and $R^5$ is H; $R^6$ is $N(CH_3)_2$; $R^7$ is H; and $R^8$ is $OCH_3$.

In a further very preferred embodiment, in the embodiments (D1) to (D12) Z is Ne; and $R^9$, $R^{10}$, $R^{14}$ and $A^-$ are selected as defined above.

In a further very preferred embodiment, in the embodiments (D1) to (D12) Z is Ne; and $R^9$ is selected from 2,6-dimethylbenzene, naphtyl, 2,4,6-trimethylbenezene and phenyl; $R^{10}$ is phenyl or methyl; and $R^{14}$ and $A^-$ is selected as defined above.

In a further very preferred embodiment, in the embodiments (D1) to (D12) Z is Ne; $R^9$ is 2,4,6-trimethylbenezene and; $R^{10}$ is phenyl; and $R^{14}$ and $A^-$ are selected as defined above.

In a further very preferred embodiment, in the embodiments (D1) to (D12) Z is Ne; $R^9$ is 2,4,6-trimethylbenezene; $R^{10}$ is methyl; and $R^{14}$ and $A^-$ are selected as defined above.

In a further very preferred embodiment, in the embodiments (D1) to (D12) Z is $NR^{10}$; $R^9$ is naphtyl; is phenyl; and $R^{14}$ and A are selected as defined above.

In a further very preferred embodiment, in the embodiments (D1) to (D12) Z is $NR^{10}$; $R^9$ is naphtyl; $R^{10}$ is methyl; and $R^{14}$ and $A^-$ are selected as defined above.

In a further very preferred embodiment, in the embodiments (D1) to (D12) Z is $NR^{10}$; $R^9$ is 2,6-dimethylbenzene; $R^{10}$ is phenyl; and $R^{14}$ and $A^-$ are selected as defined above.

In a further very preferred embodiment, in the embodiments (D1) to (D12) Z is $NR^{10}$; $R^9$ is 2,6-dimethylbenzene; $R^{10}$ is methyl; and $R^{14}$ and $A^-$ are selected as defined above.

In a further very preferred embodiment, in the embodiments (D1) to (D12) Z is $NR^{10}$; $R^9$ is phenyl; $R^{10}$ is phenyl; and $R^{14}$ and $A^-$ are selected as defined above.

In a further very preferred embodiment, in the embodiments (D1) to (D12) Z is $NR^{10}$; $R^9$ is phenyl; $R^{10}$ is methyl; and $R^{14}$ and $A^-$ are selected as defined above.

In a further very preferred embodiment, said $R^1$ is the same as $R^8$. In a further very preferred embodiment, said $R^2$ is the same as $R^7$. In a further very preferred embodiment, said $R^3$ is the same as $R^6$.

Further very preferred embodiments of the present invention, in particular of the compounds of formula (A) are non-symmetrical substitution patterns. In a further very preferred embodiment, said $R^1$ is not the same as $R^8$. In a further very preferred embodiment, said $R^2$ is not the same as $R^7$. In a further very preferred embodiment, said $R^3$ is not the same as $R^6$. In a further very preferred embodiment, said $R^1$ is not the same as $R^8$, and said $R^2$ is not the same as $R^7$. In a further very preferred embodiment, said $R^1$ is not the same as $R^8$, and said $R^2$ is not the same as $R^7$, and said $R^3$ is not the same as $R^6$. In a further very preferred embodiment, said $R^1$ is not the same as $R^8$, and said $R^2$ is not the same as $R^7$, and said $R^3$ is the same as $R^6$. Preferably, $R^1$ is selected from C1-C6-alkoxy, $O(CH_2)O(CH_3)$ and $O(CH_2)O(CH_2)_2OCH_3$; said $R^2$, $R^3$, $R^6$ and $R^7$ are independently selected from H, $NH_2$, $N(H)(C1-C6-alkyl)$ or $N(C1-C6-alkyl)_2$, and $R^4$ and $R^5$ are each H, and $R^8$ is selected from H, $NH_2$, $N(H)(C1-C2-alkyl)$, $N(C1-C2-alkyl)_2$, C1-C4-alkoxy and F. Further preferably for said very preferred embodiments of non-symmetrical substitution pattern, in particular said compounds of formula (A) of non-symmetrical substitution pattern, said $R^1$ is selected from C1-C4-alkoxy, $O(CH_2)O(CH_3)$ and $O(CH_2)O(CH_2)_2OCH_3$; said $R^2$, $R^3$, $R^6$ and $R^7$ are independently selected from H, $N(H)(C1-C4-alkyl)$ or $N(C1-C4-alkyl)_2$, and $R^4$ and $R^5$ are each H, and $R^8$ is selected from H, $N(C1-C2-alkyl)_2$, C1-C4-alkoxy and F. Again further preferably for said very preferred embodiments of non-symmetrical substitution pattern, in particular said compounds of formula (A) of non-symmetrical substitution pattern, said $R^1$ is selected from C1-C2-alkoxy, $O(CH_2)O(CH_3)$ and $O(CH_2)O(CH_2)_2OCH_3$; said $R^2$, $R^3$, $R^6$ and $R^7$ are independently selected from H and $N(C1-C4-alkyl)_2$, and $R^4$ and $R^5$ are each H, and $R^8$ is selected from H, $N(C1-C2-alkyl)_2$, C1-C2-alkoxy. Again further preferably for said very preferred embodiments of non-symmetrical substitution pattern, in particular said compounds of formula (A) of non-symmetrical substitution pattern, said $R^1$ is selected from OMe, $O(CH_2)O(CH_3)$ and $O(CH_2)O(CH_2)_2OCH_3$; said $R^2$, $R^3$, $R^6$ and $R^7$ are independently selected from H and $N(C1-C2-alkyl)_2$, and $R^4$ and $R^5$ are each H, and $R^8$ is selected from H, $N(C1-C2-alkyl)_2$, C1-C2-alkoxy.

Again further preferably for said very preferred embodiments of non-symmetrical substitution pattern, in particular said compounds of formula (A) of non-symmetrical substitution pattern, said $R^1$ is not the same as $R^8$, and said $R^2$ is not the same as $R^7$, and said $R^3$ is not the same as $R^6$, said $R^1$ is selected from C1-C2-alkoxy, $O(CH_2)O(CH_3)$ and $O(CH_2)O(CH_2)_2OCH_3$; said $R^2$, $R^3$, $R^6$ and $R^7$ are independently selected from H and $N(C1-C4-alkyl)_2$, and $R^4$ and $R^5$ are each H., and $R^8$ is selected from H, C1-C2-alkoxy Again further preferably for said very preferred embodiments of non-symmetrical substitution pattern, in particular said compounds of formula (A) of non-symmetrical substitution pattern, said $R^1$ is not the same as $R^8$, and said $R^2$ is not the same as $R^7$, and said $R^3$ is the same as $R^6$, said $R^1$ is selected from C1-C2-alkoxy, $O(CH_2)O(CH_3)$ and $O(CH_2)O(CH_2)_2OCH_3$; said $R^2$, $R^3$, $R^6$ and $R^7$ are independently selected from H and $N(C1-C4-alkyl)_2$, and $R^4$ and $R^5$ are each H, and $R^8$ is selected from H, C1-C2-alkoxy.

Again further preferably for said very preferred embodiments of non-symmetrical substitution pattern, in particular said compounds of formula (A) of non-symmetrical substitution pattern, said $R^1$ is not the same as $R^8$, and said $R^2$ is not the same as $R^7$, and said $R^3$ is not the same as $R^6$, said $R^1$ is selected from OMe, $O(CH_2)O(CH_3)$ and $O(CH_2)O(CH_2)_2OCH_3$; said $R^2$, $R^3$, $R^6$ and $R^7$ are independently selected from H and $N(C1-C2-alkyl)_2$, and $R^4$ and $R^5$ are each H, and $R^8$ is selected from H and OMe.

Again further preferably for said very preferred embodiments of non-symmetrical substitution pattern, in particular said compounds of formula (A) of non-symmetrical substitution pattern, said $R^1$ is not the same as $R^8$, and said $R^2$ is not the same as $R^7$, and said $R^3$ is the same as $R^6$, said $R^1$ is selected from OMe, $O(CH_2)O(CH_3)$ and $O(CH_2)O(CH_2)_2OCH_3$; said $R^2$, $R^3$, $R^6$ and $R^7$ are independently selected from H and $N(C1-C2-alkyl)_2$, and $R^4$ and $R^5$ are each H, and $R^8$ is selected from H and OMe.

Again further preferably for said very preferred embodiments of non-symmetrical substitution pattern, in particular said compounds of formula (A) of non-symmetrical substitution pattern, said $R^1$ is not the same as $R^8$, and said $R^2$ is not the same as $R^7$, and said $R^3$ is not the same as $R^6$, said $R^1$ is OMe; said $R^2$, $R^3$, $R^6$ and $R^7$ are independently selected from H and $N(Me)_2$, and $R^4$ and $R^5$ are each H, and $R^8$ is selected from H and OMe.

Again further preferably for said very preferred embodiments of non-symmetrical substitution pattern, in particular said compounds of formula (A) of non-symmetrical substitution pattern, said $R^1$ is not the same as $R^8$, and said $R^2$ is not the same as $R^7$, and said $R^3$ is the same as $R^6$, said $R^1$ is OMe; said $R^2$, $R^3$, $R^6$ and $R^7$ are independently selected from H and $N(Me)_2$, and $R^4$ and $R^5$ are each H, and $R^8$ is selected from H and OMe.

For said very preferred embodiments of non-symmetrical substitution pattern, in particular said compounds of formula (A) of non-symmetrical substitution pattern, said $R^9$ is naphthyl. In a further very preferred embodiment, said $R^9$ is phenyl. In a further very preferred embodiment, said $R^9$ is selected from phenyl, naphthyl, 4-methylphenyl. 2,6-dimethylphenyl, and 2,4,6-trimethylphenyl. In a further very preferred embodiment, said $R^9$ is selected from phenyl, 4-methylphenyl, 2,6-dimethylphenyl, and 2,4,6-trimethylphenyl. In a further very preferred embodiment, said $R^9$ is 4-methylphenyl. In a further very preferred embodiment, said $R^9$ is 4-flurophenyl. In a further very preferred embodiment, said $R^9$ is 4-methoxyphenyl. In a very further preferred embodiment, said $R^9$ is 2,6-dimethylphenyl. In a further preferred embodiment, said $R^9$ is 2,6-dimethoyphenyl. In a further very preferred embodiment, said $R^9$ is 2,4,6-trimethylphenyl. In a further preferred embodiment, said $R^9$ is 2,4,6-trimethoxyphenyl.

EXAMPLES

Various aspects of the invention make use of the following materials and methods and are illustrated by the following non-limiting examples.

Materials and Methods

All reactions were carried out in dried glassware under an Ar atmosphere. nBuLi solution in hexane was purchased from Acros Organics (Nr. 181271) and the concentration was determined by titration with 1,10-phenanthroline in THF against s BuOH according to Eastham and Watson (S. C. Watson, J. F. Eastham *J. Organometal. Chem.* 1967, 9, 165). All photoreactions were performed in a sealed Biotage® 2-5 mL microwave vial equipped with a 10 mm×5 mm magnetic stir bar stirring at 1400 rpm. The vial was placed on a stirring plate laterally in 3 cm distance to a Kessil LED A16OWE Tuna Blue, 40 W, adjusted to maximum intensity and white ($\lambda_{max}$: 464 nm). A sideward fan was used to keep ambient temperature (~30° C.). All starting materials and reaction solvents were purchased from commercial sources and used without further purification. Solvents for extractions and chromatography were technical grade. Analytical thin layer chromatography (TLC) was performed on pre-coated Merck silica gel 60 $F_{254}$ plates (0.25 mm) and visualized by UV and VIS. Flash column chromatography was carried out on Silicycle SiliaFlash P60 (230-400 mesh). Concentration in vacuo was performed by rotary evaporation to ~10 mbar at 40° C. and drying at high vacuum at $10^{-1}$ mbar and RT.

$^1$H NMR and $^{13}$C NMR spectra were recorded on a Bruker Avance III 500 MHz and Avance III HD 600 MHz spectrometer and $^{19}$F NMR spectra on a Bruker Avance III 250 MHz spectrometer at 298 K in $CDCl_3$ supplied by Cambridge Isotope Laboratories (DLM-7TB-100S). Chemical shifts (δ) are reported in ppm relative to tetramethylsilane (0.00 ppm). The multiplicities are reported in Hz as: s=singlet, br=broad singlet, d=doublet, t=triplet, q=quartet and m=multiplet. Melting points were measured on a Büchi M-565 melting point apparatus and are uncorrected.

IR spectra were measured on a ATR Varian Scimitar 800 FT-IR spectrometer and reported in cm $^{-1}$. The intensities of the bands are reported as: w=weak, m=medium, s=strong. High-resolution mass spectrometry (HR-ESI) was performed by Dr. Heinz Nadig of the University of Basel on a Bruker maXis 4G QTOF ESI mass spectrometer.

UV/Vis spectroscopy was performed on a Shimadzu UV-1650 PC spectrometer and steady-state luminescence spectroscopy was performed on a FluoroMax 4 instrument from Horiba Jobin-Yvon of all dyes in MeCN using Hellma fluorescence cells (111-QS, light path: 10×10 mm). Molar attenuation coefficients (ε) were determined at the wavelength of maximum absorbance ($X_{abs}$) and emission of a ~15 µmol $L^{-1}$ dye solution.

Fluorescent lifetimes ($<\tau_F>$) of a ~15 µmol $L^{-1}$ solution were measured using a Hamamatsu Compact Fluorescence lifetime Spectrometer C11367 Quantaurus-Tau using an LED light source with excitation wavelength of 470 nm with a peak count of up to 10000 and repetition rate of 5 MHz. The fluorescence decay was satisfactorily fit either to a first or second order rate equation.

Cyclic Voltammetry was performed in dry, degassed 0.1 molL$^{-1}$ n-butylammonium hexafluorophosphate in MeCN to give ground state reduction potential $E_{1/2}$(P/P). Voltammograms were recorded with a Versastat 3-200 potentiostat from Princeton Applied Research employing a glassy carbon disk working electrode, SCE reference electrode and a silver wire counter electrode and a potential sweep rate of 0.1 Vs$^{-1}$. The glassy carbon electrode and Ag wire were polished prior to measurement. The excitation energy ($E_{0.0}$) was determined by the point of intersection of the normalized absorbance and emission signal. The subtraction of the ground state reduction potential $E_{1/2}$(P/P) by the excitation energy ($E_{0.0}$) allows the calculation of the excited state reduction potential $E_{1/2}$(P*/P).

Example 1

3-(3-methoxyphenoxy)-N,N-dimethylaniline

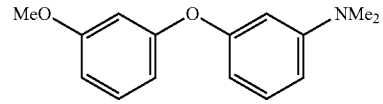 [SMILES: COc1cccc(Oc2cccc(N(C)C)c2)c1]

To a mixture of 3-(dimethylamino)phenol (1.27 g, 9.25 mmol), CuI (147 mg, 0.771 mmol), 2-picolinic acid (380 mg, 3.08 mmol) an $K_3PO_4$ (3.27 g, 15.3 mmol) in $(CH_3)_2SO$ (15 mL) at RT was added 3-bromoanisole (975 µL, 7.71 mmol) and stirred vigorously at 85° C. for 24 h. The reaction mixture was cooled to RT and $H_2O$ (100 mL) was added. The mixture was extracted with $Et_2O$ (3×100 mL), the combined organic phases were washed with $H_2O$ (2×100 mL), dried over $Na_2SO_4$ and the solvent was removed in vacuo.

Purification by chromatography (pentane 100% to pentane:$Et_2O$ 10:1: to 10:2) gave a light yellow oil (1.14 g, 61%, b.p. 174° C. at 0.8 mbar): $R_f$ 0.67 ($Et_2O$:pentane 1:1); $n_{max}$ (neat): 2940 w, 2885 w, 2836 w, 2805 w, 1597 s, 1570 s, 1485 s, 1445 s, 1355 m, 1263 m, 1213 s, 1145 s, 1040 m, 1000 s, 948 m, 832 m, 762 s, 685 s; $^1$H NMR (500 MHz, $CDCl_3$) d=7.21-7.24 (1H, m), 7.18-7.21 (1H, m), 6.64-6.66 (1H, m), 6.63 (1H, d, $^4$J3.4), 6.62 (1H, d, $^4$J 1.8) 6.51 (1H, dd, $^3$J 8.3, $^4$J2.5) 6.45-6.46 (1H, m) 6.38 (1H, dd, $^3$J 8.0, $^4$J2.2) 3.80 (3H, s, $OCH_3$), 2.96 (6H, s, $N(CH_3)_2$); $^{13}$C NMR (125 MHz, $CDCl_3$) d=160.9, 158.9, 157.8, 152.1, 130.0, 129.9, 110.7, 108.5, 107.9, 107.1, 104.5, 103.7, 55.3 ($OCH_3$), 40.5 ($N(CH_3)_2$); ESI-MS: m/z calcd. for $C_{15}H_{18}NO_2^+$ 244.1332 found 244.1334 [M+H$^+$].

Example 2

4-bromo-3-(3-methoxyphenoxy)-N,N-dimethylaniline

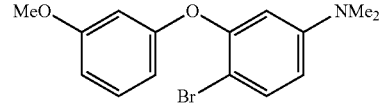 [SMILES: COc1cccc(Oc2cc(N(C)C)ccc2Br)c1]

To a solution of 3-(3-methoxyphenoxy)-N,N-dimethylaniline (243 mg, 1.00 mmol) in $CH_2Cl_2$ (10 mL) at 0° C. was added a solution of $Br_2$ (56.4 µL, 1.10 mmol) in $CH_2Cl_2$ (10 mL) over 1 h by the use of a syringe pump. $Na_2SO_3$ aq. sat. (5 mL) was added and the mixture was extracted with $CH_2Cl_2$ (3×10 mL). The combined organic phases were washed with $H_2O$ (10 mL), dried over $Na_2SO_4$ and the solvent was removed in vacuo. Recrystallization from n-hexane (3.0 mL) gave a beige solid (220 mg, 68%, m.p. 54.1-57.3° C.): $R_f$ 0.61 ($Et_2O$:pentane 1:1); $n_{max}$ (neat): 2944 w, 2903 w, 2842 w, 1590 s, 1485 s, 1445 s, 1357 m, 1285 m, 1260 s, 1226 s, 1191 m, 1133 s, 1046 s, 1034 s, 996 w, 933 m, 888 m, 848 m, 798 m, 761 s684 m, 658 m; $^1$H NMR (500 MHz, $CDCl_3$) δ=7.42 (d, $^3$J 8.9, 1H), 7.20-7.23 (m, 1H), 6.64 (ddd, $^3$J 8.3, $^4$J 2.4, 0.8, 1H), 6.55-6.56 (m, 1H), 6.53 (ddd, $^3$J 8.1, $^4$J 2.3, 0.9, 1H), 6.45 (dd, $^3$J 8.9, $^4$J 3.0, 1H), 6.40 (d, $^4$J 2.9, 1H), 3.80 (s, 3H, $OCH_3$), 2.91 (s, 6H, $N(CH_3)_2$). $^{13}$C NMR (125 MHz, $CDCl_3$) δ=160.9, 158.7, 153.2, 151.1, 133.5, 130.0, 110.1, 109.4, 108.2, 105.8, 103.4, 101.2, 55.4 (OCH$_3$), 40.5 (N(CH$_3$)$_2$); ESI-MS: m/z calcd. for C$_{15}$H$_{17}$BrNO$_2^+$ 322.0437 found 322.0440 [M+H$^+$].

As an alternative to the described recrystallization purification by chromatography (pentane:CH$_2$Cl$_2$ 8:1 to 6:1 to 4:1 to 2:1) can be conducted.

Example 3

General Procedure I

Metalation Via Double DoM or Combined DoM/Halogen-Metal Exchange

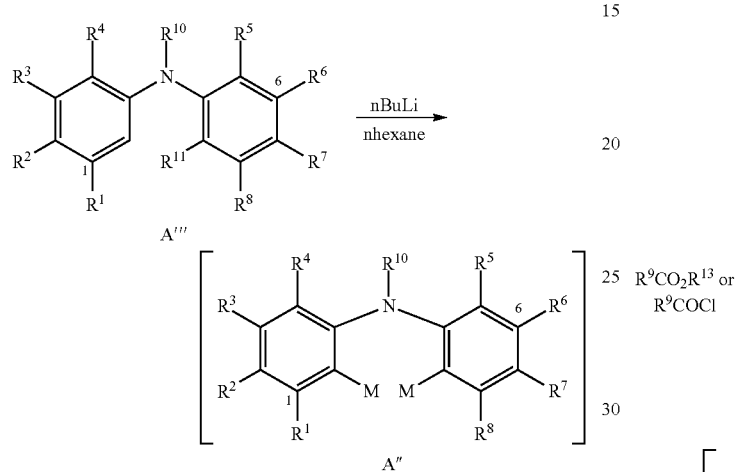

To a solution of arylaniline (160 μmol) in n-hexane (2.0 mL) or n-hexane:Et$_2$O (10:1, 2.2 mL) was added a solution of n-butyllithium in hexanes (176 μL, 1.49 molL$^{-1}$, 320 μmol) at RT. The mixture was stirred 6 h at 65° C. The reaction mixture was directly used in the next step.

Example 4

General Procedure II

Metalation Via Double DoM or combined DoM/Halogen-Metal Exchange

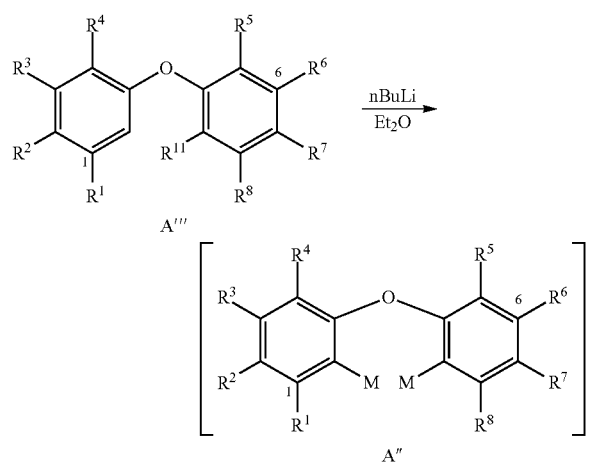

To a solution of aryl ether (140 μmol) in Et$_2$O (1.0 mL) was added a solution of n-butyllithium in hexanes (197 μL, 1.42 molL$^{-1}$, 280 μmol) at RT. The mixture was stirred 1 h at 40° C. The reaction mixture was directly used in the next step.

Example 5

General Procedure III

Ester to Acridinium Transformation

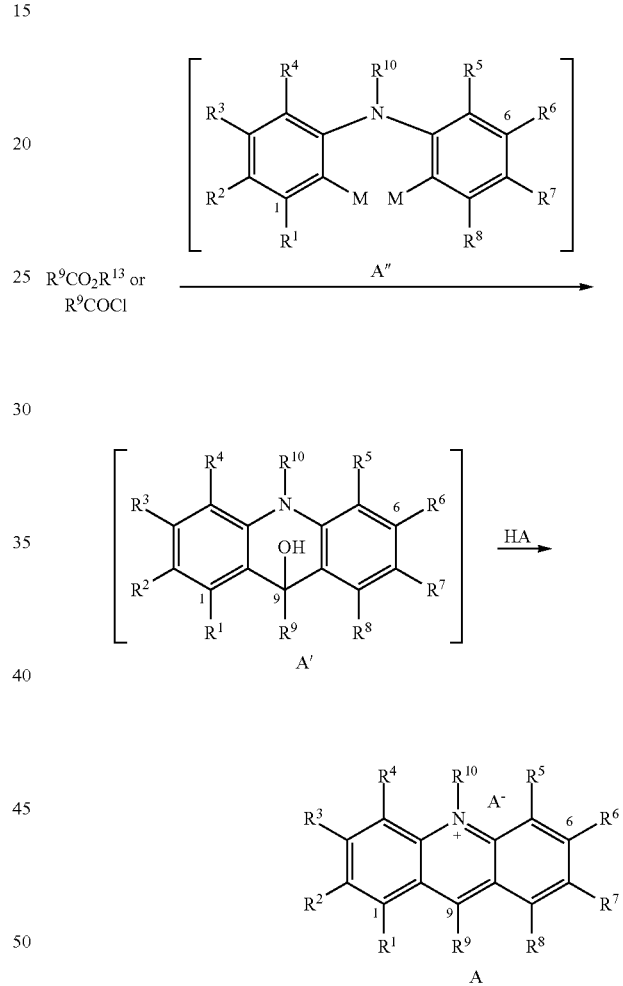

To the reaction mixture of the metalated aryl aniline in n-hexane (160 μmol, Example 3) at 20° C. was added a solution of carboxylic acid ester (100 μmol) in anhydrous THF (0.60 mL) and the reaction mixture was allowed to warm to RT over 12 h or 18 h. Aqueous HBr (1.00 mL, 48%) was added, followed by water (20 mL) and the mixture was extracted by CHCl$_3$:i PrOH solution (4×10 mL; 85:15). The combined organic layer was dried over Na$_2$SO$_4$, filtered and concentrated in vacuo. Column chromatography with 100% CH$_2$Cl$_2$ to CH$_2$Cl$_2$:MeOH 100:2 to 100:5 to 100:8 to 100:9 gave pure product.

Example 6

General Procedure IV

Ester to Xanthylium Transformation

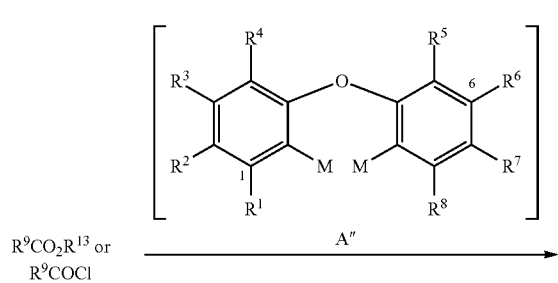

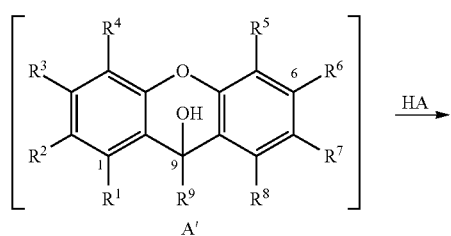

To the reaction mixture of the metalated aryl ether in Et$_2$O (140 gmol, Example 4) at 40° C. was added a solution of carboxylic acid ester (100 μmol) in anhydrous Et$_2$O (1.0 mL) and the reaction mixture continued to stir for 2 h at that temperature. Aqueous HCl (1.00 mL, 10.0 molL$^{-1}$) was added. The solvent was evaporated and the remaining residue was poured over a bed (d×h=2.0×2.5 cm) of Amberlyst A-21 (20-50 mesh, Aldrich, Nr. 216410; washed extensively with MeOH prior to use). The solvent was removed in vacuo and the residue was purified by chromatography (10 g silica gel, d=2 cm, h=7 cm) with 100% CH$_2$Cl$_2$ to CH$_2$Cl$_2$:MeOH 100:2 to 100:5 to 100:10. The solvent of the fractions containing product were combined and evaporated. The residue was dissolved in CH$_2$Cl$_2$ and filtered over a cotton ball.

Example 7

General Procedure V

Ester to 9,10-Dihydroacridin-9-ol Transformation

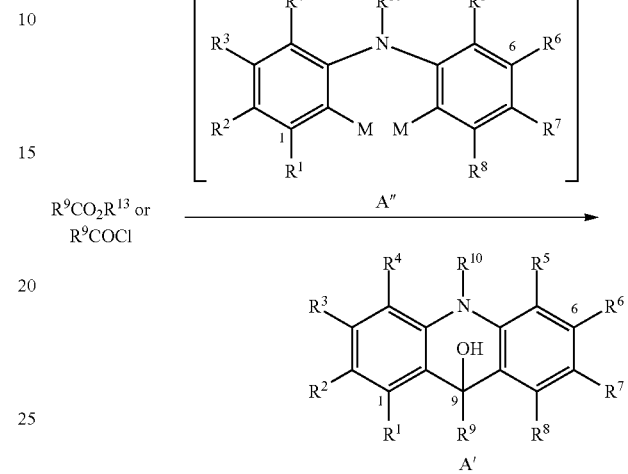

To the reaction mixture of the metalated aniline in n-hexane (160 gmol, Example 3) at 20° C. was added a solution of carboxylic acid ester (100 μmol) in anhydrous THF (0.60 mL) and the reaction mixture was allowed to warm to RT over 12 h. Aqueous saturated NH$_4$Cl (1.00 mL) was added, followed by water (20 mL) and the mixture was extracted by CH$_2$Cl$_2$ (4×10 mL). The combined organic layer was dried over Na$_2$SO$_4$, filtered and concentrated in vacuo. Recrystallization gave pure product.

Example 8

General Procedure VI

Ester to Xanthen-9-ol Transformation

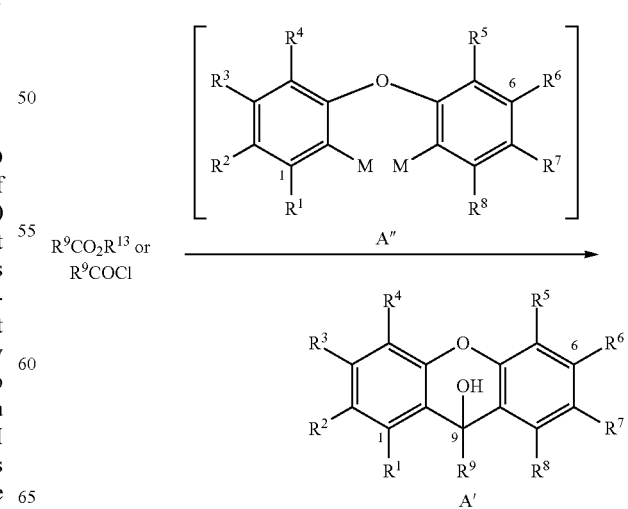

To the reaction mixture of the metalated aryl ether in Et$_2$O (800 gmol, Example 4) at 40° C. was added a solution of carboxylic acid ester (800 μmol) in anhydrous THF (5.0 mL) and the reaction mixture was allowed to warm to RT over 12 h. Aqueous saturated NH$_4$Cl (1.00 mL) was added, followed by water and the mixture was extracted by Et$_2$O. The combined organic layer was dried over Na$_2$SO$_4$, filtered and concentrated in vacuo. Recrystallization gave pure product.

Example 9

1,8-Dimethoxy-10-methyl-9-phenylacridinium bromide

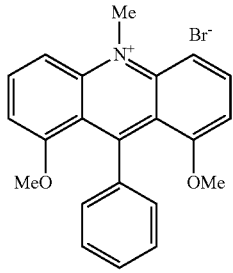 [SMILES: COc1cccc2c1c(-c1ccccc1)c1c(OC)cccc1[n+]2C ; [Br-]]

The compound was prepared according to the general procedure I, described in Example 3, using 3-methoxy-N-(3-methoxyphenyl)-N-methylaniline (38.9 mg, 160 μmol) in n-hexane (2.0 mL) and general procedure III, described in Example 5, using methyl benzoate (13.6 mg, 100 μmol) and was stirred 12 h at RT. Purification gave a brown red solid (19.9 mg, 49%, decomp. at 150° C.): R$_f$ 0.12 (CH$_2$Cl$_2$:MeOH 10:1); ν$_{max}$ (neat): 3411 w, 1606 m, 1504 m, 1465 m, 1345 m, 1260 s, 1168 m, 1072 m, 926 w, 816 m, 729 s, 699 s, 632 m; $^1$H NMR (500 MHz, CDCl$_3$): δ=8.24-8.28 (2H, m, C4H, C5H), 8.26-8.30 (2H, m, C3H, C6H), 7.42-7.46 (3H, m, C3'H, C4'H, C5'H), 7.15-7.17 (2H, m, C2'H, C6'H), 7.01 (2H, dd, $^3$J 7.2, $^4$J 1.2, C2H, C7H), 5.02 (3H, s, NCH$_3$), 3.48 (6H, s, 2×OCH$_3$); $^{13}$C NMR (125 MHz, CDCl$_3$): δ=161.1 (C9), 160.1 (C1, C8), 142.3 (C4a, C10a), 141.4 (C1'), 140.8 (C3, C6), 127.1 (C4'), 126.8 (C3', C5'), 125.6 (C2', C6'), 119.1 (C8a, C9a), 110.2 (C4, C5), 106.8 (C2, C7), 56.6 (2×OCH$_3$), 42.3 (NCH$_3$); ESI-MS: m/z calcd. for C$_{22}$H$_{20}$NO$_2^+$ 330.1489 found 330.1494 [M$^+$]. Luminescence spectroscopy (in MeCN): λ$_{abs1}$: 497 nm; X$_{abs2}$: 403 nm; λ$_{abs3}$: 288 nm; ε$_{abs1}$: 4.4·10$^3$ L cm mol$^{-1}$; ε$_{abs2}$: 6.6·10$^3$ L cm mol$^{-1}$; ε$_{abs3}$: 7.6·10$^4$ L cm mol$^{-1}$; λ$_{em}$(exc 487): 576 nm; λ$_{em}$(exc 393): 586 nm; Stokes shift: 79 nm; E$_{0.0}$: 2.33 eV; <τ$_F$>: 2.7 ns; Cyclic voltammetry (vs SCE): E$_{1/2}$(P*/P): +1.81 V, E$_{1/2}$(P/P): −0.52 V.

Example 10

9-(4-Fluorophenyl)-1,8-dimethoxy-10-methylacridinium bromide

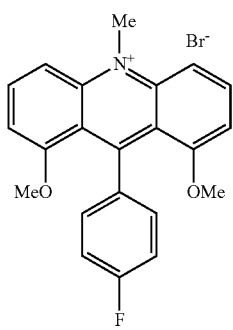 [SMILES: COc1cccc2c1c(-c1ccc(F)cc1)c1c(OC)cccc1[n+]2C ; [Br-]]

The compound was prepared according to the general procedure I, described in Example 3, using 3-methoxy-N-(3-methoxyphenyl)-N-methylaniline (38.9 mg, 160 μmol) in n-hexane (2.0 mL) and general procedure III, described in Example 5, using methyl 4-fluorobenzoate (15.4 mg, 100 μmol) and was stirred 18 h at RT. Purification gave a brown red solid (17.5 mg, 41%, decomp. at 130° C.): R$_f$ 0.13 (CH$_2$Cl$_2$:MeOH 10:1); ν$_{max}$ (neat): 3379 w, 1606 m, 1579 m, 1508 s, 1462 s, 1348 m, 1259 s, 1219 m, 1167 m, 1072 m, 1025 w, 919 m, 833 m, 816 m, 770 m, 723 m, 635 s; $^1$H NMR (500 MHz, CDCl$_3$): δ=8.27-8.29 (4H, m, C3H, C4H, C5H, C6H), 7.16-7.17 (4H, m, C2'H, C3'H, C5'H, C6'H), 7.04 (2H, dd, $^3$J5.9, $^4$J2.9, C2H, C7H), 5.03 (3H, s, NCH$_3$), 3.54 (6H, s, 2×OCH$_3$); $^{13}$C NMR (125 MHz, CDCl$_3$): δ=162.0 ($^1$J$_{CF}$ 247 Hz, CF), 159.9 (C9), 159.8 (C1, C8), 142.3 (C4a, C10a), 140.8 (C3, C6), 137.3 ($^4$J$_{CF}$ 3.6 Hz, C1'), 127.6 ($^3$J$_{CF}$ 8.0 Hz, C2', C6), 119.2 (C8a, C9a), 114.0 ($^2$J$_{CF}$ 21.8 Hz, C3', C5'), 110.5 (C4, C5), 106.9 (C2, C7), 56.7 (2×OCH$_3$), 42.5 (NCH$_3$); $^{19}$F NMR (235 MHz, CDCl$_3$): 114.7; ESI-MS: m/z calcd. for C$_{22}$H$_{19}$FNO$_2^+$ 348.1394 found 348.1397 [M$^+$]. Luminescence spectroscopy (in MeCN): λ$_{abs1}$: 497 nm; λ$_{abs2}$: 395 nm; λ$_{abs3}$: 288 nm; ε$_{abs1}$: 3.9·10$^3$ L cm mol$^{-1}$; ε$_{abs2}$: 6.3·10$^3$ L cm mol$^{-1}$; ε$_{abs3}$: 6.9·10$^4$ L cm mol$^{-1}$; λ$_{em}$(exc 487): 579 nm; Stokes shift: 82 nm; E$_{0.0}$: 2.31 eV; <τ$_F$>: 3.0 ns; Cyclic voltammetry (vs SCE): E$_{1/2}$(P*/P): +1.80 V, E$_{1/2}$(P/P$^{31}$): 0.51 V.

Example 11

1,8-Dimethoxy-9-(4-methoxyphenyl)-10-methylacridinium bromide

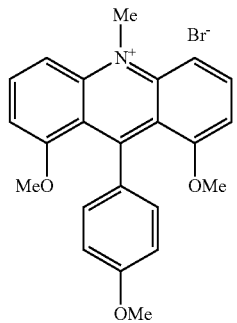 [SMILES: COc1ccc(-c2c3c(OC)cccc3[n+](C)c3cccc(OC)c23)cc1 ; [Br-]]

The compound was prepared according to the general procedure I, described in Example 3, using 3-methoxy-N-(3-methoxyphenyl)-N-methylaniline (38.9 mg, 160 μmol) in n-hexane (2.0 mL) and general procedure III, described in Example 5, using methyl 4-methoxybenzoate (16.6 mg, 100 μmol) and was stirred 12 h at RT. Purification gave a brown red solid (17.2 mg, 39%, decomp. at 130° C.): R$_f$ 0.15 (CH$_2$Cl$_2$:MeOH 10:1); ν$_{max}$ (neat): 3375 w, 2993 w, 1606 m, 1577 m, 1509 m, 1461 m, 1346 m, 1240 s, 1165 s, 1032 m, 814 m, 765 s, 734 w, 647 m, 635 w; $^1$H NMR (500 MHz, CDCl$_3$): δ=8.22-8.28 (4H, m, C3H, C4H, C5H, C6H), 7.06-7.09 (2H, m, C2'H, C6'H), 7.02 (2H, dd, $^3$J 7.6, $^4$J0.9, C2H, C7H), 6.98-7.00 (2H, m, C3'H, C5'H), 5.00 (3H, s, NCH$_3$), 3.93 (3H, s, OCH$_3$), 3.55 (6H, s, 2×OCH$_3$); $^{13}$C NMR (125 MHz, CDCl$_3$): δ=161.6 (C9), 160.2 (C1, C8), 158.9 (C4'), 142.3 (C4a, C10a), 140.6 (C3, C6), 133.7 (C1'), 127.2 (C2', C6), 119.5 (C8a, C9a), 112.4 (C3', C5'), 110.1 (C4, C5), 106.8 (C2, C7), 56.8 (2×OCH$_3$), 55.5 (OCH$_3$), 42.3 (NCH$_3$); ESI-MS: m/z calcd. for C$_{23}$H$_{22}$NO$_3^+$ 360.1594 found 360.1595 [M$^{-1}$]. Luminescence spectroscopy (in MeCN): $\lambda_{abs1}$: 495 nm; $\lambda_{abs2}$: 399 nm; $\lambda_{abs3}$: 287 nm; $\varepsilon_{abs1}$: 4.6·10$^3$ L cm mol$^{-1}$; $\varepsilon_{abs2}$: 7.0.10$^3$ L cm mol$^{-1}$; $\varepsilon_{abs3}$: 6.9·10$^4$ L cm mol$^{-1}$; $\lambda_{em}$(exc 485): 567 nm; Stokes shift: 72 nm; E$_{0,0}$: 2.30 eV; <$\tau_F$>: 5.9 ns; Cyclic voltammetry (vs SCE): E$_{1/2}$(P*/P$^-$): +1.87 V, E$_{1/2}$(P/P$^{-1}$): 0.43 V.

Example 12

1,8-Dimethoxy-10-methyl-9-(naphthalen-1-yl)acridinium bromide

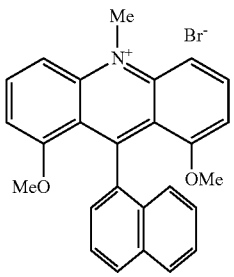 [SMILES: COc1cccc2c1c(-c1cccc3ccccc13)c1c(OC)cccc1[n+]2C ; [Br-]]

The compound was prepared according to the general procedure I, described in

Example 3, using 3-methoxy-N-(3-methoxyphenyl)-N-methylaniline (38.9 mg, 160 µmol) in n-hexane (2.0 mL) and general procedure III, described in Example 5, using methyl 1-naphthoate (18.6 mg, 100 µmol) and was stirred 12 h at RT. Purification gave a brown red solid (26.0 mg, 57%, decomp. at 120° C.): R$_f$ 0.01 (CH$_2$Cl$_2$:MeOH 10:1); $v_{max}$ (neat): 3462 w, 3396 w, 1608 m, 1577 m, 1503 m, 1458 s, 1348 m, 1258 s, 1161 m, 1065 s, 1015 w, 950 w, 800 m, 762 s, 647 w; $^1$H NMR (500 MHz, CDCl$_3$): δ=8.34-8.36 (2H, m, C3H, C6H), 8.27-8.30 (2H, m, C4H, C5H), 7.97-7.98 (1H, m, C5'H), 7.91-7.93 (1H, m, C4'H), 7.31 (1H, ddd, $^3$J 8.9, 6.8, $^4$J 1.3, C7'H), 7.48-7.52 (2H, m, C3'H, C6'H), 7.18 (1H, dd, $^3$J 8.4, $^4$J 0.7, C8'H), 6.96 (1H, dd, $^3$J 7.0, $^4$J 1.0, C2'H), 6.93 (2H, d, $^3$J 7.8, C2H, C7H), 5.11 (3H, s, NCH$_3$), 3.09 (6H, s, 2×OCH$_3$); $^{13}$C NMR (125 MHz, CDCl$_3$): δ=160.4 (C9), 159.8 (C1, C8), 142.3 (C4a, C10a), 140.8 (C4, C5), 139.8 (C4a'), 132.1 (C1'), 131.9 (C8a'), 128.2 (C5'), 127.4 (C4'),126.3 (C7'), 125.8 (C3'), 125.0 (C8'), 124.9 (C6'), 121.8 (C2'), 120.0 (C8a, C9a), 110.5 (C3, C6), 107.0 (C2, C7), 56.5 (2×OCH$_3$), 42.4 (NCH$_3$); ESI-MS: m/z calcd. for C$_{26}$H$_{22}$NO$_2^+$ 380.1645 found 380.1648 [M$^+$]. Luminescence spectroscopy (in MeCN): $\lambda_{abs1}$: 497 nm; $\lambda_{abs2}$: 394 nm; $\lambda_{abs3}$: 287 nm; $\varepsilon_{abs1}$: 5.0·10$^3$ L cm mol$^{-1}$; $\varepsilon_{abs2}$: 7.6·10$^3$ L cm mol$^{-1}$, $\varepsilon_{abs2}$: 7.6·10$^4$ L cm mol$^{-1}$; $\lambda_{em}$(exc 487): 531 nm; Stokes shift: 34 nm; E$_{0,0}$: 2.39 eV; <$\tau_F$>: 4.1 ns; Cyclic voltammetry (vs SCE): E$_{1/2}$(P*/P): +1.88 V, E$_{1/2}$(P/P$^-$): 0.51 V.

Example 13

1,8-Dimethoxy-10-methyl-9-phenyl-9,10-dihydroacridin-9-ol

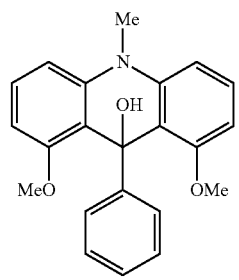

The compound was prepared according to the general procedure I, described in Example 3, using 3-methoxy-N-(3-methoxyphenyl)-N-methylaniline (38.9 mg, 160 µmol) in n-hexane (2.0 mL) and general procedure V, described in Example 7, using methyl benzoate (13.6 mg, 100 µmol) and was stirred 12 h at RT. Recrystallization from hexane: toluene (7.0 mL, 5:3) gave a dark grey solid (19.9 mg, 49%, m.p. 171.5-173.9° C.): $v_{max}$ (neat): 3514 w, 1596 s, 1470 s, 1374 w, 1251 m, 1171 w, 1081 s, 1020 w, 908 w, 773 s, 725 s, 631m; $^1$H NMR (500 MHz, CDCl$_3$): δ=7.33-7.35 (2H, m, C2'H, C6'H), 7.21 (2H, t, $^3$J 8.3, C3H, C6H), 7.13-7.16 (2H, m, C3'H, C5'H), 7.01-7.04 (1H, C4'H), 6.70 (2H, dd, $^3$J 8.4, $^4$J 0.5, C4H, C5H), 6.44 (2H, dd, $^3$J 8.2, $^4$J 0.6, C2H, C7H), 5.17 (1H, s, OH), 3.53 (3H, s, NCH$_3$), 3.51 (6H, s, 2×OCH$_3$); $^{13}$C NMR (125 MHz, CDCl$_3$): δ=158.3 (C1, C8), 150.8 (C1'), 139.4 (C4a, C10a), 128.8 (C3, C6), 126.1 (C3', C5'), 125.9 (C2', C6'), 125.0 (C4), 117.0 (C8a, C9a), 106.4 (C4, C5), 105.0 (C2, C7), 72.6 (C9), 55.9 (2×OCH$_3$), 35.2 (NCH$_3$). ESI-MS: m/z calcd. for C$_{22}$H$_{21}$NNaO$_3^+$ 370.1414 found 370.14118 [MNa$^+$].

Example 14

1,8-Dimethoxy-9-phenyl-9H-xanthen-9-ol

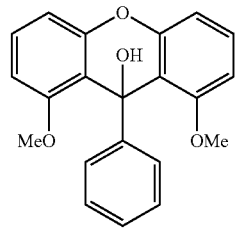

The compound was prepared according to the general procedure II and VI described in Example 4 and 8 using 3,3'-oxybis(methoxybenzene) (184 mg, 800 µmol) and methyl benzoate (109 mg, 800 µmol) and was stirred 12 h at RT. Recrystallization from hexane:toluene (5:3) gave a white solid (113 mg, 42%, m.p. 223.4-225.5° C.): v. (neat): 3527 w, 3005 w, 2943 w, 2841 w, 2361 w, 1618 w, 1605 w, 1580 w, 1478 m, 1452 m, 1433 m, 1358 w, 1316 w, 1273 m, 1247 s, 1178 w, 1095 s, 1074 s, 1013 m, 957 w, 902 w, 887 w, 777 m, 752 m, 730 m, 702 m; $^1$H NMR (500 MHz, CDCl$_3$): δ=7.32-7.35 (2H, m, C2'H, C6'H), 7.23 (2H, t, $^3$J 8.3, C3H, C6H), 7.16-7.19 (2H, m, C3'H, C5'H), 7.05-7.08 (1H, m, C4'H) 6.84 (2H, dd, $^3J$ 8.4, $^4J$ 1.0, C4H, C5H), 6.53 (2H, dd, $^3J$ 8.1, $^4J$ 0.6, C2H, C7H), 4.79 (1H, s, OH), 3.55 (6H, s, 2×OCH$_3$); $^{13}$C NMR (125 MHz, CDCl$_3$): δ=158.1 (C1, C8), 149.3 (C4a, C10a), 149.2 (C1'), 129.1 (C3, C6), 126.4 (C3', C5'), 126.2 (C2', C6'), 125.4 (C4'), 115.6 (C8a, C9a), 109.5 (C4, C5), 106.7 (C2, C7), 70.7 (C9), 56.0 (2×OCH$_3$); ESI-MS: m/z calcd. for $C_{21}H_{18}NaO_4^+$ 357.1097 found 357.1100 [MNa$^+$].

Example 15

9-(4-Fluorophenyl)-1,8-dimethoxy-9H-xanthen-9-ol

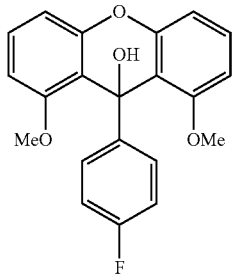

The compound is prepared according to the general procedure II and VI described in Example 4 and 8 using 3,3'-oxybis(methoxybenzene) (32.2 mg, 140 μmol) and methyl 4-fluorobenzoate (15.4 mg, 100 μmol) in Et$_2$O (1.0 mL). Recrystallization from hexane:toluene (5:3) gives a white solid.

Example 16

1,8-Dimethoxy-9,10-diphenylacridinium bromide

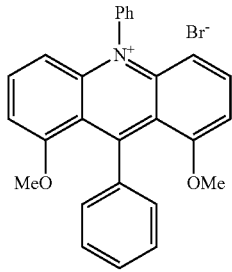 [SMILES: COc1cccc2c1c(-c1ccccc1)c1c(OC)cccc1[n+]2-c1ccccc1 ; [Br-]]

The compound was prepared according to the general procedure I, described in Example 3, using 3-methoxy-N-(3-methoxyphenyl)-N-phenylaniline (48.9 mg, 160 μmol) in n-hexane (2.0 mL) and general procedure III, described in Example 5, using methyl benzoate (13.6 mg, 100 μmol) and was stirred 12 h at RT. Purification gave a brown red solid (17.4 mg, 37%, decomp. at 115° C.): R$_f$ 0.19 (CH$_2$Cl$_2$: MeOH 10:1); v$_{max}$ (neat): 2999 w, 1586 s, 1462 s, 1363 m, 1265 s, 1248 s, 1198 s, 1082 s, 982 w, 925 w, 811 m, 758 s, 738 s, 696, 655m; $^1$H NMR (500 MHz, CDCl$_3$): δ=8.05 (2H, dd, $^3J$ 8.9, 8.2, C3H, C6H), 7.08 (2H, d, $^3J$ 8.0, C2H, C7H), 7.89-7.92 (2H, m, C3"H, C5"H), 7.84-7.87 (1H, m, C4"H), 7.58-7.59 (2H, m, C2"H, C6"H), 7.43-7.50 (3H, m, C3'H, C4'H, C5'H), 7.29-7.31 (2H, m, C2'H, C6'H), 6.90 (2H, dd, $^3J$ 9.1, $^4J$ 0.6, C4H, C5H), 3.52 (6H, s, 2×OCH$_3$) ; $^{13}$C NMR (125 MHz, CDCl$_3$): δ=163.3 (C9), 160.2 (C1, C8), 142.6 (C4a, C10a), 141.2 (C1'), 140.6 (C3, C6), 138.2 (C1"), 131.9 (C3", C5"), 131.7 (C4"), 127.7 (C2", C6"), 127.3 (C4'), 127.0 (C3', C5'), 125.5 (C2', C6'), 118.9 (C8a, C9a), 110.7 (C4, C5), 107.2 (C2, C7), 56.9 (2×OCH$_3$); ESI-MS: m/z calcd. for $C_{27}H_{22}NO_2^+$ 392.1645 found 392.1648 [M$^+$]. Luminescence spectroscopy (in MeCN): $\lambda_{abs1}$: 503 nm; $\lambda_{abs2}$: 409 nm; $\lambda_{abs3}$: 289 nm; $\varepsilon_{abs1}$: 4.4·10$^3$ L cm mol$^{-1}$; $\varepsilon_{abs2}$: 5.8·10$^3$ L cm mol$^{-1}$; $\varepsilon_{abs3}$: 6.7·10$^4$ L cm mol$^{-1}$; $\lambda_{em}$(exc 493): 595 nm; Stokes shift: 92 nm; $E_{0,0}$: 2.23 eV; <τ$_F$>: 3.1 ns; Cyclic voltammetry (vs SCE): $E_{1/2}$(P*/P$^-$): +1.76 V, $E_{1/2}$(P/P$^-$): −0.47 V.

Example 17

1,8-Dimethoxy-9,10-diphenylacridinium tetrafluoroborate

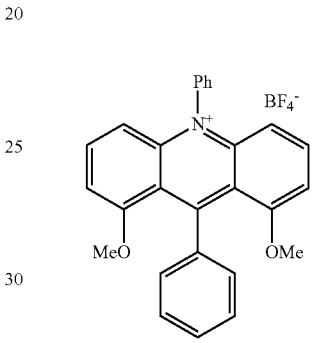

The compound was prepared according to the general procedure I, described in Example 3, using 3-methoxy-N-(3-methoxyphenyl)-N-phenylaniline (48.9 mg, 160 μmol) in n-hexane (2.0 mL) and general procedure III, described in Example 5, using methyl benzoate (13.6 mg, 100 μmol) and was stirred 12 h at RT and treated with aq. HBF$_4$ (50%, 1.00 mL) instead of aq. HBr. Purification gave a brown red solid (21.3 mg, 44%, decomp. at 140° C.): R$_f$ 0.28 (CH$_2$Cl$_2$: MeOH 10:1); v. (neat): 3060 w, 2938 m, 1581 m, 1501 m, 1464 m, 1434 m, 1362 m, 1266 s, 1198 w, 1048 s, 910 w, 819 w, 748 s, 698m; $^1$H NMR (600 MHz, CDCl$_3$): δ=7.94 (2H, dd, $^3J$ 8.9, 8.1, C3H, C6H), 7.82-7.88 (3H, m, C3"H, C4"H, C5"H), 7.55-7.56 (2H, m, C2"H, C6"H), 7.31-7.33 (2H, m, C2'H, C6'H), 7.42-7.48 (3H, m, C3'H, C4'H, C5'H), 6.98 (2H, d, $^3J$8.0, C2H, C7H), 6.89 (2H, d, $^3J$9.0, C4H, C5H), 3.49 (6H, s, 2×OCH$_3$); $^{13}$C NMR (151 MHz, CDCl$_3$): δ=163.4 (C9), 160.2 (C1, C8), 142.7 (C4a, C10a), 141.4 (C1'), 140.9 (C3, C6), 138.4 (C1"), 131.7 (C3", C5"), 131.5 (C4"), 127.8 (C2", C6"), 127.1 (C4'), 126.9 (C3', C5'), 125.6 (C2', C6'), 119.1 (C8a, C9a), 110.8 (C4, C5), 106.9 (C2, C7), 56.7 (2×OCH$_3$); $^{19}$F NMR (235 MHz, CDCl$_3$): 154.5; ESI-MS: m/z calcd. for $C_{27}H_{22}NO_2^+$ 392.1645 found 392.1649 [M$^+$]. Luminescence spectroscopy (in MeCN): $\lambda_{abs1}$: 503 nm; $\lambda_{abs2}$: 409 nm; $\lambda_{abs3}$: 289 nm; $\varepsilon_{abs1}$: 3.2·10$^3$ L cm mol$^{-1}$; $\lambda_{abs2}$: 4.2·10$^3$ L cm mol$^{-1}$; $\varepsilon_{abs3}$: 5.0·10$^4$ L cm mol$^{-1}$ $\lambda_{em}$(exc 493): 596 nm; Stokes shift: 93 nm; $E_{0,0}$: 2.33 eV; <τ$_F$>: 3.4 ns; Cyclic voltammetry (vs SCE): $E_{1/2}$(P*/P$^-$):+1.74 V, $E_{1/2}$(P/P$^-$): 0.49 V.

Example 18

1-Methoxy-10-methyl-9-phenylacridinium bromide

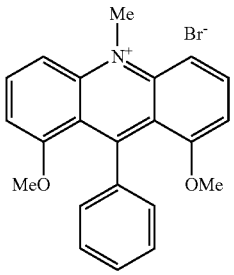 [SMILES: COc1cccc2c1c(-c1ccccc1)c1c(OC)cccc1[n+]2C ; [Br-]]

The compound was prepared according to the general procedure I, described in Example 3, using 2-bromo-N-(3-methoxyphenyl)-N-methylaniline (46.7 mg, 160 µmol) in n-hexane:Et$_2$O (10:1, 2.2 mL) and general procedure III, described in Example 5, using methyl benzoate (13.6 mg, 100 µmol) and was stirred 12 h at RT. Purification gave a brown red solid (20.0 mg, 53%, decomp. at 160° C.): R$_f$ 0.06 (CH$_2$Cl$_2$:MeOH 10:1); ν$_{max}$ (neat): 3364 w, 3012 w, 1604 s, 1577 m, 1554 m, 1516 m, 1466 s, 1355 s, 1252 s, 1176 m, 1079 m, 1017 m, 925 w, 762 s, 699 s, 660s; $^1$H NMR (500 MHz, CDCl$_3$): δ =8.93 (1H, d, $^3$J 9.2, C5H), 8.36-8.40 (3H, m, C3H, C4H, C6H), 7.82 (1H, dd, $^3$J 8.7, $^4$J 1.2, C8H), 7.71 (1H, dd, $^3$J 8.6, 6.9, C7H), 7.58-7.60 (3H, m, C3'H, C4'H, C5'H), 7.26-7.30 (2H, m, C2'H, C6'H), 7.13 (1H, dd, $^3$J 6.0, $^4$J 2.6, C2H), 5.18 (3H, s, NCH$_3$), 3.58 (3H, s, OCH$_3$); $^{13}$C NMR (125 MHz, CDCl$_3$): δ=160.6 (C9), 159.4 (C1), 142.7 (C4a), 141.2 (C3), 141.1 (C10a), 139.0 (C6), 137.6 (C1'), 130.4 (C8), 128.6 (C4'), 128.0 (C3', C5'), 127.3 (C7), 127.2 (C2', C6'), 126.5 (C8a), 119.2 (C9a), 119.1 (C5), 110.7 (C4), 106.6 (C2), 56.7 (OCH$_3$), 41.5 (NCH$_3$); ESI-MS: m/z calcd. for C$_{21}$H$_{18}$NO$^-$ 300.1383 found 300.1380 [M$^+$]. Luminescence spectroscopy (in MeCN): λ$_{abs1}$: 473 nm; λ$_{abs2}$: 362 nm; λ$_{abs3}$: 281 nm; ε$_{abs1}$: 4.7·10$^3$ L cm mol$^{-1}$; ε$_{abs2}$: 1.2·10$^4$ L cm mol$^{-1}$; ε$_{Eabs3}$: 5.7·10$^4$ L cm mol$^{-1}$; λ$_{em}$(exc 352): 502 nm; Stokes shift: 29 nm; E$_{0,0}$: 2.53 eV; <τ$_F$>: 16 ns (τ$_{1,2}$: 3.6, 24.3 ns); Cyclic voltammetry (vs SCE): E$_{1/2}$(P*/P$^-$): +2.05 V, E$_{1/2}$(P/$^-$): −0.48 V.

Example 19

6-(Dimethylamino)-1-methoxy-10-methyl-9-phenylacridinium bromide

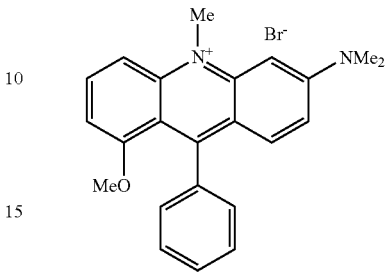

The compound was prepared according to the general procedure I, described in Example 3, using 4-bromo-N$^3$-(3-methoxyphenyl)-N$^1$,N$^1$,N$^3$-trimethylbenzene-1,3-diamine (53.6 mg, 160 µmol) in n-hexane:Et$_2$O (10:1, 2.2 mL) and general procedure III, described in Example 5, using methyl benzoate (13.6 mg, 100 µmol) and was stirred 12 h at RT. Purification gave a brown red solid (41.3 mg, 98%, decomp. at 150° C.): R$_f$ 0.11 (CH$_2$Cl$_2$:MeOH 10:1); ν$_{max}$ (neat): 3406 w, 2931 w, 2169 w, 1623 s, 1599 s, 1506 s, 1470 m, 1382 m, 1344 m, 1266 s, 1248 s, 1078 m, 1027 w, 925 w, 810 m, 707 m, 635 m; $^1$H NMR (500 MHz, CDCl$_3$): δ=7.94 (1H, dd, $^3$J 8.8, 8.3, C3H), 7.74 (1H, d, 9.0, C4H), 7.50-7.52 (3H, m, C3'H, C4'H, C5'H), 7.42 (1H, d, $^3$J 9.9, C8H), 7.19-7.21 (3H, m, C5H, C2'H, C6'H), 7.11 (1H, dd, $^3$J 9.9, $^4$J 2.2, C7H), 6.81 (1H, d, $^3$J 8.0, C2H), 4.72 (3H, s, NCH$_3$), 3.50 (6H, br, N(CH$_3$)$_2$), 3.46 (3H, s, OCH$_3$); $^{13}$C NMR (125 MHz, CDCl$_3$): δ=159.3 (C1), 156.3 (C6), 154.6 (C9), 144.4 (C10a), 142.1 (C4a), 138.4 (C1'), 137.1 (C3), 132.1 (C8), 127.9 (C4'), 127.8 (C3', C5'), 127.5 (C2', C6'), 121.2 (C8a), 117.2 (C7), 115.0 (C9a), 109.1 (C4), 105.1 (C2), 93.8 (C5), 56.1 (OCH$_3$), 41.6 (N(CH$_3$)$_2$), 39.9 (NCH$_3$); ESI-MS: m/z calcd. for C$_{23}$H$_{23}$N$_2$O$^+$ 343.1805 found 343.1804 [M$^-$]. Luminescence spectroscopy (in MeCN): λ$_{abs1}$: 506 nm; λ$_{abs2}$: 429 nm; λ$_{abs3}$: 289 nm; ε$_{abs1}$: 1.0·10$^4$ L cm mol$^{-1}$; ε$_{abs2}$: 1.5·10$^4$ L cm mol$^{-1}$; ε$_{abs3}$: 3.1·10$^4$ L cm mol$^{-1}$; λ$_{em}$(exc 496): 547 nm; Stokes shift: 41 nm; E$_{0,0}$: 2.35 eV; <τ$_F$>: 4.5 ns; Cyclic voltammetry (vs SCE): E$_{1/2}$(P*/P$^-$): +1.52 V, E$_{1/2}$(P/P$^-$): 0.83 V.

Example 20

6-(Dimethylamino)-9-(4-fluorophenyl)-1-methoxyxanthylium bromide/chloride

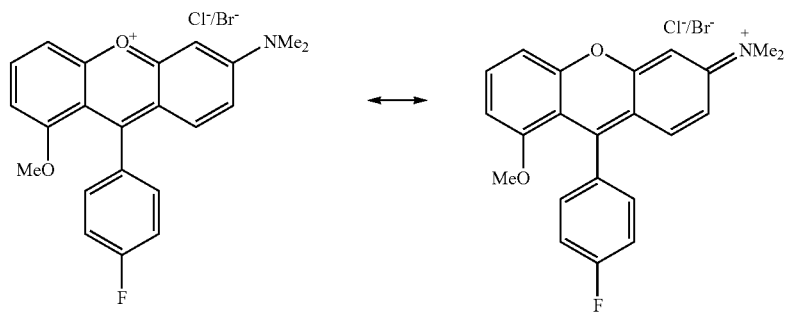

The compound was prepared according to the general procedure II and IV described in Example 4 and 6 using 4-bromo-3-(3-methoxyphenoxy)-N,N-dimethylaniline (45.1 mg, 140 μmol) and methyl 4-fluorobenzoate (15.4 mg, 100 μmol). Purification gave a brown red solid (7.50 mg, 20%, decomp. at 90° C.): $R_f$ 0.14 (CH$_2$Cl$_2$:MeOH 10:1); $v_{max}$ (neat): 3391 w, 3036 w, 2928 w, 1633 s, 1595 s, 1471 s, 1433 s, 1385 s, 1342 m, 1270 s, 1213 s, 1135 m, 1081 s, 914 m, 796 s, 717 s; $^1$H NMR (500 MHz, CDCl$_3$): δ=7.87-7.91 (1H, m, C3H), 7.48 (1H, dd, $^3$J 9.9, $^4$J2.4, C7H), 7.37 (1H, dd, $^3$J8.5, $^4$J0.9, C4H), 7.36 (1H, d, $^3$J9.9, C8H), 7.24-7.26 (4H, m, C2'H, C3'H), 7.00 (1H, d, $^4$J 2.5, C5H), 6.89 (1H, dd, $^3$J 8.4, $^4$J 0.6, C2H), 3.65 (3H, br, N(CH$_3$)$_2$), 3.58 (3H, br, N(CH$_3$)$_2$), 3.55 (3H, s, OCH$_3$); $^{13}$C NMR (125 MHz, CDCl$_3$): δ=163.0 ($^1$J$_{CF}$ 250 Hz, CF), 159.6 (C6), 159.4 (C1), 158.4 (C10a), 157.9 (C9), 154.8 (C4a), 138.7 (C3), 132.8 (C8), 131.4 ($^4$J$_{CF}$ 3.7 Hz, C1'), 129.4 ($^3$J$_{CF}$ 8.2 Hz, C2), 119.6 (C8a), 119.3 (C7), 115.4 ($^2$J$_{CF}$ 250 Hz, C3), 110.2 (C4), 107.5 (C2), 96.6 (C5), 56.4 (OCH$_3$), 42.7 (N(CH$_3$)$_2$); $^{19}$F NMR: 111.4; ESI-MS: m/z calcd. for C$_{22}$H$_{19}$FNO$_2^+$ 348.1394 found 348.1398 [M$^+$]. Luminescence spectroscopy (in MeCN): $\lambda_{abs}$: 490 nm, $c_{abs}$: 2.7·10$^4$ cm mol$^{-1}$, $\lambda_{em}$(exc 400): 570 nm; $E_{0,0}$: 2.33 eV; Stokes shift: 80 nm; <$\tau_F$>: 3.5 ns; Cyclic voltammetry (vs SCE): $E_{1/2}$(P*/P$^-$): +1.89 V, $E_{1/2}$(P/P$^-$): −0.44 V.

Example 21

6-(Dimethylamino)-1-methoxy-9,10-diphenylacridinium bromide

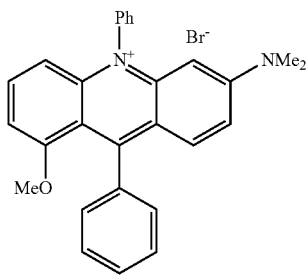 [SMILES: COc1cccc2c1c(-c1ccccc1)c1ccc(N(C)C)cc1[n+]2C ; [Br-]]

The compound was prepared according to the general procedure I, described in Example 3, using 4-bromo-N$^3$-(3-methoxyphenyl)-N$^1$,N$^1$-dimethyl-N$^3$-phenylbenzene-1,3-diamine (63.5 mg, 160 μmol) in n-hexane:Et$_2$O (10:1, 2.2 mL) and general procedure III, described in Example 5, using methyl benzoate (13.6 mg, 100 μmol) and was stirred 12 h at RT. Purification gave a brown red solid (44.3 mg, 91%, decomp. at 156° C.): $R_f$ 0.21 (CH$_2$Cl$_2$:MeOH 10:1); $v_{max}$ (neat): 3371 w, 2935 w, 2165 w, 1623 m, 1597 s, 1500 s, 1431 m, 1383 m, 1343 m, 1255 s, 1213 m, 1179 m, 1096 m, 1002 w, 922 m, 813 w, 721 s, 697 s, 647 w;

$^1$H NMR (500 MHz, CDCl$_3$): δ=7.88-7.91 (2H, m, C3"H, C5"H), 7.81-7.84 (1H, m, C4"H), 7.73 (1H, dd, $^3$J 8.8, 8.2, C3H), 7.53-7.57 (3H, m, C3'H, C4'H, C5'H), 7.50 (1H, d, $^3$J9.9, C8H), 7.47-7.48 (2H, m, C2"H, C6"H), 7.30-7.32 (2H, m, C2'H, C6'H), 7.24 (1H, dd, $^3$J 10, $^4$J2.5, C7H), 6.87 (1H, d, $^3$J 8.0, C2H), 6.68 (1H, dd, $^3$J 8.9, $^4$J 0.6, C4H), 5.79 (1H, d, $^4$J 2.4, C5H), 3.51 (3H, s, OCH$_3$), 3.18 (6H, br, N(CH$_3$)$_2$); $^{13}$C NMR (125 MHz, CDCl$_3$): δ=159.3 (C1), 156.4 (C9), 156.1 (C6), 144.9 (C10a), 142.3 (C4a), 137.9 (C1"), 137.0 (C3), 132.2 (C8), 132.0 (C3", C5"), 131.3 (C4"), 128.2 (C4'), 128.0 (C3', C5'), 127.9 (C2", C6"), 127.4 (C2', C6'), 121.0 (C8a), 117.8 (C7), 114.7 (C9a), 110.1 (C4), 105.7 (C2), 93.4 (C5), 56.4 (OCH$_3$), 41.0 (N(CH$_3$)$_2$); ESI-MS: m/z calcd. for C$_{28}$H$_{25}$N$_2$O$^+$ 405.1961 found 405.1969 [M$^{-1}$]. Luminescence spectroscopy (in MeCN): $\lambda_{abs1}$: 511 nm; $\lambda_{abs2}$: 488 nm; $\lambda_{abs3}$: 433 nm; $\lambda_{abs4}$: 292 nm; $\varepsilon_{abs1}$: 1.0·10$^4$ L cm mol$^{-1}$; $\varepsilon_{abs2}$: 1.0·10$^4$ L cm mol$^{-1}$; $\varepsilon_{abs3}$: 1.6·10$^4$ L cm mol$^{<1}$; $\varepsilon_{abs4}$: 3.1·10$^4$ L cm mol$^{-1}$; $\lambda_{em}$(exc 501): 567 nm; Stokes shift: 57 nm; $E_{0,0}$: 2.30 eV; Cyclic voltammetry (vs SCE): $E_{1/2}$(P*/P$^-$): +1.41 V, $E_{1/2}$(P/P$^-$): −0.89 V.

Example 22

9-Mesityl-1,8-dimethoxy-10-methylacridinium bromide

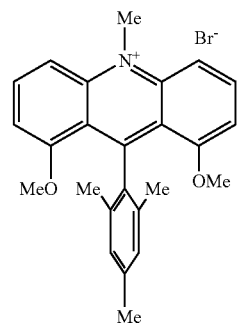 [SMILES: COc1cccc2c1c(-c1c(C)cc(C)cc1C)c1c(OC)cccc1[n+]2C ; [Br-]]

The compound is prepared according to the general procedure I and III described in Example 3 and 5 using 3-methoxy-N-(3-methoxyphenyl)-N-methylaniline (38.9 mg, 160 μmol) and e.g. methyl 2,4,6-trimethylbenzoate (17.8 mg, 100 μmol).

Example 23

9-Mesityl-1-methoxy-10-methylacridinium bromide

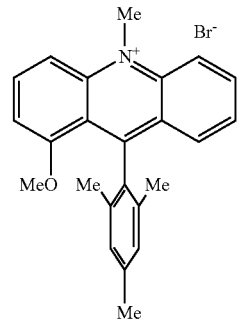 [SMILES: COc1cccc2c1c(-c1c(C)cc(C)cc1C)c1ccccc1[n+]2C ; [Br-]]

The compound is prepared according to the general procedure I and III described in Example 3 and 5 using 2-bromo-N-(3-methoxyphenyl)-N-methylaniline (46.7 mg, 160 μmol) and e.g. methyl 2,4, 6-trimethylbenzoate (17.8 mg, 100 μmol).

Example 24

6-(Dimethylamino)-9-mesityl-1-methoxy-10-methyl-acridinium bromide

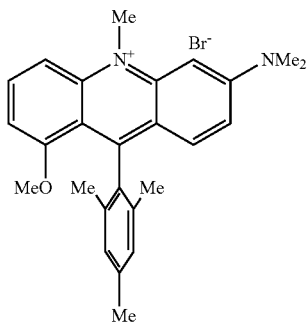 [SMILES: COc1cccc2c1c(-c1c(C)cc(C)cc1C)c1ccc(N(C)C)cc1[n+]2C ; [Br-]]

The compound is prepared according to the general procedure I and III described in Example 3 and 5 using 4-bromo-N³-(3-methoxyphenyl)-N¹,N¹,N³-trimethylbenzene-1,3-diamine (53.6 mg, 160 μmol) and e.g. methyl 2,4,6-trimethylbenzoate (17.8 mg, 100 μmol).

Example 25

3,6-Bis(dimethylamino)-9-mesityl-1-methoxy-10-methylacridinium bromide

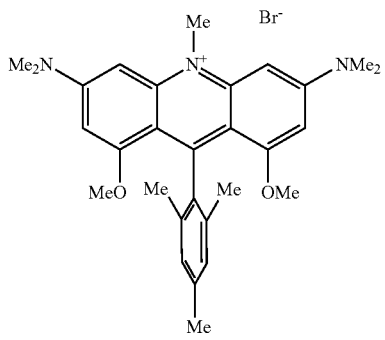 [SMILES: [Br-] ; COc1cc(N(C)C)cc2c1c(-c1c(C)cc(C)cc1C)c1c(OC)cc(N(C)C)cc1[n+]2C]

The compound is prepared according to the general procedure I and III described in Example 3 and 5 using 4-bromo-N³-(3-(dimethylamino)-5-methoxyphenyl)-N¹,N¹,N³-trimethylbenzene-1,3-diamin (60.5 mg, 160 gmol) and e.g. methyl 2,4,6-trimethylbenzoate (17.8 mg, 100 μmol).

Example 26

3,6-Bis(dimethylamino)-9-mesityl-1,8-dimethoxy-10-methylacridinium bromide

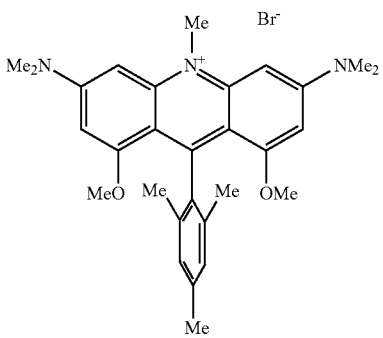 [SMILES: [Br-] ; COc1cc(N(C)C)cc2c1c(-c1c(C)cc(C)cc1C)c1c(OC)cc(N(C)C)cc1[n+]2C]

The compound is prepared according to the general procedure I and III described in Example 3 and 5 using N¹-(3-(dimethylamino)-5-methoxyphenyl)-5-methoxy-N¹,N³,N³-trimethylbenzene-1,3-diamine (52.7 mg, 160 μmol) and e.g. methyl 2,4,6-trimethylbenzoate (17.8 mg, 100 μmol).

Example 27

3-(Dimethylamino)-9-mesityl-1-methoxy-10-methyl-acridinium bromide

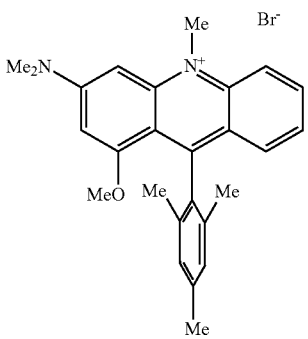 [SMILES: [Br-] ; COc1cc(N(C)C)cc2c1c(-c1c(C)cc(C)cc1C)c1ccccc1[n+]2C]

The compound is prepared according to the general procedure I and III described in Example 3 and 5 using N¹-(2-bromophenyl)-5-methoxy-N¹,N³,N³-trimethylbenzene-1,3-diamine (53.4 mg, 160 μmol) and e.g. methyl 2,4,6-trimethylbenzoate (17.8 mg, 100 μmol).

Example 28

3-(Dimethylamino)-1,8-dimethoxy-9,10-diphenylacridinium bromide salt

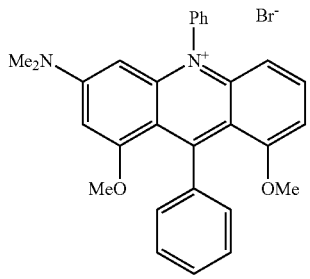 [SMILES: [Br-] ; COc1cccc2c1c(-c1ccccc1)c1c(OC)cc(N(C)C)cc1[n+]2-c1ccccc1]

The compound was prepared according to the general procedure I, described in Example 3, using 5-methoxy-$N^1$-(3-methoxyphenyl)-$N^3$,$N^3$-dimethyl-$N^1$-phenylbenzene-1,3-diamine (55.8 mg, 160 μmol) in n-hexane (2.0 mL) and general procedure III, described in Example 5, using methyl benzoate (13.6 mg, 100 μmol) and was stirred 14 h at RT. Purification gave a brown red solid (13.6 mg, 26%, decomp. at 117° C.): $R_f$ 0.18 (CH$_2$Cl$_2$:MeOH 10:1); $v_{max}$ (neat): 3387 w, 2926 m, 2361 m, 2178 w, 1623 s, 1597 s, 1501 s, 1428 s, 1373 m, 1349 m, 1295 m, 1255 s, 1182 m, 1096 s, 973 m, 921 m, 806 w, 771 m, 723 s, 697 s, 652 w; $^1$H NMR (500 MHz, CDCl$_3$): δ=7.84-7.87 (2H, m, C3"H, C5"H), 7.76-7.79 (1H, m, C4"H), 7.58 (1H, dd, $^3$J8.6, 8.3, C6H), 7.38-7.43 (5H, m, C3'H, C4'H, C5'H, C2"H, C6"H), 7.20 (2H, dd,$^3$J7.5, $^4$J1.3, C2'H, C6'H), 6.71 (1H, d, $^3$J8.0, C7H), 6.51 (1H, d, $^3$J8.6, C5H), 6.41 (1H, d, $^4$J 1.1, C2H), 5.42 (1H, d, $^4$J 1.1, C4H), 3.52 (3H, s, OCH$_3$), 3.38 (3H, s, OCH$_3$), 3.19 (6H, br, N(CH$_3$)$_2$); $^{13}$C NMR (125 MHz, CDCl$_3$): δ=161.3 (C1), 160.0 (C8), 157.3 (C3), 156.1 (C9), 145.4 (C4a), 142.0 (C10a), 141.6 (C1'), 138.7 (C1"), 136.2 (C6), 132.0 (C3", C5"), 131.0 (C4"), 128.0 (C2", C6"), 126.8 (C3', C5'), 126.7 (C4'), 125.9 (C2', C6'), 115.5 (C9a), 114.7 (C8a), 109.6 (C5), 105.7 (C7), 95.8 (C2), 89.1 (C4), 57.0 (C1OCH$_3$), 56.3 (C8OCH$_3$), 41.3 (N(CH$_3$)$_2$); ESI-MS: m/z calcd. for C$_{29}$H$_{27}$N$_2$O$_2$$^+$ 435.2067 found 435.2073 [M$^+$]. Luminescence spectroscopy (in MeCN): $\lambda_{abs1}$: 501 nm; $\lambda_{abs2}$: 430 nm; $\lambda_{abs3}$: 310 nm; $E_{abs1}$: 8.6·10$^3$ L·cm·mol$^{-1}$; $\varepsilon_{abs2}$: 1.6·10$^4$ Lcm mol$^{-1}$; $\varepsilon_{abs3}$: 3.7·10$^4$ L·cm·mol$^{-1}$; $\lambda_{em}$(exc 491): 584 nm; $\lambda_{em}$(exc 420): 589 nm; Stokes shift: 83 nm; $E_{0,0}$: 2.25 eV; <$\tau_F$>: 4.7 ns; Cyclic voltammetry (vs SCE): $E_{1/2}$(P*/P$^-$): +1.31 V, $E_{1/2}$(P/P$^-$): −0.94 V.

Example 29

(±)-3-(Dimethylamino)-1,8-dimethoxy-9-(naphthalen-1-yl)-10-phenylacridinium bromide salt

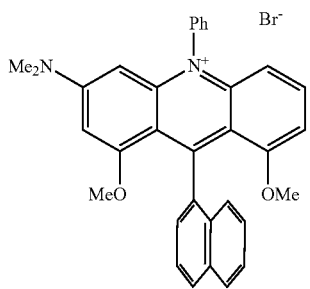 [SMILES: [Br-] ; COc1cccc2c1c(-c1cccc3ccccc13)c1c(OC)cc(N(C)C)cc1[n+]2-c1ccccc1]

The compound was prepared according to the general procedure I, described in Example 3, using 5-methoxy-$N^1$-(3-methoxyphenyl)-$N^3$,$N^3$-dimethyl-$N^1$-phenylbenzene-1,3-diamine (55.8 mg, 160 μmol) in n-hexane (2.0 mL) and general procedure III, described in Example 5, using methyl 1-naphthoate (18.6 mg, 100 mol) and was stirred 12 h at RT. Purification gave a brown red solid (14.4 mg, 26%, decomp. at 131° C.): $R_f$=0.12 (CH$_2$Cl$_2$/MeOH, 10:1); IR (neat): $v_{max}$=3369 w, 2925 w, 2361 w, 1623 s, 1598 s, 1497 s, 1475 s, 1427 m, 1377 m, 1349 s, 1255 s, 1168 w, 1102 s, 972 m, 785 s, 768 s, 707 m; $^1$H NMR (500 MHz, CDCl$_3$): δ=7.95 (1H, d, $^3$J8.2, C5'H), 7.87-7.91 (3H, m, C4'H, C3"H, C5"H), 7.79-7.81 (1H, m, C4"H), 7.60 (1H, t, $^3$J 8.4, C6H), 7.46-7.52 (4H, m, C3'H, C6'H, C2"H, C6"H), 7.41-7.42 (1H, m, C8'H), 7.34-7.37 (1H, m, C7'H), 7.09 (1H, d, $^3$J 6.9, C2'H), 6.64 (1H, d, $^3$J 8.0 Hz, C7H), 6.57 (1H, d, $^3$J 8.8 Hz, C5H), 6.32 (1H, d, $^4$J 1.2, C2H), 5.48 (1 H, d, $^4$J 1.3, C4H), 3.14 (3H, s, ClOCH$_3$), 3.12 (6H, br, N(CH$_3$)$_2$), 2.99 (3H, s, C8OCH$_3$); $^{13}$C NMR (125 MHz, CDCl$_3$): δ=161.1 (C1), 159.8 (C8), 157.3 (C3), 155.1 (C9), 145.3 (C4a), 142.0 (C10a), 140.0 (C1), 138.7 (C1'), 136.4 (C6), 132.2 (C4'a), 132.2 (C3'), 132.1 (C8'a), 132.0 (C5'), 131.1 (C4'), 128.1 (C5), 128.1 (C2'), 128.0 (C6'), 127.0 (C4), 126.0 (C7), 125.6 (C6), 125.1 (C8), 124.9 (C3), 121.9 (C2), 116.4 (C9a), 115.3 (C8a), 109.7 (C5), 106.0 (C7), 95.9 (C2), 89.1 (C4), 56.8 (ClOCH$_3$), 56.2 (C8OCH$_3$), 41.2 (N(CH$_3$)$_2$); ESI-MS: m/z calcd for C$_{33}$H$_{29}$N$_2$O$_2$$^1$: 485.2224; found: 485.2226 [M$^{-1}$]; Luminescence spectroscopy (in MeCN): $\lambda_{abs1}$: 504 nm; $\lambda_{abs2}$: 431 nm; $\lambda_{abs3}$: 311 nm; $\varepsilon_{abs1}$: 8.510$^3$ L cm mol$^-$; $\varepsilon_{abs2}$: 1.6.10$^4$ L cm mol$^{-1}$; $\varepsilon_{abs3}$: 4.110$^4$ L cm mol$^{-1}$; $\lambda_{em}$(exc 495 nm): 590 nm; Stokes shift: 86 nm; $E_{0,0}$: 2.22 eV. Cyclic voltammetry (in MeCN, vs. SCE): $E_{1/2}$(P*/P$^-$): +1.36 V; $E_{1/2}$(P/P$^-$): −0.86 V.

Example 30

(±)-3-(Dimethylamino)-9-(4-fluoronaphthalen-1-yl)-1,8-dimethoxy-10-phenylacridinium bromide salt

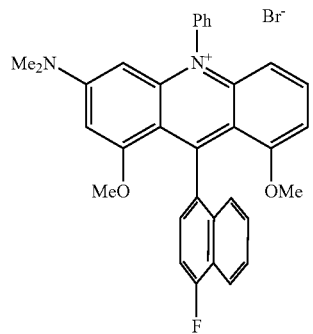 [SMILES: [Br-] ; COc1cccc2c1c(-c1ccc(F)c3ccccc13)c1c(OC)cc(N(C)C)cc1[n+]2-c1ccccc1]

The compound was prepared according to the general procedure I, described in Example 3, using 5-methoxy-$N^1$-(3-methoxyphenyl)-$N^3$,$N^3$-dimethyl-$N^1$-phenylbenzene-1,3-diamine (55.8 mg, 160 μmol) in n-hexane (2.0 mL) and general procedure III, described in Example 5, using 4-fluoro-1-naphthoate (20.4 mg, 100 mol) and was stirred 12 h at RT. Purification gave a brown red solid (20.1 mg, 34%, decomp. at 134° C.): $R_f$=0.14 (CH$_2$Cl$_2$/MeOH, 10:1). IR (neat): $v_{max}$=2934 w, 1623 s, 1598 s, 1503 s, 1469 s, 1429 m, 1348 m, 1256 s, 1233 m, 1166 w, 1098 s, 1036 w, 907 w, 767 s, 707 m; $^1$H NMR (500 MHz, CDCl$_3$): δ=8.22 (1H, d, $^3$J 8.8, C5'H), 7.87-7.91 (2H, m, C3"H, C5"H), 7.78-7.81

(1H, m, C4"H), 7.55-7.61 (2H, m, C6'H, C6H), 7.46-7.52 (2H, m, C2"H, C6"H), 7.43-7.44 (2H, m, C7'H, C8'H), 7.17-7.21 (1H, m, C3'H), 7.01-7.04 (1H, m, C2'H), 6.64 (1H, d, $^3J$ 7.9, C7H), 6.57 (1H, d, $^3J$ 8.8, C5H), 6.36 (1H, d, $^4J$ 1.2, C2H), 5.48 (1H, d, $^4J$ 1.2, C4H), 3.20 (3H, s, C1OCH$_3$), 3.12 (6H, br, N(CH$_3$)$_2$), 3.04 (3H, s, C8OCH$_3$); $^{13}$C NMR (125 MHz, CDCl$_3$): δ=160.9 (C1), 159.6 (C8), 158.0 (d, $^2J_{CF}$ 251, C4), 157.3 (C3), 154.0 (C9), 145.3 (C4a), 142.1 (C10a), 138.7 (C1'), 136.3 (C6), 135.9 (d, $^4J_{CF}$ 4.8, C1), 133.5 (d, $^3J_{CF}$ 4.7, C8'a), 132.2 (C3'), 132.0 (C5"), 131.1 (C4'), 128.1 (C2'), 128.0 (C6'), 127.1 (C7), 126.0 (C6), 125.2 (d, $^4J_{CF}$ 2.6, C8), 122.6 (d, $^2J_{CF}$ 17.0, C4'a), 121.6 (d, $^3J_{CF}$ 8.2, C2), 120.6 (d, $^3J_{CF}$ 5.1, C5), 116.8 (C9a), 115.3 (C8a), 109.8 (C5), 108.5 (d, $^2J_{CF}$ 20.4, C3), 105.9 (C7), 96.2 (C2), 89.2 (C4), 56.9 (C8OCH$_3$), 56.2 (C1OCH$_3$), 41.0 (N(CH$_3$)$_2$); $^{19}$F NMR (471 MHz, CDCl$_3$): δ=124.6; ESI-MS: m/z calcd for C$_{33}$H$_{28}$FN$_2$O$_2$': 503.2128; found: 503.2129 [M$^+$]; Luminescence spectroscopy (in MeCN): λ$_{abs1}$: 501 nm; λ$_{abs2}$: 430 nm; λ$_{abs3}$: 311 nm; ε$_{abs1}$: 5.9·10$^3$ L cm mol$^{-1}$; ε$_{abs2}$: 1.0·10$^4$ L cm mol$^{-1}$; ε$_{abs3}$: 2.9·10$^4$ L cm mol$^{-1}$; λ$_{em}$(exc 496 nm): 591 nm; Stokes shift: 90 nm; E$_{0,0}$: 2.22 eV; Cyclic voltammetry (in MeCN, vs. SCE): E$_{1/2}$(P*/P$^-$): +1.37 V; E$_{1/2}$(P/P$^-$): −0.85 V.

Example 31

3,6-Bis(dimethylamino)-1,8-dimethoxy-9,10-diphenylacridinium bromide salt

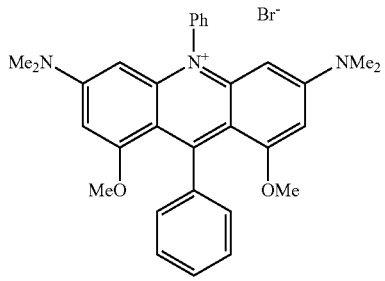 [SMILES: [Br-] ; COc1cc(N(C)C)cc2c1c(-c1ccccc1)c1c(OC)cc(N(C)C)cc1[n+]2-c1ccccc1]

The compound was prepared according to the general procedure I, described in Example 3, using N$^1$-(3-(dimethylamino)-5-methoxyphenyl)-5-methoxy-N$^3$,N$^3$-dimethyl-N$^1$-phenylbenzene-1,3-diamine (62.6 mg, 160 μmol) in-hexane (2.0 mL) and general procedure III, described in Example 5, using methyl benzoate (13.6 mg, 100 μmol) and was stirred 14 h at RT. Purification gave a brown red solid (19.7 mg, 35%, decomp. at 148° C.): R$_f$ 0.17 (CH$_2$Cl$_2$:MeOH 10:1); v$_{max}$ (neat): 2925 w, 2360 w, 2166 w, 1599 s, 1490 m, 1433 w, 1333 m, 1254 s, 975 w, 923 w, 781 m, 630 w; $^1$H NMR (500 MHz, CDCl$_3$): δ=7.82-7.85 (2H, m), 7.73-7.76 (1H, m), 7.38-7.40 (4H, m, C2'H, C6'H, C2"H, C6"H), 7.33-7.36 (1H, m), 7.17-7.18 (2H, m), 6.07 (2H, d, $^4J$ 1.9, C2H, C7H), 5.36 (2H, d, $^4J$ 1.8, C4H, C5H), 3.38 (6H, s, 2×OCH$_3$), 3.00 (12H, s, 2×N(CH$_3$)$_2$); $^{13}$C NMR (125 MHz, CDCl$_3$): δ=161.3 (C1, C8), 155.4 (C3, C6), 154.6, 144.9 (C4a, C5a), 142.2 (C9), 139.2, 131.9, 130.6, 128.1, 126.7, 126.3, 126.0, 109.8 (C8a, C9a), 93.3 (C2, C7), 89.5 (C4, C5), 56.1 (OCH$_3$), 40.3 (N(CH$_3$)$_2$); ESI-MS: m/z calcd. for C$_{31}$H$_{32}$N$_3$O$_2$' 478.2489 found 478.2495 [M$^+$]. Luminescence spectroscopy (in MeCN): λ$_{abs1}$: 498 nm; λ$_{abs2}$: 296 nm; E$_{abs1}$: 4.0.10$^4$ Lcmmol'; E$_{abs2}$: 4.7.10$^4$ Lcmmol';

λ$_{em}$(exc 488): 540 nm; Stokes shift: 42 nm; E$_{0,0}$: 2.40 eV; <τ$_F$>: 4.4 ns; Cyclic voltammetry (vs SCE): E$_{1/2}$(P*/P$^-$): +1.21 V, E$_{1/2}$(P/P$^-$): −1.19 V.

Example 32

1-Methoxy-9,10-diphenylacridinium bromide salt

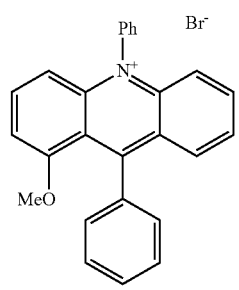 [SMILES: [Br-] ; COc1cccc2c1c(-c1ccccc1)c1ccccc1[n+]2-c1ccccc1]

The compound was prepared according to the general procedure I, described in Example 3, using 2-bromo-N-(3-methoxyphenyl)-N-phenylaniline (56.7mg, 160 μmol) in n-hexane:Et$_2$O (10:1, 2.2 mL) and general procedure III, described in Example 5, using methyl benzoate (13.6 mg, 100 μmol)_ and was stirred 12 h at RT. Purification gave a brown red solid (34.6 mg, 78%, decomp. at 135° C.): R$_f$ 0.21 (CH$_2$Cl$_2$:MeOH 10:1); v$_{max}$ (neat): 2985 w, 2161 w, 1605 m, 1578 m, 1513 m, 1468 s, 1359 m, 1273 m, 1249 s, 1197 w, 1091 s, 977 w, 926 w, 816 w, 787 s, 757 s, 725 s, 701 s, 669 m, 635 w; $^1$H NMR (500 MHz, CDCl$_3$): δ=8.14 (1H, dd, $^3$J 9.1, 8.1, C3H), 8.10 (1H, ddd, $^3$J 9.0, 6.8, 1.5, C6H), 7.91-7.94 (2H, m, C3"H, C5"H), 7.86-7.90 (2H, m, C8H, C4"H), 7.70-7.73 (3H, m, C7H, C2"H, 6"H), 7.60-7.63 (3H, m, C3'H, C4'H, C5'H), 7.43-7.45 (3H, m, C5H, C2'H, C6'H), 7.18 (1H, d, $^3$J 8.0, C2H), 7.04 (1H, d, $^3$J 8.6, C4H), 3.62 (3H, s, OCH$_3$); $^{13}$C NMR (125 MHz, CDCl$_3$): δ=162.7 (C9), 159.5 (C1), 143.3 (C4a), 141.5 (C10a), 141.2 (C3), 138.5 (C6), 137.5 (C1"), 137.3 (C1'), 131.9 (C4"), 131.8 (C3", C5"), 130.5 (C8), 128.8 (C4'), 128.0 (C3', C5'), 127.9 (C2", C6"), 127.6 (C7), 127.4 (C2', C6'), 126.5 (C8a), 119.4 (C9a), 119.1 (C5), 111.2 (C4), 107.1 (C2), 57.0 (OCH$_3$); ESI-MS: m/z calcd. for C$_{26}$H$_{20}$NO$^+$ 362.1539 found 362.1543 [M$^+$]. Luminescence spectroscopy (in MeCN): λ$_{abs1}$: 470 nm; λ$_{abs2}$: 362 nm; λ$_{abs3}$: 282 nm; ε$_{abs1}$: 5.1·10$^3$ L cm mol$^{-1}$; ε$_{abs2}$: 1.1·10$^4$ L cm mol$^{-1}$; ε$_{abs3}$: 4.9.10$^4$ L cm mol$^{-1}$; λ$_{em}$(exc 490): 604 nm; Stokes shift: 125 nm; E$_{0,0}$: 2.28 eV; Cyclic voltammetry (vs SCE): E$_{1/2}$(P*/P$^-$): +1.74 V, E$_{1/2}$(P/P$^-$): −0.54 V.

Example 33

9-Mesityl-1-methoxy-10-phenylacridinium bromide salt

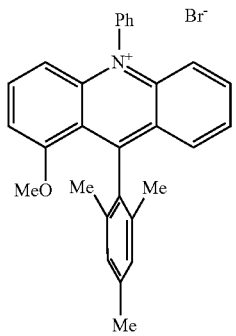 [SMILES: [Br-] ; COc1cccc2c1c(-c1c(C)cc(C)cc1C)c1ccccc1[n+]2-c1ccccc1]

The compound was prepared according to the general procedure I, described in Example 3, using 2-bromo-N-(3-methoxyphenyl)-N-phenylaniline (56.7 mg, 160 μmol) in n-hexane:Et$_2$O (10:1, 2.2 mL) and general procedure III, described in Example 5, using methyl 2,4,6-trimethylbenzoate (17.8 mg, 100 μmol) and was stirred 12 h at RT. Purification gave a brown red solid (34.3 mg, 71%, decomp. at 139° C.): R$_f$ 0.21 (CH$_2$Cl$_2$:MeOH 10:1); ν$_{max}$ (neat): 3002 w, 2913 w, 2361 w, 1609 m, 1582 m, 1549 m, 1518 m, 1462 s, 1372 m, 1265 m, 1242 s, 1189 m, 1090 s, 1034 w, 983 w, 846 w, 808 w, 770 s, 736 m, 702 m, 672 w, 629 w; $^1$H NMR (500 MHz, CDCl$_3$): δ=8.22 (1H, dd, $^3$J 9.1, 8.1, C3H), 8.14 (1H, ddd, $^3$J 9.0, 6.8, $^4$J 1.6, C6H), 7.94-7.97 (2H, m, C3"H, C5"H), 7.88-7.91 (1H, m, C4"H), 7.80-7.82 (1H, m, C8H), 7.74 (1H, ddd, $^3$J 9.0, 6.7, $^4$J 1.0, C7H), 7.69-7.71 (2H, m, C2"H, C6"H), 7.48-7.49 (1H, m, C5H), 7.28-7.29 (1H, m, C2H), 7.07-7.09 (3H, m, C4H, C3'H, C5'H), 3.71 (3H, s, OCH$_3$), 2.47 (3H, s, CH$_3$), 1.81 (6H, s, 2×CH$_3$); $^{13}$C NMR (125 MHz, CDCl$_3$): δ=164.3 (C9), 159.7 (C1), 143.1 (C4a), 141.5 (C3), 141.3 (C10a), 139.0 (C6), 138.7 (C4'), 137.3 (C1"), 133.9 (C1'), 133.6 (C2', C6'), 132.0 (C4"), 131.9 (C3", C5"), 129.1 (C8), 128.3 (C3', C5'), 128.2 (C7), 127.9 (C2", C6"), 125.5 (C8a), 119.6 (C9a), 119.5 (C5), 111.4 (C4), 107.1 (C2), 57.6 (OCH$_3$), 21.2 (CH$_3$), 20.4 (2×CH$_3$); ESI- MS: m/z calcd. for C$_{29}$H$_{26}$NO 404.2009 found 404.2016 [M$^+$]. Luminescence spectroscopy (in MeCN): λ$_{abs1}$: 479 nm; λ$_{abs2}$: 360 nm; λ$_{abs3}$: 283 nm; ε$_{abs1}$: 5.9·10$^3$ L cm mol$^{-1}$; ε$_{abs2}$: 1.3·10$^4$ L cm mol$^{-1}$; ε$_{abs3}$: 5.5·10$^4$ L cm mol$^{-1}$; λ$_{em}$(exc 479): 601 nm; Stokes shift: 122 nm; E$_{0,0}$: 2.28 eV; Cyclic voltammetry (vs SCE): E$_{1/2}$(P*/P$^-$): +1.71 V, E$_{1/2}$(P/P): −0.57 V.

Example 34

9-(2,6-Dimethylphenyl)-1-methoxy-10-phenylacridinium bromide salt

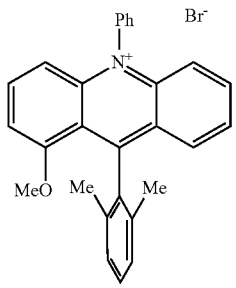 [SMILES: [Br-] ; COc1cccc2c1c(-c1c(C)cccc1C)c1ccccc1[n+]2-c1ccccc1]

The compound was prepared according to the general procedure I, described in Example 3, using 2-bromo-N-(3-methoxyphenyl)-N-phenylaniline (56.7mg, 160 μmol) in n-hexane:Et$_2$O (10:1, 2.2 mL) and general procedure III, described in Example 5, using methyl 2,6-dimethylbenzoate (16.4 mg, 100 μmol) and was stirred 12 h at RT. Purification gave a brown red solid (33.3 mg, 71%, decomp. at 139° C.): R$_f$ 0.14 (CH$_2$Cl$_2$:MeOH 10:1); ν$_{max}$ (neat): 3013 w, 2361 w, 1606 m, 1582 m, 1517 m, 1466 s, 1366 m, 1271 s, 1243 m, 1197 w, 1087 s, 1030 w, 977 w, 771 s, 738 m, 701 m, 670 w, 626 w; $^1$H NMR (500 MHz, CDCl$_3$): δ=8.22 (1H, dd, $^3$J 8.7, 8.4, C3H), 8.14 (1H, ddd, $^3$J 9.2, 7.0, $^4$J 1.5, C6H), 7.94-7.97 (2H, m, C3"H, C5"H), 7.88-7.91 (1H, m, C4"H), 7.78-7.80 (1H, m, C8H), 7.72-7.75 (3H, m, C7H, C2"H, C6"H), 7.51 (1H, $^3$J 9.0, C5H), 7.41 (1H, t, $^3$J 7.5, C4'H), 7.26-7.28 (3H, m, C2H, C3'H, C5'H), 7.10 (1H, d, $^3$J 9.1, C4H), 3.69 (3H, s, OCH$_3$), 1.86 (6H, s, 2×CH$_3$); $^{13}$C NMR (125 MHz, CDCl$_3$): δ=163.6 (C9), 159.6 (C1), 143.2 (C4a), 141.6 (C3), 141.4 (C10a), 138.9 (C6), 137.3 (C1"), 136.8 (C1'), 133.8 (C2', C6'), 132.0 (C4"), 131.9 (C3", C5"), 129.0 (C4'), 128.9 (C8), 128.3 (C7), 127.9 (C2", C6"), 127.6 (C3', C5'), 125.2 (C8a), 119.6 (C5), 119.4 (C9a), 111.6 (C4), 107.1 (C2), 57.5 (OCH$_3$) 20.6 (2×CH$_3$,); ESI-MS: m/z calcd. for C$_{28}$H$_{24}$NO$^+$ 390.1852 found 390.1857 [M$^+$]. Luminescence spectroscopy (in MeCN): λ$_{abs1}$: 480 nm; λ$_{abs2}$: 360 nm; λ$_{abs3}$: 283 nm; ε$_{abs1}$: 4.1·10$^3$ L cm mol$^{-1}$; ε$_{abs2}$: 9.7·10$^3$ L cm mol$^{-1}$; ε$_{abs3}$: 4.4·10$^4$ L cm mol$^{-1}$; λ$_{em}$(exc 390): 497 nm; Stokes shift: 17 nm; E$_{0,0}$: 2.52 eV; Cyclic voltammetry (vs SCE): E$_{1/2}$(P*/P$^-$): +1.96 V, E$_{1/2}$(P/P$^-$): −0.56 V.

Example 35

(±)-1-Methoxy-9-(naphthalen-1-yl)-10-phenylacridinium bromide salt

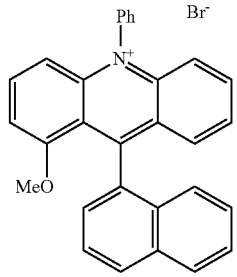 [SMILES: [Br-] ; COc1cccc2c1c(-c1cccc3ccccc13)c1ccccc1[n+]2-c1ccccc1]

The compound was prepared according to the general procedure I, described in Example 3, using 2-bromo-N-(3-methoxyphenyl)-N-phenylaniline (56.7mg, 160 μmol) in n-hexane:Et$_2$O (10:1, 2.2 mL) and general procedure III, described in Example 5, using methyl 1-naphthoate (18.6 mg, 100 μmol) and was stirred 12 h at RT. Purification gave a brown red solid (36.6 mg, 74%, decomp. at 156° C.): R$_f$ 0.22 (CH$_2$Cl$_2$:MeOH 10:1); ν$_{max}$ (neat): 3364 w, 3003 w, 2932 w, 2361 w, 1607 m, 1581 m, 1549 w, 1519 m, 1466 s, 1367 m, 1270 m, 1248 s, 1193 w, 1089 s, 1031 w, 975 w, 767 s, 704 s, 662 w; $^1$H NMR (500 MHz, CDCl$_3$): δ=8.12 (1H, $^3$J 9.5, 8.0, C3H), 8.08-8.10 (1H, m, C4'H), 8.03-8.07 (2H, m, C6H, C5"H), 7.91-7.98 (2H, m, C3"H, C5"H), 7.88-7.90 (2H, m, C2"H, C6"H), 7.85-7.87 (1H, m, C4"H), 7.71-7.73 (1H, m, C8H), 7.68-7.70 (1H, m, C3'H), 7.58 (1H, dd, $^3$J 6.6, $^4$J 1.0, C7H), 7.56 (1H, ddd, $^3$J 8.5, 7.5, $^4$J 0.9, C6'H), 7.49-7.52 (2H, m, C5H, C2'H), 7.38-7.41 (1H, m, C7'H), 7.27 (1H, ³J 8.6, ⁴J 0.9, C8'H), 7.10 (1H, ³J 9.0, ⁴J 0.6, C4H), 7.06 (1H, d, ³J 7.9, C2H), 3.26 (3H, s, OCH₃); ¹³C NMR (125 MHz, CDCl₃): δ=162.1 (C9), 159.2 (C1), 143.3 (C4a), 141.6 (C10a), 140.9 (C3), 138.5 (C6), 137.6 (C1"), 135.1 (C1'), 132.7 (C4'a), 131.9 (C3"), 131.8 (C5"), 131.7 (C4"), 131.5 (C8'a), 130.5 (C8), 129.1 (C4'), 128.4 (C5'), 128.2 (C2"), 128.0 (C6"), 127.5 (C7), 127.3 (C7'), 127.0 (C8a), 126.6 (C6'), 125.7 (C2), 125.6 (C8), 125.1 (C3'), 120.5 (C9a), 119.3 (C5), 111.4 (C4), 107.1 (C2), 56.9 (OCH₃); ESI- MS: m/z calcd. for $C_{30}H_{22}NO^+$ 412.1696 found 412.1702 [M⁺]. Luminescence spectroscopy (in MeCN): $\lambda_{abs1}$; 480 nm; $\lambda_{abs2}$: 362 nm; $\lambda_{abs3}$: 283 nm; $\varepsilon_{abs1}$: 5.4·10³ L cm mol⁻¹; $\varepsilon_{abs2}$: 1.2·10⁴ L cm mol⁻¹; $\varepsilon_{abs3}$: 5.8·10⁴ L cm mol⁻¹; $\lambda_{em}$(exc 470): 605 nm; Stokes shift: 125 nm; $E_{0,0}$: 2.28 eV; Cyclic voltammetry (vs SCE): $E_{1/2}(P^*/P^-)$: +1.75 V, $E_{1/2}(P/P^-)$: −0.53 V.

Example 36

(±)-1-Methoxy-10-methyl-9-(naphthalen-1-yl)acridinium bromide salt

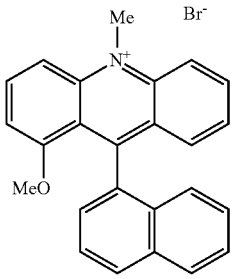

The compound was prepared according to the general procedure I, described in Example 3, using 2-bromo-N-(3-methoxyphenyl)-N-methylaniline (46.8 mg, 160 μmol) in n-hexane (2.0 mL) and general procedure III, described in Example 5, using methyl 1-naphthoate (18.6 mg, 100 μmol) and was stirred 12 h at RT. Purification gave a brown red solid (25.4 mg, 59%, decomp. at 166° C.): R_f 0.08 (CH₂Cl₂: MeOH 10:1); v. (neat): 3390 m, 3039 m, 1607 s, 1579 m, 1520 m, 1465 s, 1361 s, 1252 s, 1179 m, 1083 m, 1025 w, 936 w, 766 s, 738 w, 711 m; ¹H NMR (500 MHz, CDCl₃): δ=8.99 (1H, d, ³J 9.2, C5H), 8.49 (1H, d, ³J 9.1, C4H), 8.38 (1H, t, ³J 8.6, C3H), 8.35 (1H, ddd, ³J 9.5, 6.9, ⁴J 1.6, C6H), 8.07-8.09 (1H, m, C4'H), 8.02-8.04 (1H, m, C5'H), 7.65-7.68 (2H, m, C8H, C3'H), 7.59 (1H, ddd, ³J 8.7, 6.7, ⁴J 0.6, C7H), 7.54 (1H, ddd, ³J 8.7, 6.9, ⁴J 1.2, C6'H), 7.31 (1H, ddd, ³J 8.7, 6.9, ³J 1.2, C7'H), 7.27 (1H, dd, ³J 7.0, ⁴J 1.0, C2'H), 7.03 (1H, d, ³J 7.9, C2H), 6.96 (1H, dd, ³J 8.5, ⁴J 0.9, C8'H), 5.27 (3H, s, NCH₃), 3.22 (3H, s, OCH₃); ¹³C NMR (125 MHz, CDCl₃):δ=159.9 (C9), 159.1 (C1), 142.6 (C4a), 141.2 (C10a), 141.1 (C3), 139.2 (C6), 135.3 (C1'), 132.8 (C4'a), 131.4 (C8'a), 130.4 (C8), 129.0 (C4'), 128.5 (C5'), 127.5 (C7), 127.2 (C7'), 126.9 (C8a), 126.6 (C6), 125.3 (C2'), 125.1 (C8'), 125.0 (C3), 120.3 (C9a), 119.2 (C5), 111.1 (C4), 106.7 (C2), 56.7 (OCH₃), 41.7 (NCH₃); ESI- MS: m/z calcd. for $C_{25}H_{20}NO^+$ 350.1539 found 350.1544 [M⁻]. Luminescence spectroscopy (in MeCN): $\lambda_{abs1}$: 474 nm; $\lambda_{abs2}$: 408 nm; $\lambda_{abs3}$: 282 nm; $\varepsilon_{abs1}$: 4.7·10³ L·cm·mol⁻¹; $\varepsilon_{abs2}$: 1.1·10⁴ L·cm·mol⁻¹; $E_{abs3}$: 5.8·10⁴ L cm mol⁻¹; $\lambda_{em}$(exc 464): 605 nm; Stokes shift: 131 nm; $E_{0,0}$: 2.33 eV; $<\tau_F>$: 13 ns; Cyclic voltammetry (vs SCE): $E_{1/2}(P^*/P)$: +1.75 V, $E_{1/2}(P/P^-)$: −0.58 V.

Example 37

6-(Dimethylamino)-9-mesityl-1-methoxy-10-phenylacridinium bromide salt

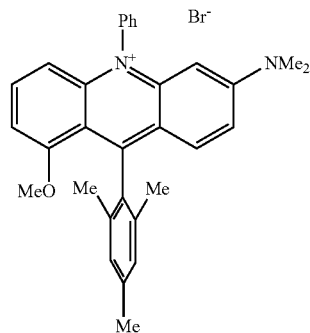 [SMILES: [Br-] ; COc1cccc2c1c(-c1c(C)cc(C)cc1C)c1ccc(N(C)C)cc1[n+]2-c1ccccc1]

The compound was prepared according to the general procedure I, described in Example 3, using 4-bromo-N³-(3-methoxyphenyl)-N¹,N¹-dimethyl-N³-phenylbenzene-1,3-diamine (63.6 mg, 160 μmol) in n-hexane:Et₂O (10:1, 2.2 mL) and general procedure III, described in Example 5, using methyl 2,4,6-trimethylbenzoate (17.8 mg, 100 μmol) and was stirred 12 h at RT. Purification gave a brown red solid (40.1 mg, 76%, decomp. at 106° C.): R_f 0.18 (CH₂Cl₂: MeOH 10:1); $v_{max}$ (neat): 3380 w, 2934 w, 2360 w, 1623 m, 1597 s, 1502 s, 1473 s, 1431 s, 1383 m, 1343 m, 1255 s, 1211 m, 1094 s, 916 w, 813 m, 794 m, 687 m, 647 w; ¹H NMR (500 MHz, CDCl₃): δ=7.89-7.92 (2H, m, C3"H, C5"H), 7.81-7.84 (1H, m, C4"H), 7.74 (1H, dd, ³J 8.9, 8.2, C3H), 7.48-7.50 (2H, m, C2"H, C6"H), 7.42 (1H, d, ³J 9.9, C8H), 7.25 (1H, dd, ³J10, ⁴J2.4, C7H), 7.02 (2H, d, ⁴J0.5, C3'H, C5'H), 6.89 (1H, d, ³J7.8, C2H), 6.70 (1H, dd, ³J8.7, ⁴J0.9, C4H), 5.80 (1H, d, ⁴J2.4, C5H), 3.57 (3H, s, OCH₃), 3.18 (6H, br, N(CH₃)₂), 2.43 (3H, s, CH₃), 1.85 (6H, s, 2 x CH₃); ¹³C NMR (125 MHz, CDCl₃): δ=159.7 (C1), 157.2 (C9), 156.3 (C6), 144.8 (C10a), 142.4 (C4a), 137.9 (C4'), 137.8 (C1"), 136.9 (C3), 134.3 (C1'), 133.7 (C2', C6'), 132.0 (C3", C5"), 131.3 (C4"), 131.1 (C8), 128.0 (C3', C5'), 128.0 (C2", C6"), 120.3 (C8a), 118.4 (C7), 114.8 (C9a), 110.3 (C4), 105.4 (C2), 93.6 (C5), 56.8 (OCH₃), 41.0 (N(CH₃)₂), 21.2 (CH₃), 20.2 (2×CH₃); ESI-MS: m/z calcd. for $C_{31}H_{31}N_2O^+$ 447.2431 found 447.2439 [M⁻]. Luminescence spectroscopy (in MeCN): $\lambda_{abs1}$: 513 nm; $\lambda_{abs2}$: 488 nm; $\lambda_{abs3}$: 433 nm; $\lambda_{abs4}$: 293 nm; $\varepsilon_{abs1}$: 1.1·10⁴ L cm mol⁻¹; $\varepsilon_{abs2}$: 1.0·10⁴ L cm mol⁻¹; $\varepsilon_{abs3}$: 1.6·10⁴ L cm mol⁻¹; $\varepsilon_{abs4}$: 3.4·10⁴ L cm mol⁻¹; $\lambda_{em}$(exc 503): 566 nm; Stokes shift: 53 nm; $E_{0,0}$: 2.31 eV; Cyclic voltammetry (vs SCE): $E_{1/2}(P^*/P^-)$: +1.42 V, $E_{1/2}(P/P^-)$: −0.89 V.

Example 38

6-(Dimethylamino)-9-(2,6-dimethylphenyl)-1-methoxy-10-phenylacridinium bromide

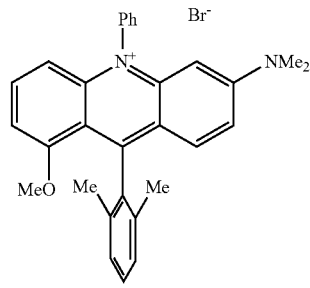 [SMILES: [Br-] ; COc1cccc2c1c(-c1c(C)cccc1C)c1ccc(N(C)C)cc1[n+]2-c1ccccc1]

The compound was prepared according to the general procedure I, described in Example 3, using 4-bromo-N³-(3-methoxyphenyl)-N¹,N¹-dimethyl-N³-phenylbenzene-1,3-diamine (63.6 mg, 160 μmol) in n-hexane:Et₂O (10:1, 2.2 mL) and general procedure III, described in Example 5, using methyl 2,6-dimethylbenzoate (16.4 mg, 100 μmol) and was stirred 12 h at RT. Purification gave a brown red solid (40.2 mg, 78%, decomp. at 121° C.): R$_f$ 0.18 (CH₂Cl₂: MeOH 10:1); ν$_{max}$ (neat): 3379 w, 2925 w, 2360 w, 1623 m, 1597 s, 1503 s, 1473 s, 1431 s, 1383 m, 1343 m, 1255 s, 1211 m, 1097 s, 1002 w, 966 w, 915 w, 764 m, 702 w, 685 w; ¹H NMR (500 MHz, CDCl₃): δ=7.90-7.93 (2H, m, C3"H, C5"H), 7.83-7.85 (1H, m, C4"H), 7.74 (1H, dd, ³J8.9, 8.2, C3H), 7.50-7.52 (2H, m, C2"H, C6"H), 7.39 (1H, d, ³J9.7, C8H), 7.33 (1H, t, ³J7.6, C4'H), 7.26 (1H, dd, ³J9.9, ⁴J2.4, C7H), 7.21 (2H, d, ³J7.6, C3'H, C5'H), 6.88 (1H, d, ³J 7.9, C2H), 6.72 (1H, ³J 9.0, ⁴J 0.7, C4H), 5.82 (1H, d, ³J 2.4, C5H), 3.54 (3H, s, OCH₃), 3.20 (6H, br, N(CH₃)₂), 1.90 (6H, s, 2×CH₃); ¹³C NMR (125 MHz, CDCl₃): δ=159.6 (C1), 156.6 (C9), 156.3 (C6), 144.9 (C10a), 142.5 (C4a), 137.8 (C1"), 137.3 (C1'), 136.9 (C3), 133.9 (C2', C6'), 132.1 (C3", C5"), 131.3 (C4"), 130.9 (C8), 128.4 (C4'), 128.0 (C2", C6"), 127.3 (C3', C5'), 120.1 (C8a), 118.5 (C7), 114.5 (C9a), 110.4 (C4), 105.4 (C2), 93.7 (C5), 56.8 (OCH₃), 41.1 (N(CH₃)₂), 20.3 (2×CH₃); ESI-MS: m/z calcd. for C₃₀H₂₉N₂O⁺ 433.2274 found 433.2282 [M⁺]. Luminescence spectroscopy (in MeCN): λ$_{abs1}$: 514 nm; abs2: 489 nm; λ$_{abs3}$: 433 nm; λ$_{abs4}$: 293 nm; ε$_{abs1}$: 1.1·10⁴ L cm mol⁻¹; ε$_{abs2}$: 1.1·10⁴ L cm mol⁻¹; ε$_{abs3}$: 1.6·10⁴ L cm mol⁻¹; ε$_{abs4}$: 3.5·10⁴ L cm mol⁻¹ λ$_{em}$(exc 504): 565 nm; Stokes shift: 51 nm; E$_{0,0}$: 2.30 eV; Cyclic voltammetry (vs SCE): E$_{1/2}$(P*/P⁻): +1.40 V, E$_{1/2}$(P/P⁻): -0.90 V.

Example 39

(±)-6-(Dimethylamino)-1-methoxy-9-(naphthalen-1-yl)-10-phenylacridinium bromide salt

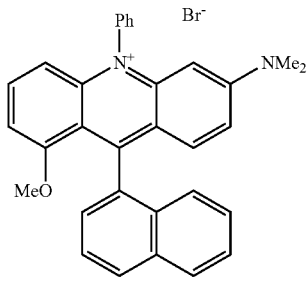 [SMILES: [Br-] ; COc1cccc2c1c(-c1cccc3ccccc13)c1ccc(N(C)C)cc1[n+]2-c1ccccc1]

The compound was prepared according to the general procedure I, described in Example 3, using 4-bromo-N³-(3-methoxyphenyl)-N¹,N¹-dimethyl-N³-phenylbenzene-1,3-diamine (63.6 mg, 160 gmol) in n-hexane:Et₂O (10:1, 2.2 mL) and general procedure III, described in Example 5, using methyl 1-naphthoate (18.6 mg, 100 gmol) and was stirred 12 h at RT. Purification gave a brown red solid (50.6 mg, 95%, decomp. at 154° C.): R$_f$ 0.18 (CH₂Cl₂:MeOH 10:1); ν$_{max}$ (neat): 3385 w, 2934 w, 2361 w, 1624 m, 1597 s, 1503 s, 1473 s, 1430 s, 1385 m, 1361 m, 1254 s, 1211 s, 1178 m, 1097 s, 1029 w, 922 w, 785 w, 703 m, 690 m; NMR (500 MHz, CDCl₃): δ=8.03-8.05 (1H, m, C4'H), 8.01-8.02 (1H, m, C5"H), 7.91-7.96 (2H, m, C3"H, C5"H), 7.82-7.85 (1H, m, C4"H), 7.72 (1H, dd, ³J 8.9, 8.2, C3H), 7.65 (1H, dd, ³J 7.7, 7.0, C3'H), 7.59-7.61 (1H, m, C2"H), 7.53-7.56 (2H, m, C6'H, C6"H), 7.38 (1H, ddd, ³J 8.5, 7.7, ⁴J 1.1, C7'H), 7.35 (1H, dd, ³J 6.8, ⁴J 1.0, C2'H), 7.35 (1H, d, ³J 10, C8H), 7.25 (1H, dd, ³ J8.2, ⁴J 0.6, C8'H), 7.11 (1H, dd, ³J 10, ⁴J 2.4, C7H), 6.77 (1H, d, ³J 8.0, C2H), 6.74 (1H, dd, ³J 8.8, ⁴J 0.5, C4H), 5.85 (1H, d, ³J 2.4, C5H), 3.16 (6H, br, N(CH₃)₂), 3.13 (3H, s, OCH₃); ¹³C NMR (125 MHz, CDCl₃): δ=159.2 (C1), 156.3 (C6), 155.4 (C9), 145.0 (C10a), 142.3 (C4a), 137.9 (C1"), 136.9 (C3), 135.6 (C1'), 132.9 (C4'a), 132.2 (C8), 132.2 (C3"), 132.1 (C5"), 131.6 (C8'a), 131.3 (C4"), 128.7 (C4'), 128.5 (C5'), 128.0 (C2"), 128.0 (C6"), 127.0 (C7'), 126.4 (C6'), 125.3 (C2'), 125.1 (C8'), 125.1 (C3'), 121.6 (C8a), 117.9 (C7), 115.6 (C9a), 110.3 (C4), 105.8 (C2), 93.5 (C5), 56.4 (OCH₃), 41.0 (N(CH₃)₂); ESI-MS: m/z calcd. for C₃₂H₂₇N₂O⁺ 455.2118 found 455.2122 [M⁺]. Luminescence spectroscopy (in MeCN): λ$_{abs1}$: 516 nm; λ$_{abs2}$: 491 nm; λ$_{abs3}$: 433 nm; λ$_{abs4}$: 294 nm; ε$_{abs1}$: 1.1·10⁴ L cm mol⁻¹; ε$_{abs2}$: 1.1·10⁴ L cm mol⁻¹; ε$_{abs3}$: 1.6·10⁴ L cm mol⁻¹; ε$_{abs4}$: 4.0·10⁴ L cm mol⁻¹; λ$_{em}$(exc 506): 568 nm; Stokes shift: 52 nm; E$_{0,0}$: 2.29 eV; Cyclic voltammetry (vs SCE): E$_{1/2}$(P*/P⁻): +1.42 V, E$_{1/2}$(P/P⁻): -0.87 V.

Example 40

7-(Dimethylamino)-9-mesityl-1-methoxy-10-phenylacridinium bromide salt

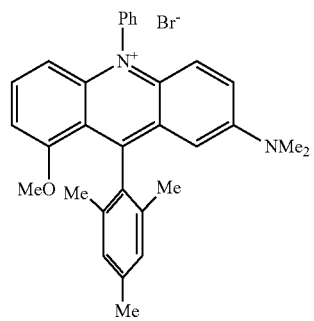 [SMILES: COc1cccc2c1c(-c1c(C)cc(C)cc1C)c1cc(N(C)C)ccc1[n+]2-c1ccccc1 ; [Br-]]

The compound was prepared according to the general procedure I, described in Example 3, using 2-bromo-N¹-(3-methoxyphenyl)-N⁴,N⁴-dimethyl-N¹-phenylbenzene-1,4-diamine (63.6 mg, 160 μmol) in n-hexane:Et₂O (10:1, 2.2 mL) and general procedure III, described in Example 5, using methyl 2,4,6-trimethylbenzoate (17.8 mg, 100 μmol) and was stirred 12 h at RT. Purification gave a brown red solid (41.2 mg, 78%, decomp. at 143° C.): R$_f$ 0.24 (CH₂Cl₂: MeOH 10:1); ν$_{max}$ (neat): 3380 w, 2919 w, 2361 w, 1617 s, 1573 m, 1518 m, 1490 m, 1455 m, 1359 s, 1267 s, 1209 s, 1088 s, 979 w, 924 w, 816 m, 764 s, 726 m, 702 m, 635 w; ¹H NMR (500 MHz, CDCl₃): δ=7.92-7.95 (2H, m, C3"H, C5"H), 7.84-7.90 (3H, m, C3H, C6H, C4"H), 7.57-7.59 (2H, m, C2"H, C6"H), 7.37 (1H, d,³J9.8, C5ll), 7.06 (2H, d, ⁴J 0.5, C3'H, C5'H), 7.01 (1H, d, ³J7.9, C2H), 6.93 (1H, dd, ³J9.1, ⁴J0.5, C4H), 6.44 (1H, d, ³J2.9, C8H), 3.63 (3H, s, OCH₃), 2.99 (6H, s, N(CH₃)₂), 2.45 (3H, s, CH₃), 1.83 (6H, s, 2×CH₃); ¹³C NMR (125 MHz, CDCl₃): δ=158.5 (C1), 157.3 (C9), 148.8 (C7), 140.0 (C4a), 138.0 (C4'), 137.5 (C1"), 137.1 (C3), 135.5 (C10a), 134.6 (C1'), 133.3 (C2', C6'), 131.8 (C4"), 131.8 (C3", C5"), 129.2 (C6), 128.3 (C3', C5'), 128.2 (C8a), 127.7 (C2", C6"), 120.2 (C5), 119.7 (C9a), 111.4 (C4), 105.8 (C2), 101.5 (C8), 57.0 (OCH₃), 40.2 (N(CH₃)₂), 21.3 (CH₃), 20.1 (2×CH₃); ESI- MS: m/z calcd. for C₃₁H₃₁N₂O⁺ 447.2431 found 447.2439 [M⁺].

Luminescence spectroscopy (in MeCN): $\lambda_{abs1}$: 583 nm; $\lambda_{abs2}$: 412 nm; $\lambda_{abs3}$: 318 nm; $\varepsilon_{abs1}$: 5.6·10$^3$ L cm mol$^{-1}$; $\varepsilon_{abs2}$: 2.5.10$^3$ L cm mol$^{-1}$; $\varepsilon_{abs3}$: 3.1.10$^4$ L cm mol$^{-1}$; $\lambda_{em}$(exc 573): 706 nm; Stokes shift: 123 nm; $\varepsilon_{0,0}$: 1.92 eV; Cyclic voltammetry (vs SCE): $E_{1/2}(P^*/P^-)$: +1.22 V, $E_{1/2}(P/P^-)$: −0.68 V.

Example 41

(±)-7-(Dimethylamino)-1-methoxy-9-(naphthalen-1-yl)-10-phenylacridinium bromide salt

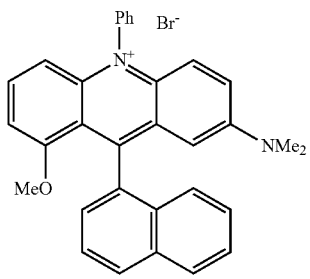 [SMILES: COc1cccc2c1c(-c1cccc3ccccc13)c1cc(N(C)C)ccc1[n+]2-c1ccccc1 ; [Br-]]

The compound was prepared according to the general procedure I, described in Example 3, using 2-bromo-N$^1$-(3-methoxyphenyl)-N$^4$,N$^4$-dimethyl-N$^1$-phenylbenzene-1,4-diamine (63.6 mg, 160 µmol) in n-hexane:Et$_2$O (10:1, 2.2 mL) and general procedure III, described in Example 5, using methyl 1-naphthoate (18.6 mg, 100 µmol) and was stirred 12 h at RT. Purification gave a brown red solid (50.1 mg, 94%, decomp. at 113° C.): R$_f$ 0.20 (CH$_2$Cl$_2$:MeOH 10:1); v. (neat): 3365 w, 3002 w, 2934 w, 2361 w, 1619 m, 1573 m, 1518 m, 1490 m, 1456 m, 1361 s, 1267 s, 1207 s, 1169 m, 1089 m, 976 w, 924 w, 782 s, 692 m; $^1$H NMR (500 MHz, CDCl$_3$): δ=8.05-8.07 (1H, m, C4'H), 8.02-8.03 (1H, m, C5'H), 7.91-7.98 (2H, m, C3"H, C5"H), 7.88-7.90 (1H, m, C4"H), 7.82-7.85 (2H, m, C3H, C6H), 7.66-7.73 (3H, m, C3'H, C2"H, C6"H), 7.53-7.56 (1H, m, C6'H), 7.42 (1H, dd, $^3$J 7.0, $^4$J 0.9, C2'H), 7.39 (1H, d, $^3$J 10, C5H), 7.37 (1H, $^3$J 8.2, 7.5, $^4$J 1.3, C7'H), 7.23-7.25 (1H, m, C8'H), 6.97 (1H, d, $^3$J 9.5, C4H), 6.89 (1H, d, $^3$J 8.0, C2H), 6.33 (1H, d, $^4$J 2.9, C8H), 3.21 (3H, s, OCH$_3$), 2.81 (6H, s, N(CH$_3$)$_2$); $^{13}$C NMR (125 MHz, CDCl$_3$): δ=158.1 (C1), 155.1 (C9), 148.3 (C7), 140.1 (C4a), 137.6 (C1"), 137.0 (C3), 136.1 (C1'), 135.8 (C10a), 132.9 (C4'a), 131.8 (C3", C5"), 131.7 (C4"), 131.0 (C8'a), 129.5 (C8a), 129.2 (C6), 128.7 (C4'), 128.5 (C5'), 127.8 (C2"), 127.8 (C6"), 127.0 (C7'), 126.4 (C6), 125.3 (C3'), 125.1 (C8'), 125.0 (C2), 120.4 (C9a), 120.0 (C5), 111.4 (C4), 106.3 (C2), 103.4 (C8), 56.6 (OCH$_3$), 40.0 (N(CH$_3$)$_2$); ESI-MS: m/z calcd. for C$_{32}$H$_{27}$N$_2$O$^+$ 455.2118 found 455.2120 [M$^+$]. Luminescence spectroscopy (in MeCN): $\lambda_{abs1}$: 590 nm; $\lambda_{abs2}$: 419 nm; $\lambda_{abs3}$: 317 nm; $\varepsilon_{abs1}$: 5.8·10$^3$ L cm mol$^{-1}$; $\varepsilon_{abs2}$: 2.7·10$^3$ L cm mol$^{-1}$; $\varepsilon_{abs3}$: 3.2.10$^4$ L cm mol$^{-1}$; $\lambda_{em}$(exc 582): 717 nm; Stokes shift: 137 nm; $E_{0,0}$: 1.90 eV; Cyclic voltammetry (vs SCE): $E_{1/2}(P^*P^-)$: +1.22 V, $E_{1/2}(P/P^-)$: −0.68 V.

Example 42

3,7-Bis(dimethylamino)-9-mesityl-1-methoxy-10-phenylacridinium bromide salt

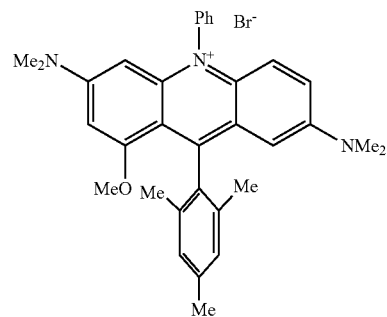 [SMILES: COc1cc(N(C)C)cc2c1c(-c1c(C)cc(C)cc1C)c1cc(N(C)C)ccc1[n+]2-c1ccccc1 ; [Br-]]

The compound is prepared according to the general procedure I and III described in Example 3 and 5 using N$^1$-(2-bromo-4-(dimethylamino)phenyl)-5-methoxy-N$^3$,N$^3$-dimethyl-N$^1$-phenylbenzene-1,3-diamine (70.5 mg, 160 $_K$mol) and e.g. methyl 2,4,6-trimethylbenzoate (17.8 mg, 100 µmol).

Example 43

3,6-Bis(dimethylamino)-9-mesityl-1-methoxy-10-phenylacridinium bromide salt

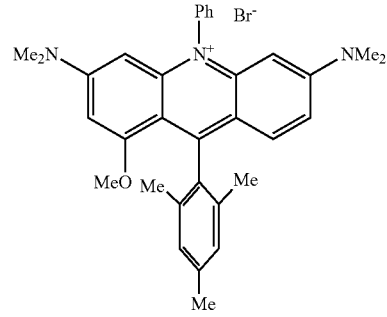 [SMILES: COc1cc(N(C)C)cc2c1c(-c1c(C)cc(C)cc1C)c1ccc(N(C)C)cc1[n+]2-c1ccccc1 ; [Br-]]

The compound is prepared according to the general procedure I and III described in Example 3 and 5 using 4-bromo-N$^3$-(3-(dimethylamino)-5-methoxyphenyl)-N$^1$,N$^1$-dimethyl-N$^3$-phenylbenzene-1,3-diamine (70.5 mg, 160 $_K$mol) and e.g. methyl 2,4,6-trimethylbenzoate (17.8 mg, 100 µmol).

Example 44

Photocatalyzed Oxidative [3+2] Cycloaddition

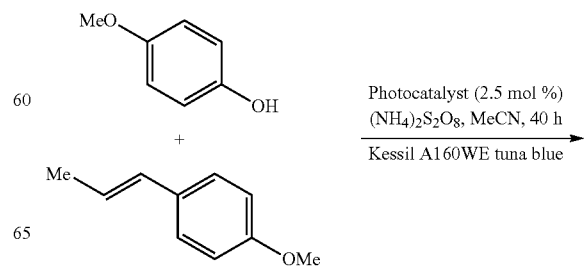

-continued

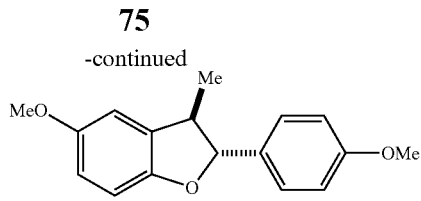

Prepared according to a modified literature procedure (T. P. Yoon, et al., *Angew. Chem. Int. Ed.* 2014, 53, 11056). To a mixture of trans-anethol (19.3 mg, 130 µmol), ammonium peroxydisulfate (45.6 mg, 200 µmol) photocatalyst (2.5 mol %, see table below,) in MeCN (3.0 mL) was added p-hydroxyanisole (12.4 mg, 100 µmol) and was degassed by a stream of argon for 10 min. The reaction was performed under argon atmosphere with the light on for 40 h. The reaction mixture was filtered over silica gel and rinsed with EtOAc. The filtrate was concentrated in vacuo, dissolved in $CH_2Cl_2$, mixed with silica gel (1 g), concentrated in vacuo and the residue was column chromatographed over silica gel with cyclohexane:EtOAc 50:1-50:3 afforded cycloadducts in the yields indicated in the table below.

(±)-5-Methoxy-2-(4-methoxyphenyl)-3-methyl-2,3-dihydrobenzofuran

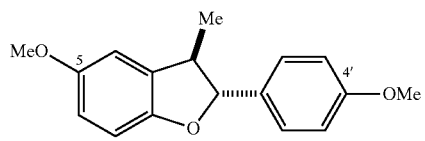 [SMILES: COc1ccc([C@@H]2Oc3ccc(OC)cc3[C@H]2C)cc1]

$R_f$ 0.29 (n hexane:EtOAc 5:1); $^1$H NMR (500 MHz, CDCl$_3$): δ=7.35-7.37 (2H, m, C2'H, C6'H), 6.90-6.92 (2H, m, C3'H, C5'H), 6.72-6.76 (1H, m, C4H), 6.69-6.72 (2H, m, C6H, C7H), 5.08 (1H, d, $^3$J 9.0, C1H), 3.82 (3H, s, C4'OCH$_3$), 3.78 (3H, s, C5OCH$_3$), 3.38-3.44 (1H, m, C2H), 1.38 (3H, d, $^3$J6.8, CH$_3$); $^{13}$C NMR (125 MHz, CDCl$_3$): δ=159.6 (C4), 154.4 (C5), 153.3 (C8), 133.1 (C3), 132.7 (C1'), 127.7 (C2', C6'), 114.0 (C3', C5'), 112.9 (C6), 110.0 (C7), 109.4 (C4), 92.6 (C1), 56.1 (C4'OCH$_3$), 55.3 (C5OCH$_3$), 45.7 (C2), 17.6 (CH$_3$); Analytical data is in agreement with literature (T. P. Yoon, et al., *Angew. Chem. Int. Ed.* 2014, 53, 11056).

| Photocatalyst | Product Yield |
| --- | --- |
| Ex34 (1.18 mg, 2.5 mol %) | 55% (14.9 mg) |
| Ex37 (1.32 mg, 2.5 mol %) | 77% (20.8 mg) |
| Ex38 (1.28 mg, 2.5 mol %) | 57% (15.5 mg) |
| (±)-Ex39 (1.34 µg, 2.5 mol %) | 61% (16.4 mg) |
| MesMeAcr (998 µg, 2.5 mol %)[a] | 45% (12.2 mg) |

[a]S. Fukuzumi, et al., *J. Am. Chem. Soc.* 2004, 126, 1600.

Example 45

Decarboxylative Fluorination

General Procedure:

Prepared according to a modified literature procedure (D. W. C. MacMillan, et al. *J. Am. Chem. Soc.* 2015, 137, 5654). To a mixture of 1-chloromethyl-4-fluoro-1,4-diazonia-bicyclo[2.2.2]octane bis(tetrafluoroborate) (106 mg, 300 µmol), sodium hydrogen phosphate (28.4 mg, 200 µmol) and photocatalyst (2.5 mol %, see table below) in MeCN:H$_2$O (1:1, 2.0 mL) was added carboxylic acid (100 µmol) and was degassed by a stream of argon for 10 min. The reaction was performed under argon atmosphere with the light on for the time specified below. The reaction mixture was twice treated with EtOAc (5 mL) and concentrated in vacuo. Purification (specified below) afforded fluorinated products in the yields indicated in the tables.

(4-Fluoropiperidin-1-yl)(phenyl)methanone

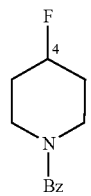

The compound was prepared according to the general procedure, using 1-benzoylpiperidine-4-carboxylic acid (23.3 mg, 100 µmol) and 6 h of irradiation. The residue was dissolved in $CH_2Cl_2$, mixed with silica gel (1 g), concentrated in vacuo and the residue was column chromatographed over silica gel with eluent pentane:Et$_2$O 2:1 to 1:2 to afford the product as a colorless oil: $R_f$ 0.21 (pentane:Et$_2$O 1:2); $^1$H NMR (500 MHz, CDCl$_3$): δ=7.39-7.42 (5H, m, C$_6$H$_5$), 4.84-4.97 (1H, m, C4H), 3.64-4.02 (2H, m, C2H$_2$), 3.43-3.56 (2H, m, C6H$_2$), 1.72-1.95 (4H, m, C3H$_2$, C5H$_2$); $^{13}$C NMR (125 MHz, CDCl$_3$): δ=170.5 (C=O), 135.9 (C1'), 129.7 (C4'), 128.6 (C3', C5'), 126.8 (C2', C6'), 87.7 ($^1J_{CF}$ 171, C—F), 43.6 (C6), 38.1 (C2), 31.8 (C3), 31.0 (C5); $^{19}$F NMR (377 MHz, CDCl$_3$): -183.2; Analytical data is in agreement with literature (D. W. C. MacMillan, et al. *J. Am. Chem. Soc.* 2015, 137, 5654).

| Photocatalyst | Product Yield |
| --- | --- |
| Ex33 (1.21 mg, 2.5 mol %) | 66% (13.6 mg) |
| Ex34 (1.18 mg, 2.5 mol %) | 58% (12.0 mg) |
| Ex37 (1.32 mg, 2.5 mol %) | 75% (15.6 mg) |
| Ex38 (1.28 mg, 2.5 mol %) | 78% (16.1 mg) |
| Ex40 (1.32 mg, 2.5 mol %) | 56% (11.5 mg) |
| Mes-1,3,6,8-(MeO)$_4$—PhAcr (1.45 mg, 2.5 mol %)[a] | 52% (10.8 mg) |
| MesMeAcr (998 µg, 2.5 mol %)[b] | 47% (9.79 mg) |

[a]D. DiRocco, et al., *J. Org. Chem.* 2016, 81, 7244;
[b]S. Fukuzumi, et al., *J. Am. Chem. Soc.* 2004, 126, 1600.

(±)-2-(1-Fluro-2,2-dimethylpropyl)isoindoline-1,3-dione

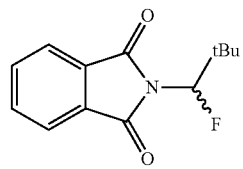 [SMILES: CC(C)(C)C(F)N1C(=O)c2ccccc2C1=O]

The compound was prepared according to the general procedure D, using (S)-2-(1,3-dioxoisoindolin-2-yl)-3,3-dimethylbutanoic acid (26.1 mg, 100 µmol) and 3 h of irradiation.

The residue was filtered over a plug of silica gel with CH$_2$Cl$_2$ affording the product as a white solid: R$_f$ 0.38 (pentane:CH$_2$Cl$_2$ 1:1); $^1$H NMR (500 MHz, CDCl$_3$): δ=7.89-7.90 (2H, m, C5H, C8H), 7.76-7.79 (2H, m, C6H, C7H), 5.91 (1H, d, J$_{HF}$ 44, CHF), 1.12 (9H, d, $^3$J1.1, C(CH$_3$)$_3$); $^{13}$C NMR (125 MHz, CDCl$_3$): δ=167.0 (C1, C3), 134.5 (C6, C7), 131.6 (C4, C9), 123.7 (C5, C8), 98.4 ($^1$J$_{CF}$ 211, C—F), 37.2 ($^2$J$_{CF}$ 23.4 ,C(CH$_3$)$_3$), 25.6 ($^3$J$_{CF}$ 3.4, C(CH$_3$)$_3$); $^{19}$F NMR (377 MHz, CDCl$_3$): 173.0; Analytical data is in agreement with literature (D. W. C. MacMillan, et al. *J. Am. Chem. Soc.* 2015, 137, 5654).

| Photocatalyst | Product Yield |
| --- | --- |
| Ex33 (1.21 mg, 2.5 mol %) | 90% (21.2 mg) |
| Ex34 (1.18 mg, 2.5 mol %) | 93% (21.9 mg) |
| Ex40 (1.32 mg, 2.5 mol %) | 89% (20.9 mg) |
| (S$_a$)-Ex35 (985 µg, 2.5 mol %)$^a$ | 94% (17.7 mg) |
| MesMeAcr (998 µg, 2.5 mol %)$^b$ | 90% (21.2 mg) |

$^a$80 µmol scale reaction;
$^b$S. Fukuzumi, et al., *J. Am. Chem. Soc.* 2004, 126, 1600.

Example 46

Photoredox-Catalyzed Deuteration

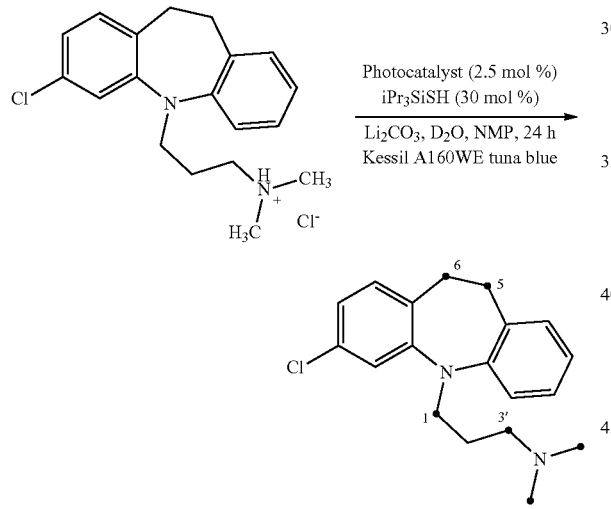

General Procedure:

Prepared according to a modified literature procedure (D. W. C. MacMillan, *Science* 2017, doi: 10.1126/science.aap9674). To a mixture of triisopropylsilanethiol (5.71 mg, 30 µmol), lithium carbonate (35.5 mg, 480 µmol), photocatalyst (2.5 mol %, see table below) and deuterium oxide (90.0 µL, 5.00 mmol) in N-methylpyrrolidinone (1.6 mL) was added clomipramine hydrochloride (33.7 mg, 100 µmol) and was degassed by a stream of argon for 20 min. The reaction was performed under argon atmosphere for 24 h with the light on. The reaction mixture was diluted in EtOAc (15 mL), washed with brine (20 mL) and extracted with EtOAc (3×15 mL). The combined organic layer was concentrated in vacuo and column chromatographed on silica gel with n-hexane:acetone:Et$_3$N, 96:2:2 to afford clomipramine free base. To afford the clomipramine HCl salt, the free base was dissolved in EtOAc, treated with HCl in dioxane (4 molL$^{-1}$, 250 µL), concentrated in vacuo, triturated from Et$_2$O and filtered: R$_f$ 0.34 (n hexane:acetone:Et$_3$N, 8:1:1); clomipramine free base (deuterated using 4 h as photocatalyst): $^1$H NMR (500 MHz, CD$_3$OD): δ=7.12-7.17 (3H, m), 7.09-7.10 (1H, m), 7.02-7.03 (1H, m), 6.95-6.98 (1H, m), 6.85-6.87 (1H, m), 3.73-3.76 (1.75H, m, 12% $^2$H, C1'H), 3.07-3.15 (4H, m, C5H, C6H), 2.33-2.40 (1.03H, m, 49% $^2$H, C3'H), 2.11-2.15 (4.16H, m, 30% $^2$H, N(CH$_3$)$_2$), 1.70-1.74 (2H, m, C2'H); Analytical data is in agreement with literature D. W. C. MacMillan, *Science* 2017, doi: 10.1126/science.aap9674).

The degree of deuteration and regioselectivity for each catalyst is listed below.

| Photocatalyst | average $^2$H/molecule$^a$ | Regioselectivity and degree of $^2$H incorporation for each position$^a$ | | | | |
| --- | --- | --- | --- | --- | --- | --- |
| | | C5 | C6 | C1' | C3' | NMe$_2$ |
| Ex37 (1.32 mg, 2.5 mol %) | 3.0 | — | — | 12% | 49% | 30% |
| Ex38 (1.28 mg, 2.5 mol %) | 1.3 | — | — | 6% | 22% | 13% |
| Ex40 (1.32 mg, 2.5 mol %) | 1.0 | — | — | — | 25% | 8% |
| Mes-1,3,6,8-(MeO)$_4$-PhAcr (1.45 mg, 2.5 mol %)$^b$ | <1.0 | — | — | — | 11% | 4% |

$^a$Determined by $^1$H-NMR of the free base;
$^b$D. DiRocco, et al., *J. Org. Chem.* 2016, 81, 7244.

Example 47

Photoredox/Ni Dual Catalysis C(sp$^3$)C(sp$^2$) Cross-Coupling

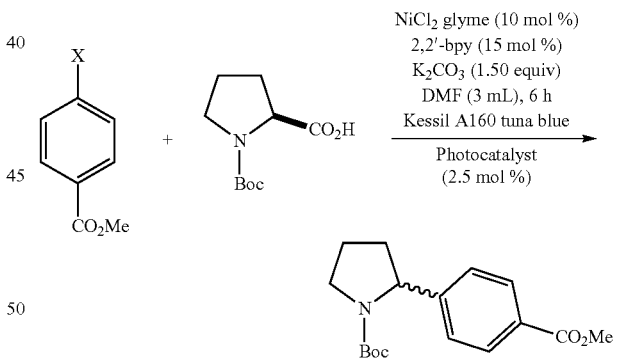

Prepared according to a modified literature procedure (D. W. C. MacMillan, et al., *Science* 2014, 345, 437). To a mixture of methyl 4-iodobenzoate (26.2 mg, 100 µmol), Boc-L-proline (32.3 mg, 150 µmol), NiCl$_2$ ethylene glycol dimethyl ether complex (2.20 mg, 1.00 mol%), 2,2'-bipyridine (2.34 mg, 1.5 mol %), K$_2$CO$_3$ (20.7 mg, 0.15 mmol) in dry N,N-dimethylformamide (3.0 mL) was added photocatalyst (2.5 mol %, specified below). The mixture was degassed by a stream of argon for 10 min. The reaction was performed under argon atmosphere for 6 h with the light on. The reaction mixture was diluted with water (20 mL) and extracted with EtOAc (3×15 mL) The combined organic layer was dried over Na$_2$SO$_4$ and concentrated in vacuo. Durene was used as internal standard (ISTD) to determine the yield by quantitative NMR analysis: $^1$H NMR (500 MHz, CDCl$_3$) rotameric mixture: δ=7.97-7.99 (2H, m, C3'H, C5'H), 7.23-7.25 (2H, m, C2'H, C6'H), 4.98 and 4.80 (1H, 2 br, C2H), 3.91 (1H, s, CO$_2$CH$_3$), 3.51-3.66 (2H, m, C5H$_2$), 2.30-2.38 (1H, m, C3H), 1.78-1.92 (3H, m, C3H, C4H$_2$), 1.46 (3H, s, C(CH$_3$)$_3$), 1.17 (6H, s, C(CH$_3$)$_3$); $^{13}$C NMR (125 MHz, CDCl$_3$) rotameric mixture, resonances of minor rotamer in parenthesis "{}": δ=167.0 (CO$_2$CH$_3$), 154.4 (CO$_2$tBu), 150.6 {149.6} (C1'), {129.8} 129.6 (C3', C5'), 128.5 (C4'), 125.5 (C2', C6'), 79.5 (C(CH$_3$)$_3$), 61.2 {60.7} (C2), 52.0 (CO$_2$CH$_3$), {47.4} 47.2 (C5), 36.0 {34.8} (C3), {28.5} 28.2 (C(CH$_3$)$_3$), {23.6} 23.3 (C4); Analytical data is in agreement with literature (D. W. C. MacMillan, et al., Science 2014, 345, 437).

| Photocatalyst | Product Yield[a] |
|---|---|
| Ex37 (1.32 mg, 2.5 mol %) | 57% |
| Ex38 (1.28 mg, 2.5 mol %) | 75% |
| Mes-1,3,6,8-(MeO)$_4$—PhAcr[b] (1.45 mg, 2.5 mol %)[c] | 10% |
| MesMeAcr (998 μg, 2.5 mol %)[c] | <1% |

[a]Durene was used as internal standard (ISTD) to determine the yield by quantitative NMR analysis;
[b]D. Di Rocco, et al., J. Org. Chem. 2016, 81, 7244;
[c]S. Fukuzumi, et al., J. Am. Chem. Soc. 2004, 126, 1600.

The invention claimed is:
1. A compound of formula (A)

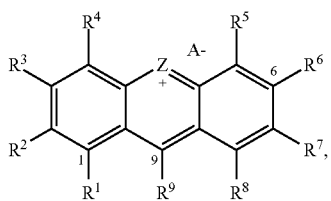

wherein
Z is NR$^{10}$ or O;
R$^1$ is selected from C1-C6-alkoxy, aryloxy, O-alkyl-aryl, C1-C6-hydroxyalkyl, O(CH$_2$)O(CH$_3$), O(CH$_2$) O(CH$_2$)$_2$OCH$_3$, NH$_2$, N(H)(C1-C6-alkyl), N(C1-C6-alkyl)$_2$, SH, F, CF$_3$, C1-C6-alkylthio, 4,4-dimethyl-4,5-dihydrooxazole, NHCOR$^{14}$, NHCO$_2$R$^{14}$, OCNR$_2$, CONHR$^{14}$, CON(R$^{14}$)$_2$, C=NR$^{14}$, CO$_2$H, [CO$_2^-$], CO$_2$R$^{14}$, SO$_3$R$^{14}$, SO$_3$H, SO$_2$NC(CH$_3$)$_3$, [SO$_3^-$], SO$_2$N(R$^{14}$)$_2$;
R$^2$ is selected from H, halogen, NO$_2$, CN, NH$_2$, N(H) (C1-C6-alkyl), N(C1-C6-alkyl)$_2$, OH, C1-C6-hydroxyalkyl, SH, C1-C6-alkylthio, C1-C12-alkyl, SO$_3$H, [SO$_3^-$], SO$_3$R$^{14}$, CO$_2$H, [CO$_2^-$], CO$_2$R$^{14}$;
R$^3$ is selected from H, halogen, NO$_2$, NH$_2$, N(H)(C1-C6-alkyl), N(C1-C6-alkyl)$_2$ and CN;
R$^4$ is selected from H, C1-C12-alkyl, halogen, NO$_2$, CN, NH$_2$, N(H)(C1-C6-alkyl), N(C1-C6-alkyl)$_2$, OH, C1-C6-alkoxy, aryloxy, O-alkyl-aryl, C1-C6-hydroxyalkyl, SH, C1-C6-alkylthio, SO$_3$H, [SO$_3^-$], SO$_3$R$^{14}$;
R$^5$ is selected from H, C1-C12-alkyl, halogen, NO$_2$, CN, NH$_2$, N(H)(C1-C6-alkyl), N(C1-C6-alkyl)$_2$, OH, C1-C6-hydroxyalkyl, SH, C1-C6-alkylthio, SO$_3$H, [SO$_3^-$], SO$_3$R$^{14}$;
R$^6$ is selected from H, halogen, NO$_2$, CN, NH$_2$, N(H) (C1-C6-alkyl), N(C1-C6-alkyl)$_2$, C1-C6-hydroxyalkyl;
R$^7$ is selected from H, halogen, NO$_2$, CN, NH$_2$, N(H) (C1-C6-alkyl), N(C1-C6-alkyl)$_2$, OH, C1-C6-alkoxy, C1-C6-hydroxyalkyl, SH, C1-C6-alkylthio, C1-C12-alkyl, SO$_3$H, [SO$_3^-$], SO$_3$R$^{14}$, CO$_2$H, [CO$_2^-$], CO$_2$R$^{14}$;
R$^8$ is selected from H, halogen, C1-C6-alkoxy, OH, C1-C6-hydroxyalkyl, O(CH$_2$)O(CH$_3$), O(CH$_2$) O(CH$_2$)$_2$OCH$_3$, NH$_2$, N(H)(C1-C6-alkyl), N(C1-C6-alkyl)$_2$, SH, F, CF$_3$, C1-C6-alkylthio, 4,4-dimethyl-4,5-dihydrooxazole, NHCOR$^{14}$, NHCO$_2$R$^{14}$, OCN(R$^{14}$)$_2$, CONHR$^{14}$, CON(R$^{14}$)$_2$, C=NR$^{14}$, CO$_2$H, [CO$_2^-$], NO$_2$, SO$_3$R$^{14}$, SO$_3$H, SO$_2$NC(CH$_3$)$_3$ and SO$_2$N(R$^{14}$)$_2$;
R$^9$ is selected from aryl, heteroaryl, C2-C6-alkenyl-aryl, C2-C12-alkenyl, C2-C12-alkynyl, C1-C12-alkyl, NH$_2$, N(H)(C1-C6-alkyl), N(C1-C6-alkyl), C1-C12-alkoxy, C1-C12-hydroxyalkyl, C1-C4-alkyl-CO$_2$H, C1-C4-alkyl-CO$_2$-C1-C6-alkyl, C(=O)H, C(=O)-C1-C6-alkyl and C1-C12-alkylthio; and wherein said aryl and heteroaryl are optionally substituted by one or more groups independently selected from halogen atoms, CN, N$_3$, C1-C6-alkyl, [SO$_3^-$], SO$_3$H, SO$_2$Cl, OH, C1-C6-alkoxy, CO$_2^-$, C(=O)OH and C1-C6-alkoxycarbonyl, C1-C12-hydroxyalkyl, C1-C12-thioalkyl;
R$^{10}$ is selected from aryl, heteroaryl, C1-C4-alkyl-aryl, C2-C6-alkenyl-aryl, C2-C12-alkenyl, C2-C12-alkynyl, C1-C12-alkyl, H, C1-C12-hydroxyalkyl, C(=O)H, C(=O)-C1-C6-alkyl, C1-C12-alkylthio, C1-C12-alkyl-CO$_2$H, C1-C12-alkyl-CO$_2$-C1-C12-alkyl, C1-C12-alkyl-CO$_2$-C1-C4-alkyl-aryl, O$^-$, S(=O)-C1-C6-alkyl, S(=O)aryl, S(=O)-heteroaryl, S(O$_2$)-C1-C6-alkyl, S(O$_2$)-aryl, S(O$_2$)-heteroaryl; wherein said aryl and heteroaryl are optionally substituted by one or more groups independently selected from halogen atoms, CN, N$_3$, C1-C6-alkyl, [SO$_3$]$^-$, SO$_3$H, SO$_2$Cl, OH, C1-C6-alkoxy, C(=O)OH and C1-C6-alkoxycarbonyl;
R$^{14}$ is selected from C1-C12-alkyl; and
A$^-$ is a suitable anion preferably selected from halide ions, [BF$_4$]$^{31}$, [PF$_6$]$^-$, [ClO$_4$]$^-$, [(C1-C5-alkyl)C(=O)O]$^-$, [aryl-CH$_2$-C(=O)O]$^-$, [aryl-C(=O)O]$^-$, [H$_2$PO$_4$]$^-$ [HSO$_4$]$^-$[SO$_4$]$^{2-}$, [(C1-C6-alkyl)SO$_3$]$^-$, [CF$_3$SO$_3$]$^-$, aryl-CH$_2$-SO$_3$]$^-$and [aryl-SO$_3$]$^-$, and wherein
when R$^3$ and R$^6$ are independently selected from NH$_2$, N(H)(C1-C6-alkyl), N(C1-C6-alkyl)$_2$, then R$^9$ is C2-C6-alkenyl-aryl, C2-C12-alkenyl, C2-C12-alkynyl, NH$_2$, N(H)(C1-C6-alkyl), N(C1-C6-alkyl)$_2$, C(=O)H, C(=O)-C1-C6-alkyl, C1-C12-alkylthio or aryl, wherein said aryl is substituted by one or more groups independently selected from C1-C6-alkyl, C1-C12-hydroxyalkyl, C1-C12-thioalkyl or N$_3$; and wherein
when Z is NR$^{10}$, R$^1$ and R$^8$ is OMe, then R$^9$ is not 2,6-dimethoxyphenyl or 4-( N(R$^{15}$)$_2$)-2,6-dimethoxyphenyl, wherein R$^{15}$ is CH$_3$, C$_2$H$_5$ or C$_6$H$_{13}$; and wherein
when Z is O, R$^1$ or R$^8$ is OMe, then R$^9$ is not 2,6-dimethoxyphenyl; and wherein
when Z is O, R$^1$ or R$^8$ is OMe, then R$^9$ is not phenyl.
2. The compound of claim 1, wherein said Z is NR$^{10}$.
3. The compound of claim 1, wherein said Z is O.
4. The compound according to claim 1, wherein R$^9$ is selected from phenyl, indenyl, indanyl, naphthyl, anthracenyl and tetracenyl, each independently optionally substituted by one, two or three groups independently selected from halogen atoms, CN, N$_3$, C1-C6-alkyl, [SO$_3$]$^-$, SO$_3$H, SO$_2$Cl, OH, C1-C6-alkoxy, CO$_2^-$, C(=O)OH, C1-C8-hydroxyalkyl, C1-C8-thioalkyl and C1-C6-alkoxycarbonyl.
5. The compound according to claim 1, wherein said R$^9$ is selected from phenyl and naphthyl, optionally substituted by one, two or three groups independently selected from F, Cl, CN, $CO_2^-$, $SO_3^-$, $CO_2H$, $SO_3H$, C1-C4-alkyl, C1-C4-alkoxy and C1-C4-thioalkyl.

6. The compound according to claim 1, wherein $R^2$, $R^3$, $R^4$, $R^5$ and $R^7$ are each H.

7. The compound according to claim 1, wherein $R^3$ and $R^6$ are independently selected from H, $NH_2$, N(H)(C1-C6-alkyl) or $N(C1-C6-alkyl)_2$.

8. The compound according to claim 1, wherein $R^1$ is selected from $NH_2$, N(H)(C1-C2-alkyl), $N(C1-C2-alkyl)_2$, C1-C4-alkoxy and F.

9. The compound according to claim 1, wherein $R^8$ is selected from H, $NH_2$, N(H)(C1-C2-alkyl), $N(C1-C2-alkyl)_2$, C1-C4-alkoxy and F.

10. The compound of claim 1, wherein said compound is selected from
1,8-Dimethoxy-10-methyl-9-phenylacridinium bromide;
9-(4-Fluorophenyl)-1,8-dimethoxy-10-methylacridinium bromide;
1,8-Dimethoxy-9-(4-methoxyphenyl)-10-methylacridinium bromide;
1,8-Dimethoxy-10-methyl-9-(naphthalen-1-yl)acridinium bromide;
1,8-Dimethoxy-9,10-diphenylacridinium bromide;
1,8-Dimethoxy-9,10-diphenylacridinium tetrafluoroborate;
1-Methoxy-10-methyl-9-phenylacridinium bromide;
6-(Dimethylamino)-1-methoxy-10-methyl-9-phenylacridinium bromide;
6-(Dimethylamino)-9-(4-fluorophenyl)-1-methoxyxanthylium bromide;
6-(Dimethylamino)-9-(4-fluorophenyl)-1-methoxyxanthylium chloride;
6-(Dimethylamino)-1-methoxy-9, 10-diphenylacridinium bromide;
9-Mesityl-1,8-dimethoxy-10-methylacridinium bromide;
9-Mesityl-1-methoxy-10-methylacridinium bromide;
6-(Dimethylamino)-9-mesityl-1-methoxy-10-methylacridinium bromide;
3,6-Bis(dimethylamino)-9-mesityl-1-methoxy-10-methylacridinium bromide;
3,6-Bis(dimethylamino)-9-mesityl-1,8-dimethoxy-10-methylacridinium bromide;
3-(Dimethylamino)-9-mesityl-1-methoxy-10-methylacridinium bromide;
3-(Dimethylamino)-1,8-dimethoxy-9,10-diphenylacridinium bromide;
(±)-3-(Dimethylamino)-1,8-dimethoxy-9-(naphthalen-1-yl)-10-phenylacridinium bromide;
(±)-3-(Dimethylamino)-9-(4-fluoronaphthalen-1-yl)-1,8-dimethoxy-10-phenylacridinium bromide;
3,6-Bis(dimethylamino)-1,8-dimethoxy-9,10-diphenylacridinium bromide 1-Methoxy-9,10-diphenylacridinium bromide;
9-Mesityl-1-methoxy-10-phenylacridinium bromide;
9-(2,6-Dimethylphenyl)-1-methoxy-10-phenylacridinium bromide;
(±)-1-Methoxy-9-(naphthalen-1-yl)-10-phenylacridinium bromide;
(±)-1-Methoxy-10-methyl-9-(naphthalen-1-yl)acridinium bromide;
6-(Dimethylamino)-9-mesityl-1-methoxy-10-phenylacridinium bromide;
6-(Dimethylamino)-9-(2,6-dimethylphenyl)-1-methoxy-10-phenylacridinium bromide;
(±)-6-(Dimethylamino)-1-methoxy-9-(naphthalen-1-yl)-10-phenylacridinium bromide;
7-(Dimethylamino)-9-mesityl-1-methoxy-10-phenylacridinium bromide;
(±)-7-(Dimethylamino)-1-methoxy-9-(naphthalen-1-yl)-10-phenylacridinium bromide;
3,7-Bis(dimethylamino)-9-mesityl-1-methoxy-10-phenylacridinium bromide; and
3,6-Bis(dimethylamino)-9-mesityl-1-methoxy-10-phenylacridinium bromide.

11. A compound of formula (A')

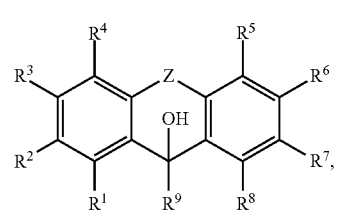

wherein
Z is $NR^{10}$;
$R^1$ is selected from C1-C6-alkoxy, aryloxy, O-alkyl-aryl, C1-C6-hydroxyalkyl, $O(CH_2)O(CH_3)$, $O(CH_2)O(CH_2)_2OCH_3$, $NH_2$, N(H)(C1-C6-alkyl), $N(C1-C6-alkyl)_2$, SH, F, $CF_3$, C1-C6-alkylthio, 4,4-dimethyl-4,5-dihydrooxazole, $NHCOR^{14}$, $NHCO_2R^{14}$, $OCNR_2$, $CONHR^{14}$, $CON(R^{14})_2$, $C=NR^{14}$, $CO_2H$, $[CO_2^-]$, $CO_2R^{14}$, $[SO_3^-]$, $SO_3R^{14}$, $SO_3H$, $SO_2NC(CH_3)_3$, $SO_2N(R^{14})_2$;
$R^2$ is selected from H, halogen, $NO_2$, CN, $NH_2$, N(H)(C1-C6-alkyl), $N(C1-C6-alkyl)_2$, OH, C1-C6-alkoxy, C1-C6-hydroxyalkyl, SH, C1-C6-alkylthio, $[SO_3^-]$, $SO_3H$, $SO_3R^{14}$, $CO_2H$, $[CO_2^-]$, $CO_2R^{14}$, C1-C12-alkyl;
$R^3$ is selected from H, halogen, $NO_2$, and CN;
$R^4$ is selected from H, C1-C12-alkyl, halogen, $NO_2$, CN, $NH_2$, N(H)(C1-C6-alkyl), $N(C1-C6-alkyl)_2$, OH, C1-C6-alkoxy, aryloxy, O-alkyl-aryl, C1-C6-hydroxyalkyl, SH, C1-C6-alkylthio, $SO_3R^{14}$, $[SO_3^-]$, $SO_3H$;
$R^5$ is selected from H, C1-C12-alkyl, halogen, $NO_2$, CN, $NH_2$, N(H)(C1-C6-alkyl), $N(C1-C6-alkyl)_2$, OH, C1-C6-hydroxyalkyl, SH, C1-C6-alkylthio, $SO_3R^{14}$, $SO_3H$, $[SO_3^-]$;
$R^6$ is selected from H, halogen, $NO_2$, CN, $NH_2$, N(H)(C1-C6-alkyl), $N(C1-C6-alkyl)_2$, C1-C6-hydroxyalkyl;
$R^7$ is selected from H, halogen, $NO_2$, CN, $NH_2$, N(H)(C1-C6-alkyl), $N(C1-C6-alkyl)_2$, OH, C1-C6-alkoxy and C1-C6-hydroxyalkyl, SH, C1-C6-alkylthio, C1-C12-alkyl, $SO_3R^{14}$, $SO_3H$, $[SO_3^-]$, $CO_2H$, $[CO_2^-]$, $CO_2R^{14}$;
$R^8$ is selected from H, halogen, C1-C6-alkoxy, OH, C1-C6-hydroxyalkyl, $O(CH_2)O(CH_3)$, $O(CH_2)O(CH_2)_2OCH_3$, $NH_2$, N(H)(C1-C6-alkyl), $N(C1-C6-alkyl)_2$, SH, F, $CF_3$, C1-C6-alkylthio, 4,4-dimethyl-4,5-dihydrooxazole, $NHCOR^{14}$, $NHCO_2R^{14}$, $OCNR_2$, $CONHR^{14}$, $CON(R^{14})_2$, $C=NR^{14}$, $CO_2H$, $[CO_2^-]$, $NO_2$, $SO_3R^{14}$, $SO_3H$, $SO_2NC(CH_3)_3$ and $SO_2N(R^{14})_2$;
$R^9$ is selected from aryl, heteroaryl, C2-C6-alkenyl-aryl, C2-C12-alkenyl, C2-C12-alkynyl, C1-C12-alkyl, $NH_2$, N(H)(C1-C6-alkyl), $N(C1-C6-alkyl)_2$, C1-C12-alkoxy, C1-C12-hydroxyalkyl, halogen, $N_3$, C1-C4-alkyl-$CO_2H$, C1-C4-alkyl-$CO_2$-C1-C6-alkyl, C(=O)H, C(=O)-C1-C6-alkyl and C1-C12-alkylthio; and
wherein said aryl and heteroaryl are optionally substituted by one or more groups independently selected from halogen atoms, CN, N$_3$, C1-C6-alkyl, [SO$_3$]$^-$, SO$_3$H, SO$_2$Cl, OH, C1-C6-alkoxy, C(=O)OH and C1-C6-alkoxycarbonyl, C1-C12-hydroxyalkyl, C1-C12-thioalkyl;

R$^{10}$ is selected from aryl, heteroaryl, C1-C4-alkyl-aryl, C2-C6-alkenyl-aryl, C2-C12-alkenyl, C2-C12-alkynyl, C1-C12-alkyl, H, C1-C12-hydroxyalkyl, C(=O)H, C(=O)-C1-C6-alkyl, C1-C12-alkylthio, C1-C12-alkyl-CO$_2$H; C1-C12-alkyl-CO$_2$-C1-C12-alkyl, C1-C12-alkyl-CO$_2$-C1-C4-alkyl-aryl, [O$^-$]; S(=O)-C1-C6-alkyl, S(=O)aryl, S(=O)-heteroaryl, S(O$_2$)-C1-C6-alkyl, S(O$_2$)-aryl, S(O$_2$)-heteroaryl; wherein said aryl and heteroaryl are optionally substituted by one or more groups independently selected from halogen atoms, CN, N$_3$, C1-C6-alkyl, [SO$_3$]$^-$, SO$_3$H, SO$_2$Cl, OH, C1-C6-alkoxy, C(=O)OH and C1-C6-alkoxycarbonyl;

R$^{14}$ is selected from C1-C12-alkyl.

12. The compound of claim 11, wherein said compound is 1,8-Dimethoxy-10-methyl-9-phenyl-9,10-dihydroacridin-9-ol.

13. A process for the preparation of the compound of formula (A) according to claim 1, comprising
(i) reacting a compound of formula (A''') with an organometallic reagent (R$^{12}$M) selected from aryl-MgX, C1-C6-alkyl-MgX, aryl-Li and C1-C6-alkyl-Li;

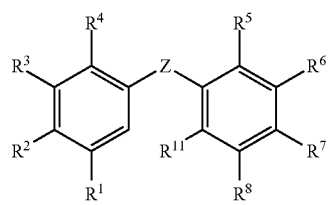

to form a compound of formula (A'')

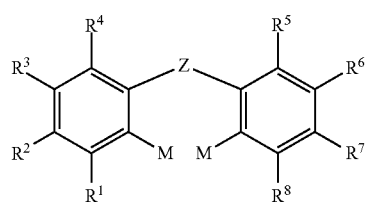

wherein when R$^{11}$ is H, then R$^8$ is selected from C1-C6-alkoxy, OH, C1-C6-hydroxyalkyl, O(CH$_2$)O(CH$_3$), O(CH$_2$)O(CH$_2$)$_2$OCH$_3$, NH$_2$, N(H)(C1-C6-alkyl), N(C1-C6-alkyl)$_2$, SH, F, CF$_3$, C1-C6-alkylthio, 4,4-dimethyl-4,5-dihydrooxazole, NHCOR$^{14}$, NHCO$_2$R$^{14}$, OCN(R$^{14}$)$_2$, CONHR$^{14}$, CON(R$^{14}$)$_2$, C=NR$^{14}$, CO$_2$H, [CO$_2^-$], SO$_3$R$^{14}$, SO$_3$H, [SO$_3^-$], SO$_2$NC(CH$_3$)$_3$, SO$_2$N(R$^{14}$)$_2$; and wherein when R$^{11}$ is halogen, then R$^8$ is selected from C1-C6-alkoxy, OH, C1-C6-hydroxyalkyl, O(CH$_2$)O(CH$_3$), O(CH$_2$)O(CH$_2$)$_2$OCH$_3$, NH$_2$, N(H)(C1-C6-alkyl), N(C1-C6-alkyl)$_2$, SH, F, CF$_3$, C1-C6-alkylthio, 4,4-dimethyl-4,5-dihydrooxazole, NHCOR$^{14}$, NHCO$_2$R$^{14}$, OCN(R$^{14}$)$_2$, CONHR$^{14}$, CON(R$^{14}$)$_2$, C=NR$^{14}$, CO$_2$H, [CO$_2^-$], SO$_3$R$^{14}$, SO$_3$H, [SO$_3^-$], SO$_2$NC(CH$_3$)$_3$, SO$_2$N(R$^{14}$)$_2$ and H; and wherein M is Li when the organometallic reagent (R$^{12}$M) is aryl-Li or C1-C6-alkyl-Li; and wherein M is MgX when the organometallic reagent (R$^{12}$M) is aryl-MgX or C1-C6-alkyl-MgX or MgX$_2$ or alkyl$_2$Mg or aryl$_2$Mg; and wherein X is a halogen; and wherein R$^1$ to R$^7$ and Z are defined in claim 1;

(ii) followed by reacting said compound of formula (A'') with a compound of formula (B) or (C)

R$^9$CO$_2$R$^{13}$ (B)

R$^9$COCl (C)

to form a compound of formula (A')

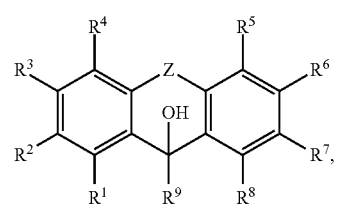

wherein R$^9$ is defined in claim 1; and
wherein R$^{13}$ is C1-C6-alkyl, C1-C6-alkanoyl; or
wherein R$^9$ and R$^{13}$ together with the atoms to which they are attached form a 4 to 6-membered ring optionally substituted by C2-C6-alkenyl-aryl, C2-C12-alkenyl, C2-C12-alkynyl, C1-C12-alkyl, NH$_2$, N(H)(C1-C6-alkyl), N(C1-C6-alkyl)$_2$, C1-C12-alkoxy, C1-C12-hydroxyalkyl, halogen, CN, N$_3$, C1-C4-alkyl-CO$_2$H, C1-C4-alkyl -CO$_2$-C1-C6-alkyl, C(=O)H, C(=O)-C1-C6-alkyl and C1-C12-alkylthio; or wherein R$^9$ and R$^{13}$ together with the atoms to which they are attached form a 4 to 6-membered ring fused to an aryl or heteroaryl, wherein said aryl or heteroaryl is optionally substituted by one or more groups independently selected from halogen atoms, CN, N$_3$, C1-C6-alkyl, [SO$_3$]$^-$, SO$_3$H, SO$_2$Cl, OH, C1-C6-alkoxy, C(=O)OH and C1-C6-alkoxycarbonyl, C1-C12-hydroxyalkyl, C1-C12-thioalkyl;

(iii) addition of a protonic acid HA to form a compound of formula (A), wherein said HA is a suitable acid preferably selected from an inorganic acid or an organic acid, and
wherein further preferably said inorganic acid is selected from HBr, HCl, HI, HBF$_4$, HPF$_6$ and HClO$_4$, and said organic acid is selected from (C1-C5-alkyl)C(=O)OH, aryl-CH$_2$-C(=O)OH, [aryl-C(=O)OH, H$_3$PO$_4$, (C1-C6-alkyl)SO$_3$H, aryl-CH$_2$-SO$_3$H and aryl-SO$_3$H, and wherein again further preferably said inorganic acid is selected from HBr, HCl, HBF$_4$, HPF$_6$ and HClO$_4$, and said organic acid is selected from (C1-C6-alkyl)SO$_3$H.

14. A process for the preparation of the compound of formula (A)

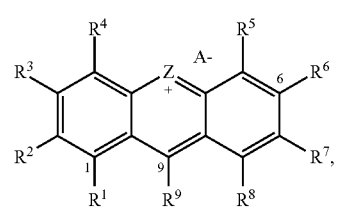

wherein
Z is selected from $NR^{10}$ and O;
$R^1$ is selected from C1-C6-alkoxy, OH, aryloxy, O-alkyl-aryl, C1-C6-hydroxyalkyl, $O(CH_2)O(CH_3)$, $O(CH_2)O(CH_2)_2OCH_3$, $NH_2$, N(H)(C1-C6-alkyl), $N(C1-C6-alkyl)_2$, SH, F, $CF_3$, C1-C6-alkylthio, 4,4-dimethyl-4,5-dihydrooxazole, $NHCOR^{14}$, $NHCO_2R^{14}$, $OCNR_2$, $CONHR^{14}$, $CON(R^{14})_2$, $C=NR^{14}$, $CO_2H$, $[CO_2^-]$, $CO_2R^{14}$, $SO_3R^{14}$, $SO_3H$, $[SO_3^-]$, $SO_2NC(CH_3)_3$, $SO_2N(R^{14})_2$;
$R^2$ is selected from H, halogen, $NO_2$, CN, $NH_2$, N(H)(C1-C6-alkyl), $N(C1-C6-alkyl)_2$, OH, C1-C6-alkoxy, C1-C6-hydroxyalkyl, SH, C1-C6-alkylthio, C1-C12-alkyl, $SO_3H$, $[SO_3^-]$, $SO_3R^{14}$, $CO_2H$, $[CO_2^-]$, $CO_2R^{14}$;
$R^3$ is selected from H, halogen, $NO_2$, $NH_2$, N(H)(C1-C6-alkyl), $N(C1-C6-alkyl)_2$, $NH_2$, N(H)(C1-C6-alkyl), $N(C1-C6-alkyl)_2$, OH, SH, C1-C6-alkylthio and CN;
$R^4$ is selected from H, C1-C12-alkyl, halogen, $NO_2$, CN, $NH_2$, N(H)(C1-C6-alkyl), $N(C1-C6-alkyl)_2$, OH, C1-C6-alkoxy, aryloxy, O-alkyl-aryl, C1-C6-hydroxyalkyl, SH, C1-C6-alkylthio, $SO_3H$, $[SO_3^-]$, $SO_3R^{14}$;
$R^5$ is selected from H, C1-C12-alkyl, halogen, $NO_2$, CN, $NH_2$, N(H)(C1-C6-alkyl), $N(C1-C6-alkyl)_2$, OH, C1-C6-alkoxy, aryloxy, O-alkyl-aryl, C1-C6-hydroxyalkyl, SH, C1-C6-alkylthio, $SO_3H$, $[SO_3^-]$, $SO_3R^{14}$;
$R^6$ is selected from H, halogen, $NO_2$, CN, $NH_2$, N(H)(C1-C6-alkyl), $N(C1-C6-alkyl)_2$, OH, C1-C6-alkoxy, aryloxy, O-alkyl-aryl, C1-C6-hydroxyalkyl, SH, C1-C6-alkylthio;
$R^7$ is selected from H, halogen, $NO_2$, CN, $NH_2$, N(H)(C1-C6-alkyl), $N(C1-C6-alkyl)_2$, OH, C1-C6-alkoxy, C1-C6-hydroxyalkyl, SH, C1-C6-alkylthio, C1-C12-alkyl, $SO_3H$, $[SO_3^-]$, $SO_3R^{14}$, $CO_2H$, $[CO_2^-]$, $CO_2R^{14}$;
$R^8$ is selected from H, halogen, C1-C6-alkoxy, OH, C1-C6-hydroxyalkyl, $O(CH_2)O(CH_3)$, $O(CH_2)O(CH_2)_2OCH_3$, $NH_2$, N(H)(C1-C6-alkyl), $N(C1-C6-alkyl)_2$, SH, F, $CF_3$, C1-C6-alkylthio, 4,4-dimethyl-4,5-dihydrooxazole, $NHCOR^{14}$, $NHCO_2R^{14}$, $OCN(R^{14})_2$, $CONHR^{14}$, $CON(R^{14})_2$, $C=NR^{14}$, $CO_2H$, $[CO_2^-]$, $NO_2$, $SO_3R^{14}$, $SO_3H$, $SO_2NC(CH_3)_3$ and $SO_2N(R^{14})_2$;
$R^9$ is selected from aryl, heteroaryl, C1-C4-alkyl-aryl, C2-C6-alkenyl-aryl, C2-C12-alkenyl, C2-C12-alkynyl, C1-C12-alkyl, H, $NH_2$, N(H)(C1-C6-alkyl), $N(C1-C6-alkyl)_2$, C1-C12-alkoxy, C1-C12-hydroxyalkyl, C(=O)H, C(O)-C1-C6-alkyl and C1-C12-alkylthio; and wherein said aryl and heteroaryl are optionally substituted by one or more groups independently selected from halogen atoms, CN, $N_3$, C1-C6-alkyl, $[SO_3]^-$, $SO_3H$, $SO_2Cl$, OH, C1-C6-alkoxy, C1-C4-alkyl-$CO_2H$, C1-C4-alkyl-$CO_2$-C1-C6-alkyl, C(=O)OH and C1-C6-alkoxycarbonyl, C1-C12-hydroxyalkyl, C1-C12-thioalkyl;
$R^{10}$ is selected from aryl, heteroaryl, C1-C4-alkyl-aryl, C2-C6-alkenyl-aryl, C2-C12-alkenyl, C2-C12-alkynyl, C1-C12-alkyl, H, C1-C12-hydroxyalkyl, C(=O)H, C(=O)-C1-C6-alkyl, C1-C12-alkylthio, C1-C12-alkyl-$CO_2H$; C1-C12-alkyl-$CO_2$-C1-C12-alkyl, C1-C12-alkyl-$CO_2$-C1-C4-alkyl-aryl, $O^-$; S(=O)-C1-C6-alkyl, S(=O)aryl, S(=O)-heteroaryl, $S(O_2)$-C1-C6-alkyl, $S(O_2)$-aryl, $S(O_2)$-heteroaryl; wherein said aryl and heteroaryl are optionally substituted by one or more groups independently selected from halogen atoms, CN, $N_3$, C1-C6-alkyl, $[SO_3]^-$, $SO_3H$, $SO_2Cl$, OH, C1-C6-alkoxy, C(=O)OH and C1-C6-alkoxycarbonyl;
$R^{14}$ is selected from C1-C12-alkyl; and
$A^-$ is a suitable anion preferably selected from halide ions, $[BF_4]^-$, $[PF_6]^-$, $[ClO_4]^-$, [(C1-C5-alkyl)C(=O)O]$^-$, [aryl-$CH_2$-C(=O)]$^-$, [aryl-C(=O)O]$^-$, $[H_2PO_4]^-$ $[HSO_4]^-[SO_4]^{2-}$, [(C1-C6-alkyl)$SO_3$]$^-$, $[CF_3SO_3]^-$, aryl-$CH_2$-$SO_3$]$^-$and [aryl-$SO_3$]$^-$;

comprising
(i) reacting a compound of formula (A''') with an organometallic reagent ($R^{12}M$) selected from aryl-MgX, C1-C6-alkyl-MgX, aryl-Li and C1-C6-alkyl-Li;

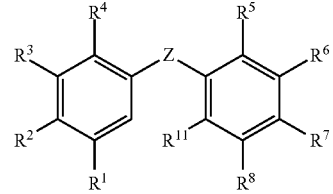

A''' to form a compound of formula (A'')

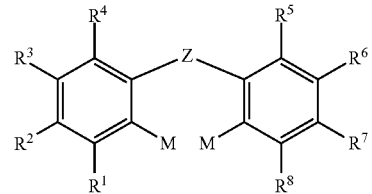

A'' wherein when $R^{11}$ is H, then $R^8$ is selected from C1-C6-alkoxy, OH, C1-C6-hydroxyalkyl, $O(CH_2)O(CH_3)$, $O(CH_2)O(CH_2)_2OCH_3$, $NH_2$, N(H)(C1-C6-alkyl), $N(C1-C6-alkyl)_2$, SH, F, $CF_3$, C1-C6-alkylthio, 4,4-dimethyl-4,5-dihydrooxazole, $NHCOR^{14}$, $NHCO_2R^{14}$, $OCN(R^{14})_2$, $CONHR^{14}$, $CON(R^{14})_2$, $C=NR^{14}$, $CO_2H$, $[CO_2^-]$, $SO_3R^{14}$, $SO_3H$, $[SO_3^-]$, $SO_2NC(CH_3)_3$, $SO_2N(R^{14})_2$; and
wherein when $R^{11}$ is halogen, then $R^8$ is selected from C1-C6-alkoxy, OH, C1-C6-hydroxyalkyl, $O(CH_2)O(CH_3)$, $O(CH_2)O(CH_2)_2OCH_3$, $NH_2$, N(H)(C1-C6-alkyl), $N(C1-C6-alkyl)_2$, SH, F, $CF_3$, C1-C6-alkylthio, 4,4-dimethyl-4,5-dihydrooxazole, $NHCOR^{14}$, $NHCO_2R^{14}$, $OCN(R^{14})_2$, $CONHR^{14}$, $CON(R^{14})_2$, $C=NR^{14}$, $CO_2H$, $[CO_2^-]$, $SO_3R^{14}$, $SO_3H$, $[SO_3^-]$, $SO_2NC(CH_3)_3$, $SO_2N(R^{14})_2$ and H; and
wherein M is Li when the organometallic reagent ($R^{12}M$) is aryl-Li or C1-C6-alkyl-Li; and wherein M is MgX when the organometallic reagent ($R^{12}M$) is aryl-MgX or C1-C6-alkyl-MgX or $MgX_2$ or $alkyl_2Mg$ or $aryl_2Mg$; and wherein X is a halogen;
(ii) followed by reacting said compound of formula (A'') with a compound of formula (B) or (C)

$R^9CO_2R^{13}$ (B)

$R^9COCl$ (C)

to form a compound of formula (A'),
wherein $R^{13}$ is C1-C6-alkyl, C1-C6-alkanoyl; or
wherein $R^9$ and $R^{13}$ together with the atoms to which they are attached form a 4 to 6-membered ring optionally substituted by C2-C6-alkenyl-aryl, C2-C12-alkenyl, C2-C12-alkynyl, C1-C12-alkyl, $NH_2$, N(H)(C1-C6-alkyl), $N(C1-C6-alkyl)_2$, C1-C12-alkoxy, C1-C12-hydroxyalkyl, halogen, CN, $N_3$, C1-C4-alkyl-$CO_2H$, C1-C4-alkyl -CO$_2$-C1-C6-alkyl, C(=O)H, C(=O)-C1-C6-alkyl and C1-C12-alkylthio; or wherein R$^9$ and R$^{13}$ together with the atoms to which they are attached form a 4 to 6-membered ring fused to an aryl or heteraryl, wherein said aryl or heteraryl is optionally substituted by one or more groups independently selected from halogen atoms, CN, N$_3$, C1-C6-alkyl, [SO$_3$]$^-$, SO$_3$H, SO$_2$C1, OH, C1-C6-alkoxy, C(=O)OH and C1-C6-alkoxycarbonyl, C1-C12-hydroxyalkyl, C1-C12-thioalkyl;

(iii) addition of a protonic acid HA to form a compound of formula (A), wherein said HA is a suitable acid preferably selected from an inorganic acid or an organic acid, and
wherein further preferably said inorganic acid is selected from HBr, HCl, HI, HBF$_4$, HPF$_6$ and HClO$_4$, and said organic acid is selected from (C1-C5-alkyl)C(=O)OH, aryl-CH$_2$-C(=O)OH, [aryl-C(=O)OH, H$_3$PO$_4$, (C1-C6-alkyl)SO$_3$H, aryl-CH$_2$-SO$_3$H and aryl-SO$_3$H, and wherein again further preferably said inorganic acid is selected from HBr, HCl, HBF$_4$, HPF$_6$ and HClO$_4$, and said organic acid is selected from (C1-C6-alkyl)SO$_3$H.

* * * * *